United States Patent
Ben Menachem et al.

(10) Patent No.: US 11,577,061 B2
(45) Date of Patent: *Feb. 14, 2023

(54) GASTRIC RESIDENCE SYSTEM

(71) Applicant: CLEXIO BIOSCIENCES LTD., Jerusalem (IL)

(72) Inventors: Avshalom Ben Menachem, Zur Izhak (IL); Ilan Zalit, Rosh Ha'ayin (IL); Elijahu Berkovich, Gedera (IL)

(73) Assignee: Clexio Biosciences Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/903,765

(22) Filed: Jun. 17, 2020

(65) Prior Publication Data
US 2020/0376242 A1 Dec. 3, 2020

Related U.S. Application Data

(63) Continuation of application No. 16/465,231, filed as application No. PCT/US2017/064417 on Dec. 4, 2017, now Pat. No. 10,737,079.

(60) Provisional application No. 62/430,166, filed on Dec. 5, 2016, provisional application No. 62/429,095, filed on Dec. 2, 2016.

(51) Int. Cl.
*A61M 31/00* (2006.01)
*A61B 5/00* (2006.01)
*A61K 9/00* (2006.01)
*A61K 47/69* (2017.01)
(Continued)

(52) U.S. Cl.
CPC ......... *A61M 31/002* (2013.01); *A61B 5/6871* (2013.01); *A61K 9/0065* (2013.01); *A61K 47/6903* (2017.08); *A61F 2002/5036* (2013.01)

(58) Field of Classification Search
CPC ............ A61M 31/002; A61K 47/6903; A61K 9/0065; A61B 5/6871
See application file for complete search history.

(56) References Cited

U.S. PATENT DOCUMENTS 1,318,259 A 10/1919 Bohne
3,844,285 A 10/1974 Laby
(Continued)

FOREIGN PATENT DOCUMENTS

EP 0202159 A2 11/1986
EP 0344939 A2 12/1989
(Continued)

OTHER PUBLICATIONS

Bardonnet et al., "Gastroretentive Dosage Forms: Overview and Special Case of Helicobacter Pylori", Journal of Controlled Release 111, 2006, 1-18.
(Continued)

*Primary Examiner* — Trevor Love
(74) *Attorney, Agent, or Firm* — BakerHostetler

(57) ABSTRACT

The present disclosure is in the field of gastric resident systems. A device for extended retention in a stomach is provided. The device includes: first, second, and third arms, the second and third arms being pivotally connected to respective ends of the first arm. The device is configured to transform between a compressed configuration and an expanded configuration. The device further includes a biasing member configured to bias the device into the expanded configuration whereby the second and third arms are configured to mechanically engage each other to retain the system in the expanded configuration.

20 Claims, 24 Drawing Sheets

(51) Int. Cl.
    *A61F 2/50*    (2006.01)
    *A61F 5/41*    (2006.01)

(56)         References Cited

U.S. PATENT DOCUMENTS

| | | | |
|---|---|---|---|
| 4,220,153 | A | 9/1980 | Dresback |
| 4,735,804 | A | 4/1988 | Caldwell et al. |
| 4,767,627 | A | 8/1988 | Caldwell et al. |
| 5,002,772 | A | 3/1991 | Curatolo et al. |
| 5,443,843 | A | 8/1995 | Curatolo et al. |
| 5,780,057 | A | 7/1998 | Conte et al. |
| 6,488,962 | B1 | 12/2002 | Berner et al. |
| 6,685,962 | B2 | 2/2004 | Friedman et al. |
| 6,723,340 | B2 | 4/2004 | Gusler et al. |
| 6,753,011 | B2 | 6/2004 | Faour |
| 7,976,870 | B2 | 7/2011 | Berner et al. |
| 8,298,574 | B2 | 10/2012 | Tsabari et al. |
| 8,329,215 | B2 | 12/2012 | Berner et al. |
| 8,460,706 | B2 | 6/2013 | Vergnault et al. |
| 8,586,083 | B2 | 11/2013 | Mohammad |
| 8,609,136 | B2 | 12/2013 | Tsabari et al. |
| 8,753,678 | B2 | 6/2014 | Tsabari et al. |
| 10,195,143 | B2 | 2/2019 | Zalit et al. |
| 10,485,758 | B2 | 11/2019 | Menachem et al. |
| 2005/0202090 | A1 | 9/2005 | Clarke |
| 2008/0241238 | A1 | 10/2008 | Dharmadhikari et al. |
| 2008/0299197 | A1 | 12/2008 | Toneguzzo et al. |
| 2009/0324694 | A1 | 12/2009 | Mohammad |
| 2010/0112053 | A1 | 5/2010 | Momose et al. |
| 2011/0066175 | A1 | 3/2011 | Gross |
| 2011/0117190 | A1 | 5/2011 | Brown et al. |
| 2011/0117192 | A1 | 5/2011 | Navon et al. |
| 2011/0268666 | A1 | 11/2011 | Friedman et al. |
| 2011/0301129 | A1 | 12/2011 | Berner et al. |
| 2012/0021009 | A1 | 1/2012 | Prinderre et al. |
| 2012/0263792 | A1 | 10/2012 | Lim et al. |
| 2012/0321706 | A1 | 12/2012 | Masri et al. |
| 2013/0072869 | A1 | 3/2013 | Cutchis et al. |
| 2013/0164377 | A1 | 6/2013 | Berner et al. |
| 2013/0197441 | A1 | 8/2013 | Tsabari et al. |
| 2014/0017303 | A1 | 1/2014 | Navon et al. |
| 2014/0148840 | A1 | 5/2014 | Mintchev et al. |
| 2015/0033850 | A1 | 2/2015 | Jeung et al. |
| 2015/0342877 | A1 | 12/2015 | Menachem et al. |
| 2016/0064439 | A1 | 3/2016 | Or-Bach et al. |
| 2017/0106099 | A1 | 4/2017 | Bellinger et al. |

FOREIGN PATENT DOCUMENTS

| | | |
|---|---|---|
| EP | 0415671 B1 | 3/1995 |
| EP | 1915990 A1 | 4/2008 |
| EP | 2329810 A1 | 6/2011 |
| GB | 1318259 A | 5/1973 |
| JP | 62-026215 A | 2/1987 |
| JP | 02-029268 A | 1/1990 |
| JP | 03-163011 | 7/1991 |
| JP | 2012-500230 A | 1/2012 |
| WO | 03/57197 A1 | 7/2003 |
| WO | 2006/072948 A2 | 7/2006 |
| WO | 2007/010847 A1 | 1/2007 |
| WO | 2007/072495 A2 | 6/2007 |
| WO | 2007/093999 A1 | 8/2007 |
| WO | 2007/106960 A1 | 9/2007 |
| WO | 2009/144558 A1 | 12/2009 |
| WO | 2010/035273 A2 | 4/2010 |
| WO | 2011/048494 A2 | 4/2011 |
| WO | 2011/090724 A3 | 11/2011 |
| WO | 2012/006961 A1 | 1/2012 |
| WO | 2012/006963 A1 | 1/2012 |
| WO | 2012/059815 A1 | 5/2012 |
| WO | 2013/054285 A1 | 4/2013 |
| WO | 2015/083171 A1 | 6/2015 |
| WO | 2015/187746 | 12/2015 |
| WO | 2015/191920 A1 | 12/2015 |
| WO | 2015/191922 A1 | 12/2015 |
| WO | 2018/102799 A1 | 6/2018 |

OTHER PUBLICATIONS

Bellinger et al., "Oral, Ultra-long-lasting Drug Delivery: Application Toward Malaria Elimination Goals", Sci. Transl. Med., 8, 2016, 365ra157.

Khosla et al., "The Effect of Tablet Size on the Gastric Emptying of Non-Disintegrating Tablets", International Journal of Pharmaceutics, 1990, 62(2-3), R9-R11.

Sharma et al., "Gastroretentive Drug Delivery System: An Approach to Enhance Gastric Retention for Prolonged Drug Release", IJPSR, 2014, vol. 5(4), pp. 1095-1106.

Timmermans et al., "The Cutoff Size for Gastric Emptying of Dosage Forms", J. Pharm. Sci., Aug. 1993, 82(8), 854.

Zema et. al., Journal of Controlled Release, "Injection Molding and its application to drug delivery", vol. 159 (2012) 324-331.

Zhoa et al., "Gastroretentive Drug Delivery Systems for the Treatment of Helicobacter Pylori", World J. Gastroenterology, Jul. 28, 2014, 20(28), 9321-9329.

Cardinal et al., "Gastric Retentive Drug Delivery Systems", Oral Bioavailability, 2011, 329-341.

Definition of "detach". Accessed online on Nov. 16, 2020 at https://www.merriam-webster.com. (Year: 2020).

Definition of "disengage". Accessed online on Nov. 16, 2020 at https://www.merriam-webster.com. (Year: 2020).

Definition of "insert". Merriam-Webster. Accessed online on Jul. 10, 2021 at merriam-webster.com (Year: 2021).

Fix et al., "Controlled Gastric Emptying, III. Gastric Residence Time of a Nondisintegrating Geometric Shape in Human Volunteers", Pharmaceutical Research, 1993, 10, 7, 1087-1089.

International Preliminary Report on Patentability dated May 20, 2016 in Corresponding International Application No. PCT/US 15/33850, 12 pages.

International Search Report dated Oct. 23, 2015 in corresponding International Application No. PCT/US15/33850.

Klausner et al., "Expandable Gastrorentensive Dosage Forms", Journal of Controlled Release, 2003, 90, 143-162.

Lopes et al., "Overview on Gastroretentive Drug Delivery Systems for Improving Drug Bioavailability", International Journal of Pharmaceutics, 2016, 144-158.

McLauchlan et al. "Comparison of gastric body and antral pH: a 24 hour ambulatory study in healthy volunteers" Gut, Oct. 1989, 30, pp. 573-578. (Year: 1989).

Rowe et al., Handbook of Pharmaceutical Excipients, "Cellulose Acetate Phthalate", 6th ed., 2009, Pharmaceutical Press, pp. 191-193. (Year: 2009).

Rowe et al., Handbook of Pharmaceutical Excipients, "Hypropmellose Phthalate", 6th ed., 2009, Pharmaceutical Press, pp. 333-336 (Year: 2009).

Sakshi, "Gastroretentive Drug Delivery Systems: An Overview", IPS, 2013, 37-45.

Shivram et al., "Gastro Rententive Drug Delivery System: A Review", IJPRAS, 2012, 1-13.

Tibbitt, "Emerging Frontiers in Drug Delivery", JACS, 2016, 138, 704-717.

Wang, Xiaobo, Drug Release System, China Medical Science Press, Chapter 27, Aug. 2007, pp. 483-485.

Zema, L. et al., "Gastroresistant Capsular Device Prepared by Injection Molding," International Journal of Pharmaceuticals, Jan. 2013, pp. 264-272, vol. 440.

Bellinger et al., "Supplemental materials for Oral, Ultra-long-lasting Drug Delivery: Application Toward Malaria Elimination Goals", Sci. Transl. Med., 8, 2016, 365ra157.

Hwang et al., Gastric Retentive Drug-Delivery Systems, Critical Reviews in Therapeutic Drug Carrier Systems, vol. 15 No. 3 pp. 243-284 (1998).

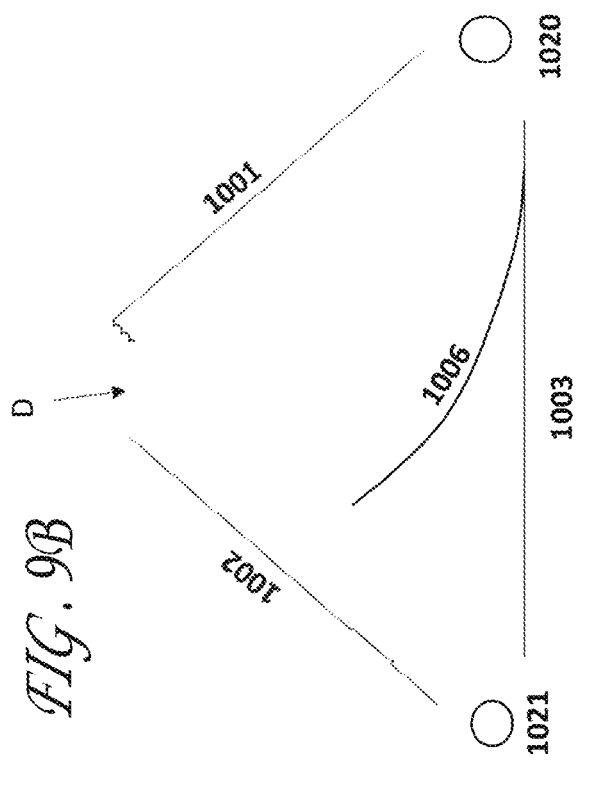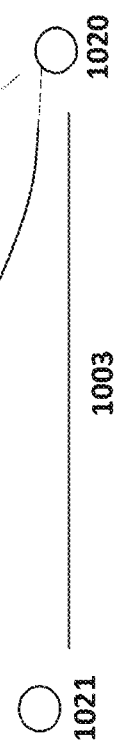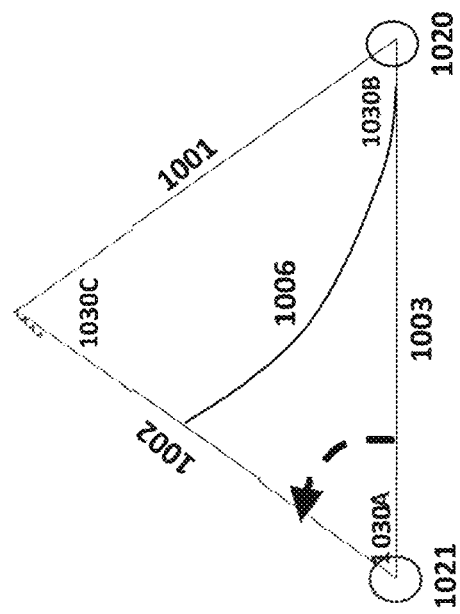
FIG. 9B
FIG. 9C
FIG. 9A

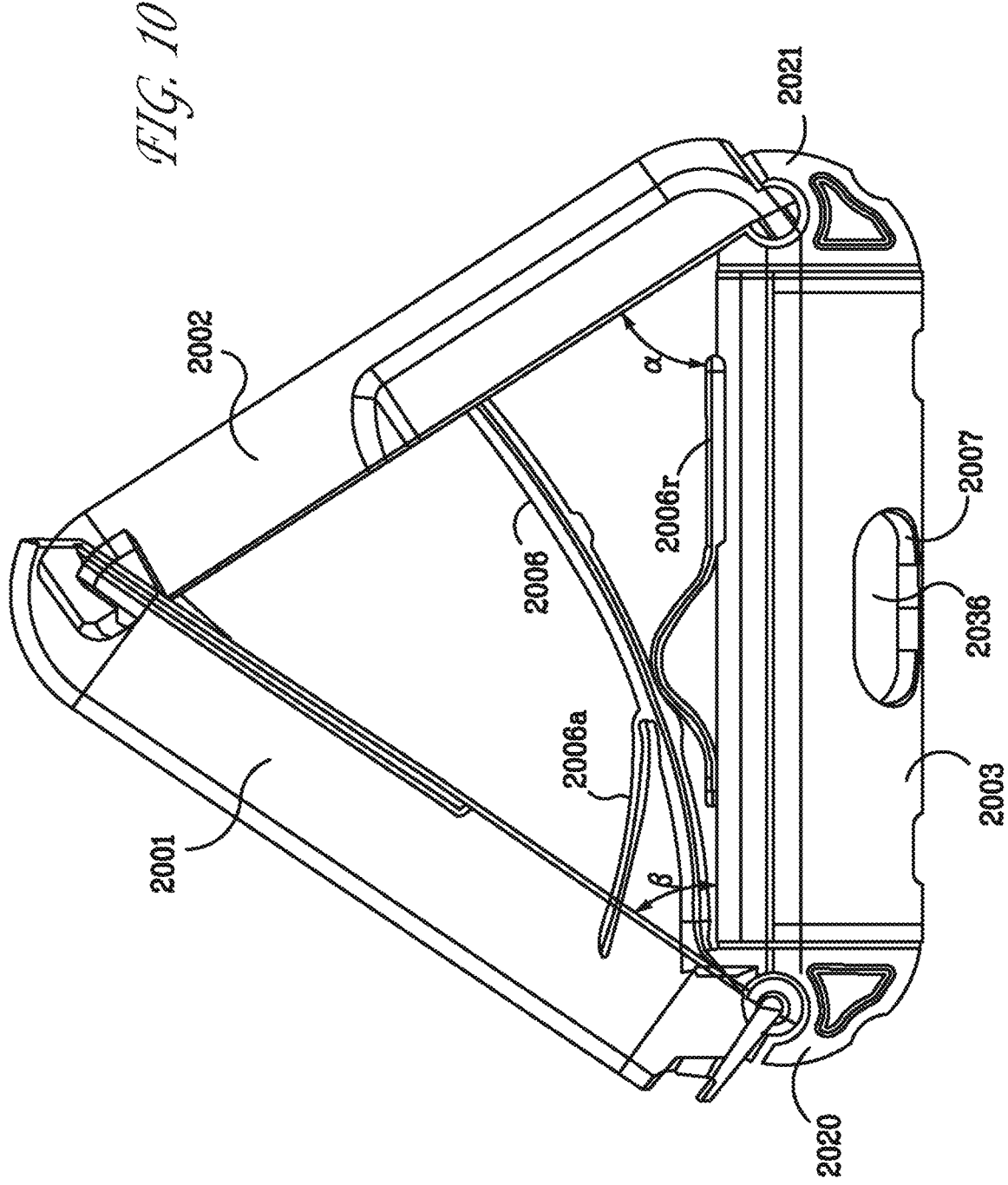

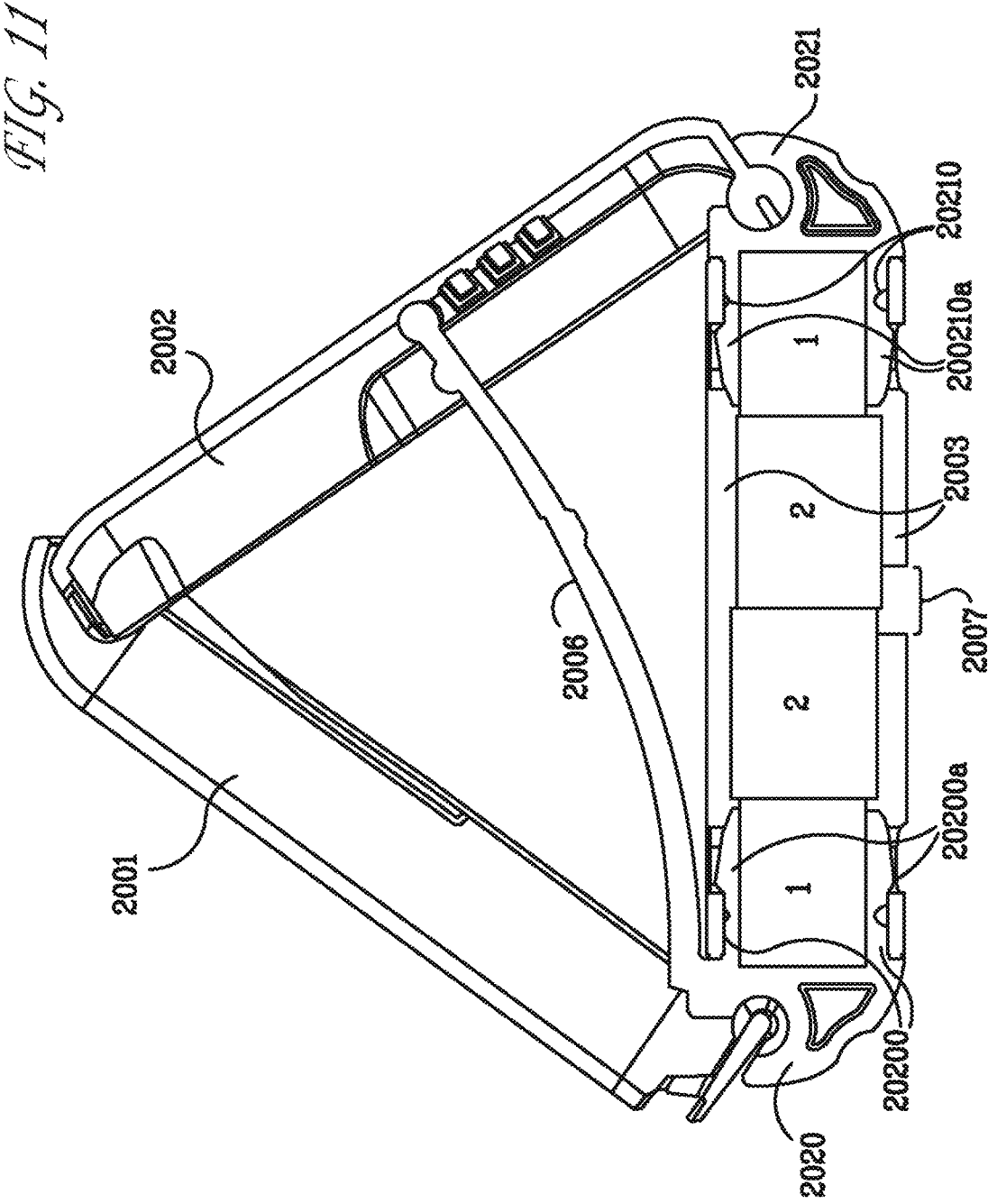

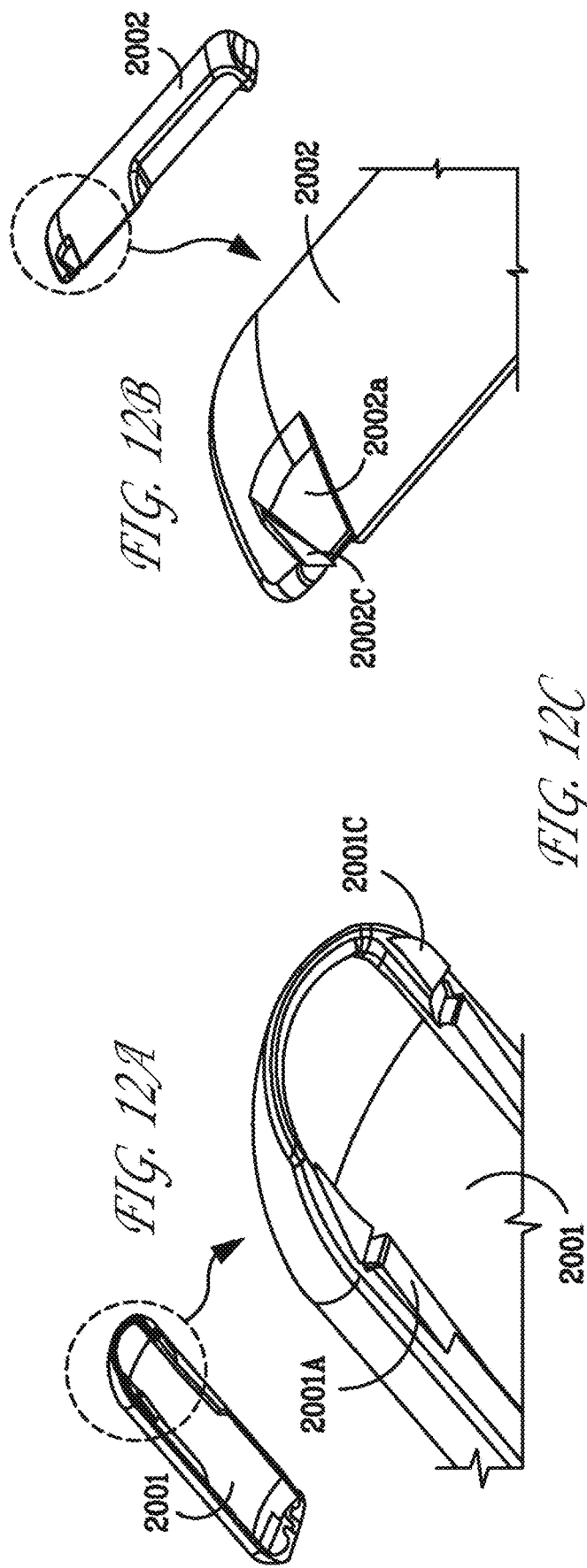
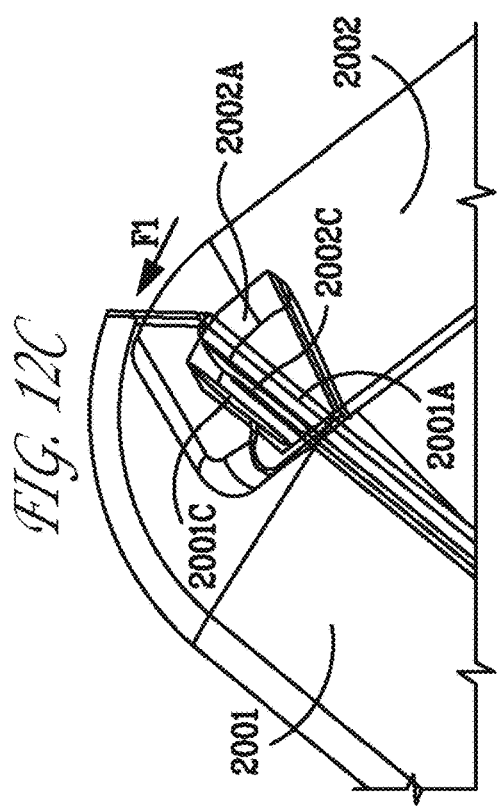

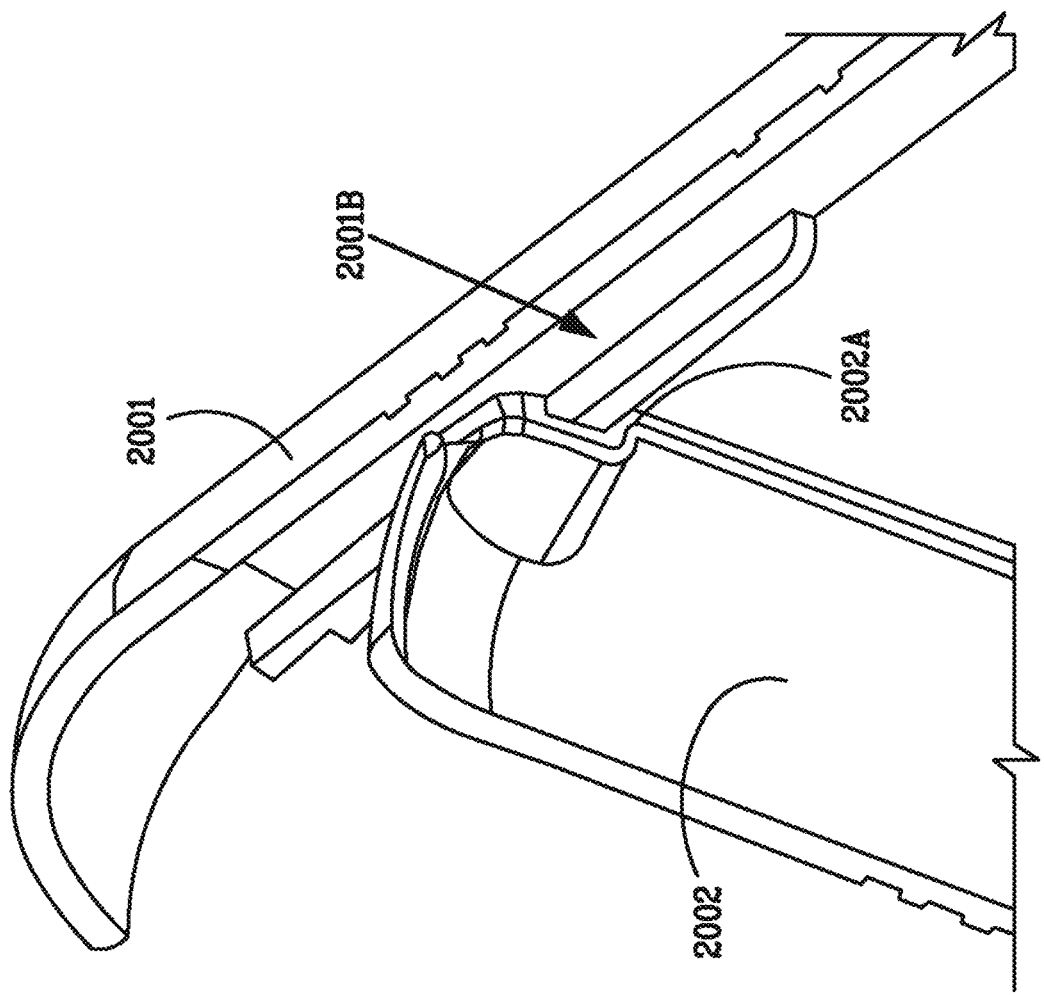

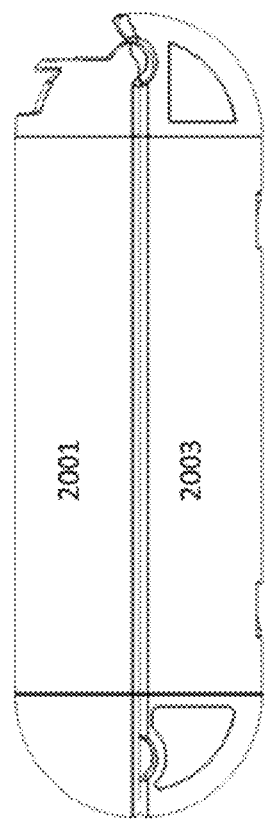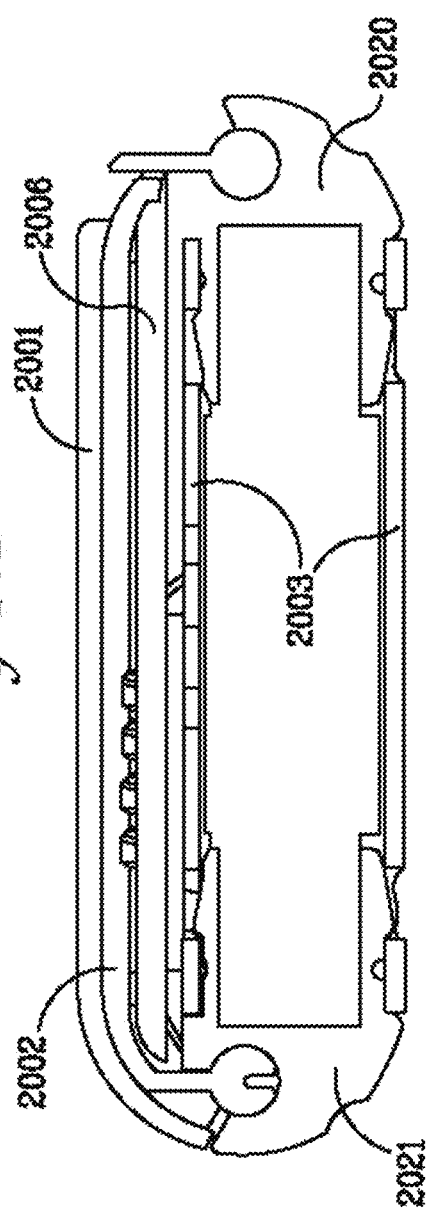

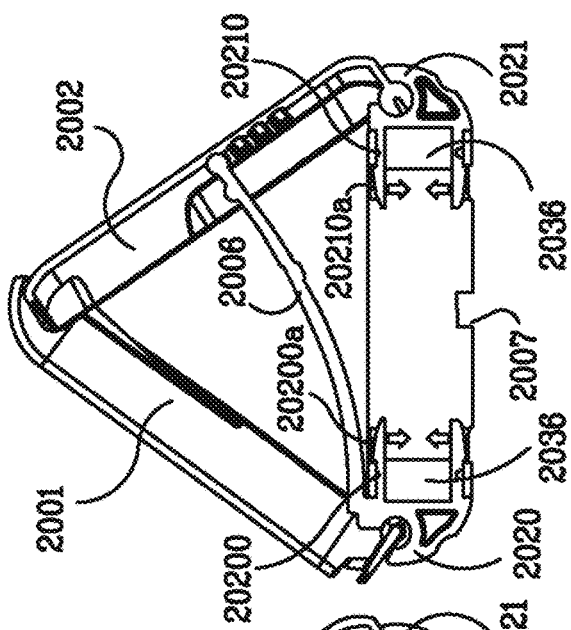
FIG. 15A
FIG. 15B
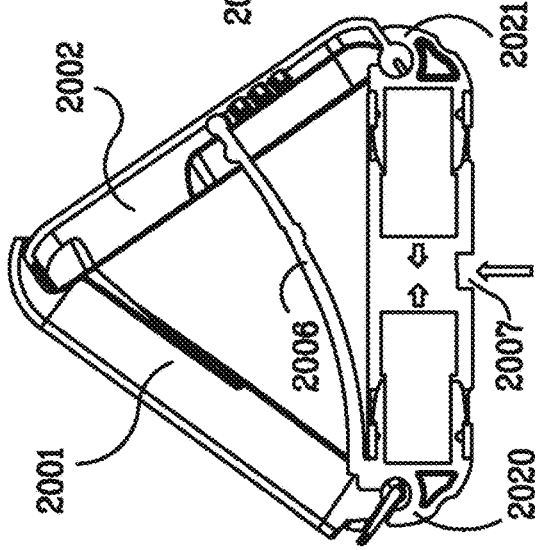
FIG. 15C
FIG. 15D
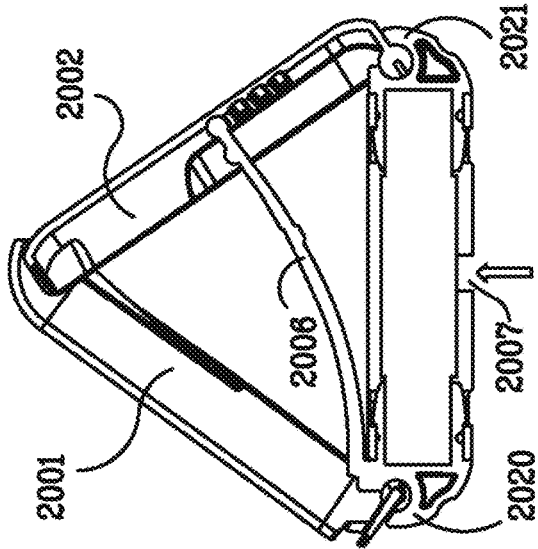

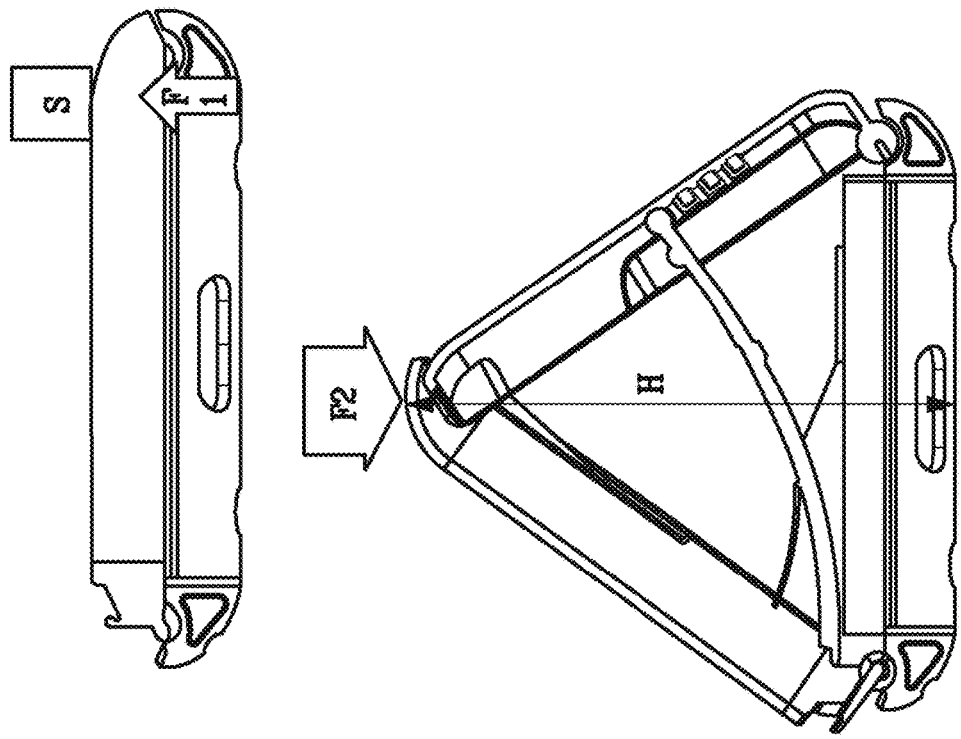
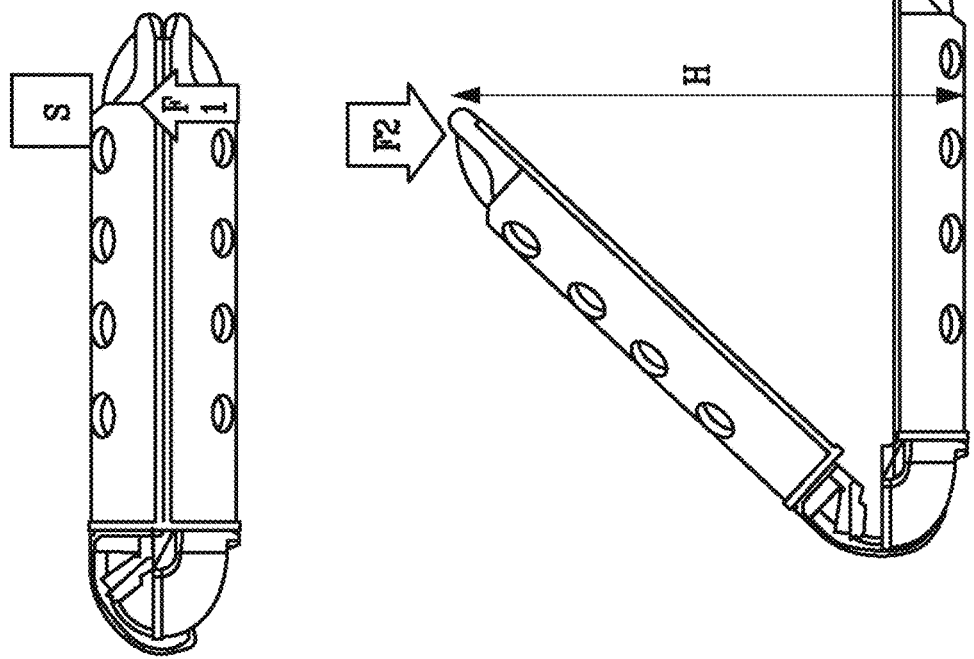

GASTRIC RESIDENCE SYSTEM

CROSS REFERENCE TO RELATED APPLICATIONS

This application is a continuation of U.S. Ser. No. 16/465,231, filed May 30, 2019, which claims the benefit of U.S. Provisional Application No. 62/429,095, filed Dec. 2, 2016 and U.S. Provisional Application No. 62/430,166, filed Dec. 5, 2016, the entire contents of each of which are incorporated herein by reference.

TECHNICAL FIELD

The present disclosure relates to a pharmaceutical product or system. More particularly, the present disclosure relates to an oral pharmaceutical or gastric residence system or gastroretentive dosage form and formulations relating thereto.

BACKGROUND

Gastric residence systems (GRS) are delivery systems which remain in the stomach for extended periods of time. They enable oral delivery of an active pharmaceutical ingredient (API), diagnostic or electronic device etc. to the gastrointestinal (GI) tract, for example for the purpose of extended GI residence, for local treatment of the upper GI, for continuous exposure of drugs especially those with a narrow absorption window or low solubility in the intestine. Gastric residence systems fall within three areas of technology: namely floating systems, bio-adhesives and systems with expanding geometry through swelling or unfolding.

Folding systems are conveniently administered to a patient in a folded or compacted form for example via a capsule. Once in the stomach, dissolution of the capsule in the stomach results in the system expanding or unfolding to a size which resists passage through the pyloric sphincter over the desired residence period. Examples of such systems are described in the following publications: U.S. Pat. No. 4,735,804, PCT/US2015/033850, PCT/US2015/035423, PCT/IB2011/002888.

Requirements for effective folding systems include providing a safe and pharmaceutically acceptable system which is compact for swallowing, unfold to effective expanded systems that can endure the mechanically and chemically harsh environment of the stomach for a desired residence period and eventually exit the stomach safely and in a timely manner. The present disclosure describes advancements in the design of improved structures for extended residence in the stomach.

SUMMARY

Aspects of the invention are defined in the accompanying claims.

According to a first aspect, there is provided a device for extended retention in a human stomach. The device includes a first arm having a first end and a second opposing end, a second arm and a third arm, the second and third arms being pivotally connected to the first end and the second end of the first arm, respectively. The device is configured to transform between a compressed configuration and an expanded configuration. The device further includes a biasing member configured to bias the device into the expanded configuration. In the expanded configuration the second and third arms are configured to mechanically engage each other to retain the device in the expanded configuration.

A portion of the second arm distal from the first arm and a portion of the third arm distal from the first arm may be configured to mechanically engage each other in the expanded configuration.

The third arm may include a retaining surface against which the second arm engages when the device is in the expanded configuration.

The third arm may include a protrusion against which the second arm engages when the device is in the expanded configuration.

The protrusion may be provided at an opposite end of the third arm to the first arm and wherein in the expanded configuration, the end of the second arm distal to the first arm may engage with the protrusion to form an apex.

During transformation from the compressed configuration to the expanded configuration, an outer surface of the second arm may be configured to slide along the third arm.

The third arm may include an elongate protrusion along its length and the second arm may include a recess configured to cooperate with the elongate protrusion during transformation from the compressed configuration to the expanded configuration.

In the expanded configuration the first, second and third arms may be configured to form a generally triangular shape.

A smallest turning radius of the triangular shape may be between 20 and 35 mm.

In the compressed configuration, the second arm may be configured to overlay the first arm and the third arm may be configured to overlay the second arm.

The second and third arms may be shaped such that an inner surface of the third arm has a corresponding shape to an outer surface of the second arm and an inner surface of the second arm has a corresponding shape to an outer surface of the first arm.

The biasing member may include an elongate member configured to bias the second arm.

The second arm may include a recess or protrusion configured to engage a portion of the biasing member when the device is in the expanded configuration.

The biasing member may include at least one of: an elastic leaf spring, a helical spring attached to a rigid member and a super porous hydrogel.

The device may further include a retainer configured to retain the device in the compressed configuration.

The retainer may include a wrapper, capsule or band surrounding the device thereby retaining the device in the compressed configuration.

The retainer may be configured to erode upon exposure to gastric fluid.

After a predetermined time period in the expanded configuration, the device may be configured to disassemble.

Disassembly of the device may include disconnection of the second and/or third arms from the first arm.

Upon disconnection of the second and/or third arms from the first arm, the second and third arms may be configured to disconnect from each other.

The first arm may include a cavity. The cavity may be formed from the interior of the sleeve or tube. The cavity may be configured to contain an erodible insert, diagnostic or electronic device. The erodible insert can include a pharmaceutical, diagnostic or electronic device.

The first arm may include an opening through which gastric fluid can enter the cavity.

The first arm may include a sleeve or tube. The tube or sleeve may provide a cavity. The sleeve or tube may comprise one or more sealing elements optionally at each end of the sleeve or tube The first arm may include an erodible insert, such as an erodible formulation or diagnostic.

Exposure of the erodible insert to gastric fluid for a predetermined time period may result in erosion of the erodible insert which is configured to cause the system to disassemble.

The first arm may include an erodible insert preferably an erodible formulation and the erodible formulation may be located in the cavity.

The sealing elements may each include at least one retaining element configured to extend into the sleeve or tube and the retaining elements may be located between the erodible insert and the sleeve or tube.

The erodible insert may be configured to provide an expansive force on the retaining elements thereby retaining the sealing elements in the sleeve or tube. Upon erosion of the erodible insert, the expansive force may be removed and the sealing elements may be configured to disassemble from the sleeve or tube. According to a further aspect there is provided a gastroretentive dosage form including a system as described above wherein the erodible insert is includes a pharmaceutical, diagnostic, or electronic device.

According to another aspect, a device is provided, the device includes a first arm having a first end and a second opposing end; a second arm pivotally connected to the first end of the first arm, a third arm pivotally connected to the second end of the first arm; and a biasing member connected to the second end of the first arm, said biasing member configured to transition the device from a compressed configuration to an expanded configuration, wherein in the expanded configuration the second arm and the third arm are mechanically engaged with each other to retain the device in the expanded configuration.

According to another aspect a method of preparing a gastroretentive dosage form is provided. The method includes: providing the device described above, inserting an erodible formulation preferably a pharmaceutical, diagnostic, electronic device or combination thereof in the device described above, compressing the device into a compressed state, locating the compressed state device within a retainer to retain it in the compressed state suitable for ingestion.

According to a further aspect a method of preparing a gastroretentive dosage form is provided. The method includes providing material for injection molding; injection molding individual parts including a first, second and third arm; optionally coating one or more arm(s) with enteric polymers; inserting an erodible formulation preferably comprising a pharmaceutical, diagnostic or electronic device into a first arm; connecting said first, second and third arm in the form of a triangle; and optionally compressing said triangular shaped system into a retainer. All materials may be pharmaceutically acceptable.

According to a still further aspect, a method of delivering an active pharmaceutical, device or diagnostic to the stomach for extended periods of time including providing a device as described above or a system as described above wherein one of the first, second and third arms includes an active pharmaceutical, device or diagnostic is provided.

A yet further aspect provides a kit of parts for assembly into the device described above. The kit includes first, second and third arms, and a biasing member.

According to a further aspect a kit for assembling a device described above is provided. The kit includes an expanded configuration of the device as described above and a retainer. Alternatively, the kit may include first, second and third arms of the device as described above, a biasing member and a retainer.

Any of the kits described can further include an erodible formulation, preferably comprising a pharmaceutical, diagnostic or electronic device.

BRIEF DESCRIPTION OF THE DRAWINGS

The teachings of the present disclosure will now be described by way of example only with reference to the following drawings in which like parts are depicted by like reference numerals:

FIGS. 9A-9C illustrate simplified drawings of the expanded state and disassembled states of the gastric residence system of FIGS. 1A-1B;

FIG. 10 is a front view of a gastric residence system in an expanded configuration;

FIG. 11 is a cross-sectional view of the gastric residence system of FIG. 10;

FIGS. 12A-C illustrate a close up view of a locking mechanism of the gastric residence system of FIG. 10, in which: FIG. 12A illustrates the engagement of arms 2001 and 2002 when locked together, FIG. 12B shows how planes 2001c and 2002c are angled such that the contact between the plane 2001c and the plane 2002c keeps arm 2001 locked with arm 2002, and FIG. 12C depicts how plane 2001c contacts plane 2002c when a radial force F1 is applied externally;

FIG. 13 illustrates a close up view of a guiding or sliding mechanism of the gastric residence system of FIG. 10;

FIG. 14A is a front view of the gastric residence system of FIG. 10 in a compressed configuration;

FIG. 14B is a cross-sectional view of the gastric residence system of FIG. 10 in a compressed configuration;

FIGS. 15A-15D are cross-sectional views illustrating the disassembly of the gastric residence system of FIG. 10;

FIGS. 20A and 20B illustrate a method of measuring the opening force via calculation of a minimum force applied to the device in the compressed state which prevents opening, and FIGS. 20C and 20D illustrate a measure of the rigidity of structure under a compression force applied to the apex of the device in the expanded state of a comparative example and the present gastric residence system disclosed herein.

Figure 1A:
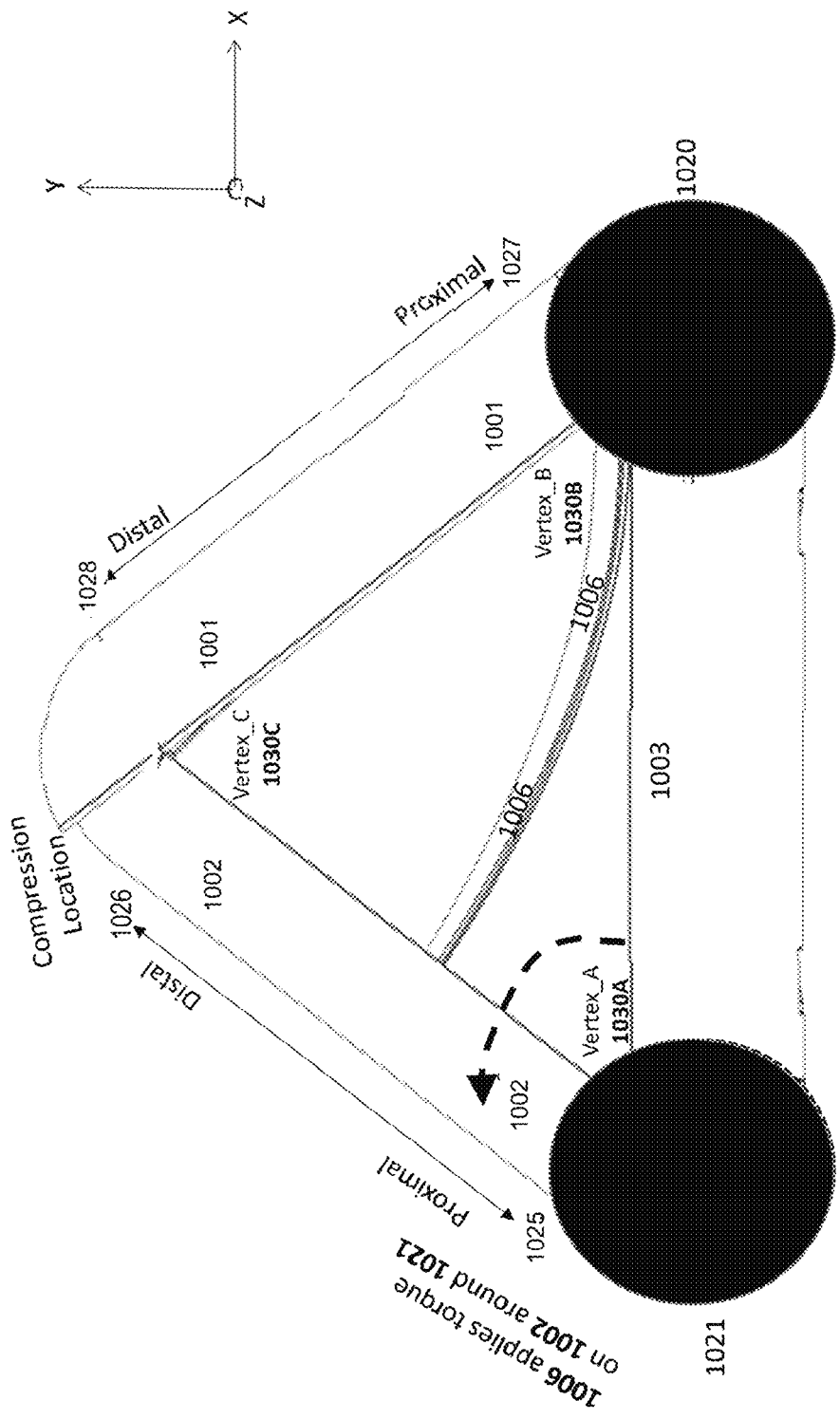
FIGS. 1A and 1B are schematic front views of a gastric residence system in an expanded configuration.

While the invention is susceptible to various modifications and alternative forms, specific embodiments are shown by way of example in the drawings and are herein described in detail. It should be understood, however, that the drawings and detailed description of the specific embodiments are not intended to limit the invention to the particular forms disclosed. On the contrary, the invention is intended to cover all modifications, equivalents and alternatives falling within the spirit and scope of the present invention as defined by the appended claims.

DETAILED DESCRIPTION

Definitions

The wording herein below is implied in the common meaning of the definitions and statements as known to those skilled in the art. However, there are several terms that should be understood in the concept of the present disclosure as follows:

"Gastroretentive device" refers to a mechanical device which is capable of residing in the stomach for a period of time. The device of the present disclosure provides a means for introducing an active pharmaceutical ingredient, diagnostic or electronic device for example into a subject. In the examples of the present disclosure this may be in the form of an erodible insert.

"Gastric residence system" or "gastroretentive delivery system" or "GRS" refer to a gastroretentive device containing an erodible insert or other means of timed disassembly of the device.

As used herein, the "erodible insert" is any formulation, material or composition which is capable of degradation, dissolution downsizing and/or disintegration based on exposure to gastric environment or simulated methods thereof.

"Gastroretentive dosage form(s)" (GRDF or GRDFs in the plural) refers to dosage forms which reside in the confines of the stomach for the purpose of providing a platform for the controlled release of biologically active agents or diagnostic formulations. In the present disclosure a gastroretentive dosage form refers to a gastric residence system that includes an active pharmaceutical ingredient, diagnostic or electronic device for example. The GRDF is also referred to herein as an oral pharmaceutical, as well as a dosage form for extended retention in a stomach.

"Gastric retention" is the maintenance or holding of an agent, for example a pharmaceutical, diagnostic or electronic device in the stomach, for a time period longer than the time it would have been retained in the stomach when delivered in a free form or within a gastro-intestinal (GI) delivery vehicle which is not considered gastroretentive. Gastro-retentivity may be characterized by retention in the stomach for a period that is longer than the normal emptying time from the stomach, such as longer than about 2 hours, in some cases longer than about 3 hours, and in many cases more than about 4, 6, 8 or 10 hours. Gastro-retentivity typically means retention in the stomach for a period of time of about 3, 4, 6, 8, 10, or at times 18 hours, even up to about 21 hours or longer. Gastro-retentivity may also mean retention in the stomach for a predetermined time period of at least 4, 6, 8, 10, 12, 18, 24, 48, 72, 96, 120, 144, 168 hours or longer.

"Gastro-intestinal retention" is the maintenance or holding of an agent, for example a pharmaceutical, diagnostic, electronic device or microchip in the gastrointestinal track [herein "GI"] for a time period longer than the time it would have been retained in the GI when delivered in a free form or within a gastro-intestinal (GI) delivery vehicle which is not considered GI retentive. GI retentivity may be characterized by retention in the GI for a period that is longer than the normal emptying time from the GI, such as longer than about 24 hours, 48, 72, 96, 120, 144, 168 hr or longer.

As used herein, a size "suitable for swallowing" is any size and/or shape that are capable of being safely swallowed by either a human or an animal. Unless specified otherwise, size for retention or reference to anatomy such as stomach or pyloric valve are in reference a human.

As used herein, a "body" is meant to include any collection of parts or materials that are more or less constrained or otherwise connected to move together by translation or rotation.

As used herein, "excipient" refers to an ingredient, or mixture of ingredients, that is used in the formulation of the compositions (including but not limited to the insert, the body parts—arm, etc.) of the present disclosure to give desirable characteristics to the composition or insert. As used herein, the term "pharmaceutically acceptable" refers to those compounds, materials, compositions, compacts, salts, and/or dosage forms which are, within the scope of sound medical judgment, suitable for contact with the tissues of human beings and animals without excessive toxicity, irritation, allergic response, or other problematic complications over the desired duration of treatment commensurate with a reasonable benefit/risk ratio. In some embodiments, the term "pharmaceutically acceptable" means approved by a regulatory agency of the Federal or a state government, such as the Inactive Ingredient Database of the FDA or listed in the U.S. Pharmacopeia or other generally recognized international pharmacopeia for use in animals, and more particularly in humans. Various pharmaceutically acceptable excipients can be used. In some embodiments, the pharmaceutically acceptable excipient can be, but is not limited to, an alkaline agent, a stabilizer, an adhesion agent, a separating agent, a coating agent, an exterior phase component, a controlled-release component, a solvent, a surfactant, a humectant, a buffering agent, a filler, an emollient, or combinations thereof. Excipients in addition to those discussed herein can include excipients listed in, though not limited to, Remington: The Science and Practice of Pharmacy, 21st ed. (2005). Inclusion of an excipient in a particular classification herein (e.g., "solvent") is intended to illustrate rather than limit the role of the excipient. A particular excipient can fall within multiple classifications.

As used herein, an "oral pharmaceutical" is anything administered orally whose components are made up of pharmaceutically acceptable materials.

As used herein, "diagnostic" or "an active pharmaceutical ingredient (API)" is meant to include any substance relevant for gastric retention as recognized in the art. A wide variety of APIs (which may be therapeutic, diagnostic or otherwise beneficial) may be employed in accordance with the aspects of the present disclosure. Any agent, for example an API or diagnostic which is relevant for gastric retentive delivery is intended to be encompassed herein. Relevant APIs are not limited to, but may include the following: APIs acting locally in the stomach; APIs primarily absorbed in the stomach; APIs poorly soluble in alkaline pH; APIs with narrow windows of absorption; APIs with poor patient adherence; APIs absorbed rapidly from the GI tract; APIs that degrade in the colon; and APIs that disturb colonic microbes. Diagnostics include medical imaging systems (e.g. scanner, MRI, camera, gastric stimulator, radiolabeled agents and the like. Electronic devices include microchips, imaging systems, transmitters and the like.

As used herein, the term "therapeutic agent" or also referred to as a "active agent", "active" or "active pharmaceutical ingredients" refers to an agent that is administered to a subject to treat a disease, disorder, or other clinically recognized condition, or for prophylactic purposes, and has a clinically significant effect on the body of the subject to treat and/or prevent the disease, disorder, or condition. Active pharmaceutical ingredients (APIs) may include but are not limited to the following: prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, bismuth salts, colchicine, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, metformin, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, 4-aminopyridine tobutamide, chlorproamide, tolazamide, acetohexamide, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-nor-progesterone, norgestrel, norethindrone, norethisterone, norethiederone, progesterone, norgesterone, norethynodrel, terfenadine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, carbidopa, selegiline, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine, and pharmaceutical salts of these active agents. Further examples are proteins and peptides which include, but are not limited to, cyclosporins such as cyclosporine A, insulin, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor. Listings of additional examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. In certain embodiments, the therapeutic agent is a small molecule. In certain embodiments, the therapeutic agent may be one or more therapeutic agents.

As used herein, "gastric retentive endpoint" may be dependent on a "time dependent disassembly mechanism" or "timed disassembly" or "timed downsizing" wherein the device loses its mechanical integrity as a single unit for example, through any one or more of the following: opening the closed circuit and/or disassembly of an articulated body; and/or cleaving a connection between a mediating sleeve, tube, arm and another arm or pivotal connection thereof for example a hinge; and/or significant pharmaceutical-releasing erosion of the erodible.

As used herein, "pharmaceutical-releasing" is meant to include any formulation which is designed to undergo degradation, dissolution, disintegration etc. when exposed to gastric environment. Pharmaceutical formulations can include one or more therapeutic agents or active pharmaceutical ingredients.

As used herein, the "gastric-fluid-erodible wrapper" is meant to include any standard means for packaging pharmaceuticals for delivery into the stomach such as capsules. The means may erode, dissolve and/or disintegrate within minutes of reaching the gastric environment.

As used herein, the term "arm" or "arms" includes any structure that includes a length, width and thickness and aids in achieving a device of a size suitable for gastric retention. In some embodiments, the length of each arm may be about at least 1.5 or at least 2.0 or at least 2.5 or about 2.5 to about 3.0 or at most 3.0 or at most 2.8 or at most 2.7 or at most 2.6. At least one arm of the gastroretentive device as described herein retains an active pharmaceutical, diagnostic, electronic device etc. For example the at least one arm may define a cavity therein configured to retain an erodible insert or pharmaceutical tablet (which includes one or more APIs, diagnostics, electronic devices, excipients and/or polymers).

As used herein, the term "hinge assembly" includes any mechanism adapted to permit relative pivotal movement between two or more structures, e.g., arms. The hinge assembly may include of one integral part (e.g., a living hinge) or one or more parts that are assembled in the conventional sense. The hinge assembly may be durable in the stomach for a period of time, and it may attach to one or more arms in both the collapsed and expanded configurations. The hinge assembly may be capable of, at a predetermined time or upon occurrence of a mechanical event, disengaging from the one or more arms.

As used herein, the term "mechanical event" includes any event that changes the physical properties of one or more structures over time or upon contact with another material or fluid, e.g., gastric fluid inside the body. Absorption, dissolution, melting, degradation, erosion, etc. are all examples of mechanical events.

As used herein an "erodible" material includes any one or more units composed of material that degrades, dissolves, disintegrates or downsizes upon introduction to a specified environment or upon contact with a specified material or fluid, e.g., a gastric environment or gastric fluid.

As used herein, the terms "compressed configuration" and "collapsed configuration" are used interchangeably and refer to a state prior to ingestion where the gastroretentive device has a size suitable for swallowing.

As used herein, the term "expanded configuration" is a state after ingestion where the gastroretentive device is in a state that permits retention in the stomach (gastric retention) and prevention of passage through the pyloric valve.

As used herein, the term "upon exposure to gastric fluid" or "under simulated gastric conditions" unless expressed otherwise is meant to be taken literally or when needed, based on a suitable model. One example of such a suitable model includes a rotating bottle apparatus at 37° C. at 2-5 RPM having 400 mL 0.01N HCl, pH2 and optionally Xanthan gum 0.125 gr/L As used herein, the term "pharmaceutically acceptable" refers to a material that is not physically or otherwise unacceptable when used in accordance with the disclosure. For example, the term "pharmaceutically acceptable carrier" refers to a material that can be incorporated into a composition and administered to a patient without causing unacceptable physiological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

As used herein, any term relating to geometric terms, shape and/or orientation shall, unless otherwise defined or indicated, be understood to indicate conformance to the mathematical definition of such term to the extent possible for the subject matter so characterized as would be understood by one skilled in the art and would not to require absolute conformance to a mathematical definition of such term. Examples of such terms relating to geometric terms, shape and/or orientation include, but are not limited to terms descriptive of: shape (such as, round, square, circular/circle, rectangular/rectangle, triangular/triangle, cylindrical/cylinder, elliptical/ellipse, (n)polygonal/(n)polygon, vertex etc.); angular orientation (such as perpendicular, orthogonal, parallel, vertical, horizontal, collinear, etc.); contour and/or trajectory (such as, plane/planar, coplanar, hemispherical, semi-hemispherical, line/linear, hyperbolic, parabolic, flat, curved, straight, arcuate, sinusoidal, tangent/tangential, etc.); surface and/or bulk material properties, spatial/temporal resolution, distribution (such as, smooth, reflective, transparent, clear, opaque, rigid, impermeable, uniform(ly), inert, non-wettable, insoluble, steady, invariant, constant, homogeneous, etc.); as well as many others that would be apparent to those skilled in the relevant art. As one example, a system that would be described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described.

In the following description the terms "house", "contain", "received" (for example where the erodible insert is described as being received in the cavity) are all used synonymously and are used to mean "held within". The skilled person will appreciate that these terms are used interchangeably without any change in scope.

As used herein, the terms "constructed from" and "formed of" may be used interchangeably and are intended to mean that a component is made from or otherwise comprises a specified material. The term "substantially" is intended to mean considerable in extent or largely but not necessarily wholly that which is specified. The terminology includes the above-listed words, derivatives thereof and words of similar import.

As used herein, the term "opening force" is intended to describe the force of bias by the compressed state device to open into the expanded configuration as illustrated, for example in F1 of FIG. 20A and FIG. 20B or at least progress by 10% towards the expanded state configuration. The opening force may be calculated by deriving the minimum force required to maintain the gastric retentive device in compressed state as measured on a rigid surface.

As used herein, the term "rigidity" is the property of a device which expresses the ability to resist change in size despite application of a force. In this case, it is the extent to which a device is capable of resistance to a 10% decrease in any dimension of the expanded state gastric retentive device under application of a minimum force as illustrated for example in F2 in FIGS. 20C and 20D.

Description of Device

The present disclosure provides a gastroretentive delivery system comprising a gastroretentive device and a method of use thereof. The gastroretentive delivery system is swallowed in a compressed configuration, expands in the stomach, performs its intended function for a predetermined time period, and at the end of the time period or upon occurrence of a mechanical event, disassembles into smaller components for eventual passage through the pyloric valve of the stomach.

After exiting the stomach, the disassembled components of the gastroretentive delivery system safely pass through the rest of the gastrointestinal system and are expelled from the body and/or are gradually eroded by pH conditions of the intestine. In some examples, disassembled components are configured to completely disintegrate. In other examples, the disassembled components are configured to disintegrate to an extent necessary for evacuation from the body. In yet other examples, components of the gastroretentive delivery system do not disintegrate and are evacuated intact.

According to the example, devices described in detail below, the gastroretentive delivery system has a modular design that combines a structural gastroretentive device and a means for controlled timing of disassembly or downsizing such as an erodible composition located within the gastroretentive device. The gastroretentive device has a size, strength and shape that facilitates gastric residence as will be discussed in further detail below, and is configured to resist degradation, dissolution, erosion or downsizing in the stomach until the required time at which point it is configured to disassemble, or downsize for safe passage out of the stomach into the intestinal environment. The erodible composition associated with the gastric residence system is configured to degrade, dissolve, erode or downsize in the stomach thereby controlling the time at which the size and strength of the gastric residence system is lost resulting in disassembly and downsizing such that passage of the component parts of the structural gastroretentive device from the gastric environment is possible. It will be appreciated that because the erodible composition is for the most part located internal to the gastroretentive device (except for a limited surface of erosion), the characteristics of the device are maintained until a period of time close to the disassembly event.

FIGS. 1-5 and 7-10 illustrate schematic examples of a gastroretentive device, a gastroretentive delivery system incorporating a gastroretentive device or gastroretentive dosage form incorporating a gastroretentive system. The device has collapsed or compressed, expanded and disassembled configurations. FIGS. 1A and 1B show the device in the expanded configuration. The device of FIG. 1A comprises an articulated body that includes three arms 1001, 1002 and 1003. Arms 1001 and 1002 are pivotally connected to the ends of arm 1003. In the illustrated example arms 1001 and 1002 are pivotally connected to arm 1003 by means of two hinge assemblies 1021, 1020. Arms 1001 and 1003 extend from, and may pivot around hinge assembly 1020; arms 1002 and 1003 extend from, and may pivot around hinge assembly 1021. In a preferred example, arm 1003 is not pivoted around hinge assemblies 1020 and 1021. Instead only arm 1001 is pivoted around hinge assembly 1020 and only arm 1002 is pivoted around hinge assembly 1021.

In the expanded configuration, the arms 1001, 1002, 1003 form a closed circuit—e.g. a polygon or circle. It will be appreciated that although the term polygon is used throughout, in a case that the sides or arms have a curved shape in expanded state, the final shape may resemble a circle. In the non-limiting example of FIGS. 1A-1B and 2A-2B the polygon is a triangle such that the three arms form a generally triangular shape. It will be appreciated however that polygons comprising more than three sides are also contemplated. The triangle may be any form of triangle, for example an isosceles triangle or an equilateral triangle. The triangle has three vertices—1030A-1030C (the term vertex, which may also be referred to as apex, is a mathematical term for each angular point or corner of a polygon). As discussed below, in the example of FIGS. 1-2, vertices 1030A-1030B are 'hinged' while vertex 1030C is 'hinge less' in that arms 1002 and 1001 are not pivotally connected to one another. In the illustrated example vertex 1030C is formed in situ as the device transitions from a collapsed to an expanded state.

Also illustrated in the drawings is elastic leaf spring 1006 which mechanically biases the device from a collapsed state to an expanded state. 1006 applies a torque on 1002 around 1021.

Figure 1B:
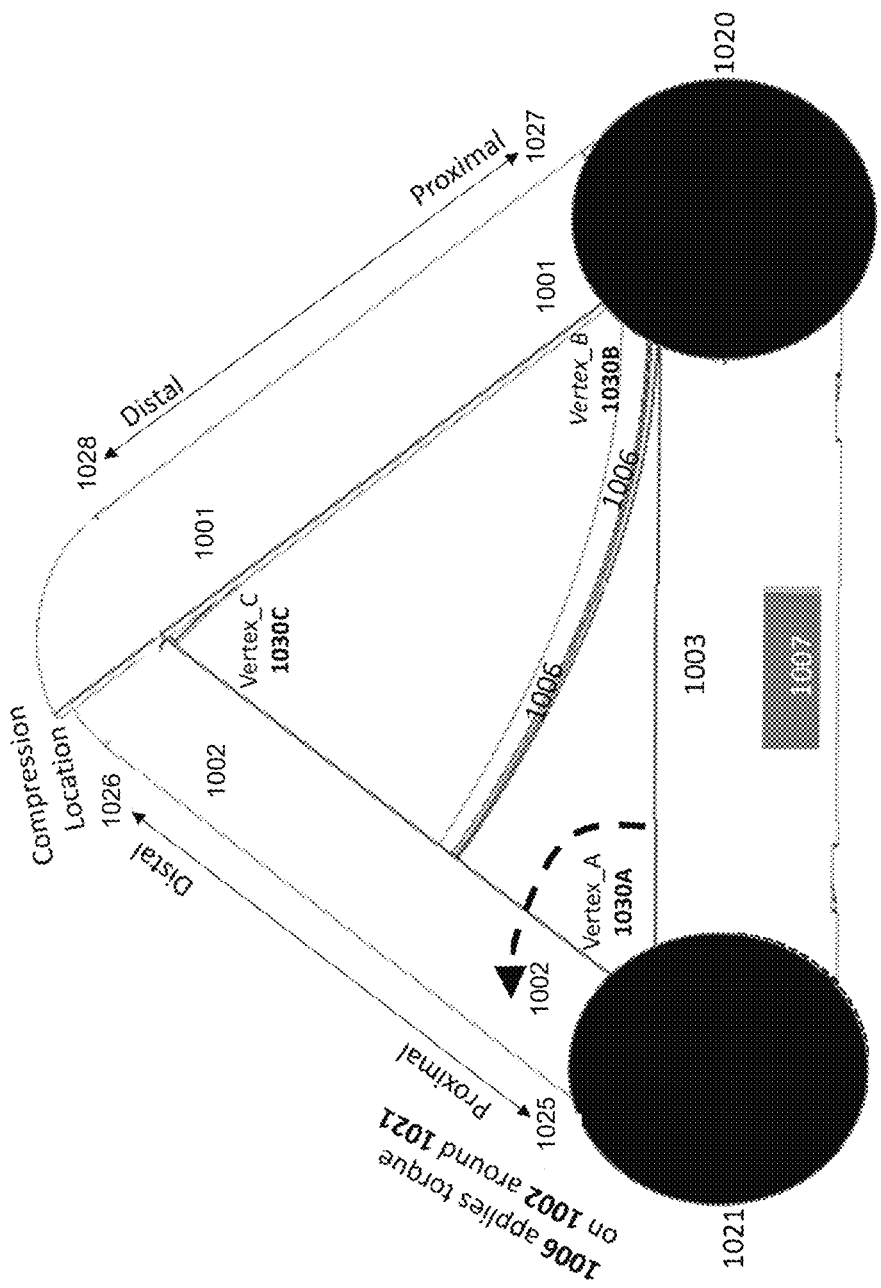

In the exemplary device of FIGS. 1A-1C, arms 1001-1003 thereof form a closed circuit (e.g. polygon). In the device of FIGS. 1A-1C, arms 1001-1003 are effectively sides (e.g. elongated sides) of a closed polygon when the device is in the expanded configuration. Although arms 1001-1003 are straight in their elongate direction in the example of FIGS. 1-2, this is not a requirement and one or more of the arms may alternatively be curved.

Arms 1001, 1002 and 1003 are all formed of a relatively rigid material such that they maintain their shape in both the expanded and compressed configurations. Thus the body is provided with sufficient strength to withstand the forces acting on it in both fasted and fed conditions of the stomach. In the illustrated example, the length of arms 1001, 1002 and 1003 are each individually comparable to the length of the compressed form and the width of each arm is comparable to the width of the compressed form. The depth of the arms when arranged in the compressed configuration is comparable to the depth of the compressed form. In the present disclosure, length is considered to correspond to the x-axis illustrated in FIG. 1A, width is considered to correspond to the z axis illustrated in FIG. 1A and depth is considered to correspond to the y axis illustrated in FIG. 1A.

In the example of FIGS. 1A-1B, hinge assemblies 1020, 1021 are attached to each end of side 1003, thus, side 1003 may be referred to as a 'mediating' side. The mediating side can be configured to provide a timed disassembly or alternatively can be configured to contain an active, diagnostic and/or electronic. In some examples where the mediating side provides a timed disassembly, an active, diagnostic and/or electronic may form another part of the device. In some examples, the mediating side can be configured to provide a timed disassembly and to contain an active, diagnostic and/or electronic.

As will be discussed below, arm 1003 has a cavity in which an insert can be located.

As shown in FIG. 1B, an opening, 1007, is provided in arm 1003 to permit gastric fluid to enter the cavity when the system is in the stomach in In the illustrated example, arm 1003 is in the form of a tube or sleeve. In the illustrated example the tube or sleeve has a circular cross section and is thus in the form of a hollow cylinder having a cavity. However the tube may have alternative cross-sectional shapes such as square or rectangular. In some examples the cross section of the tube is an irregular polygonal shape. As discussed above, the tube is arranged to house an erodible insert, 1036, FIGS. 2A and 2B. In some examples the erodible insert has a complementing contour to the interior of the tube. In other examples the erodible insert fills only a portion of the interior of the tube. The tube may in any case be considered to form a shell or sleeve that surrounds an erodible insert, diagnostic or electronic device or combinations thereof. The tube, shell or sleeve has mechanical durability independent of its contents throughout its duration in the stomach.

The tube or sleeve may be constructed from material that is insoluble in gastric fluid. Alternatively the outer surface of the tube or sleeve comprises a pharmaceutically acceptable material which is insoluble in gastric fluid, for example at about 37 degrees C. As will be discussed below, in some embodiments, an erodible insert which may be in the form of one or more tablets (e.g. pharmaceutical-containing) may be disposed within arm 1003.

Figure 4A:
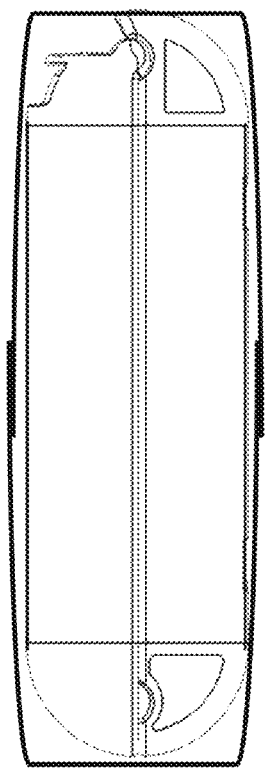
FIG. 4A is a front view of the gastric residence system of FIGS. 1A and 1B in a compressed configuration.

Arms 1001 and 1002 have a different construction than arm 1003 to allow the device to be compressed to a compressed or collapsed configuration. Specifically, in the illustrated example, arms 1001 and 1002 have a generally hollow semi-cylindrical shape. Put another way arms 1001 and 1002 are hollow and have a generally semi-circular cross section. The ends of arms 1001 and 1002 distal to arm 1003 are in the shape of a quarter hemispheres that closes what would otherwise be an open end of arms 1001 and 1002. Since arm 1003 has a substantially cylindrical shape and arms 1001 and 1002 have a generally hollow semi-cylindrical shape, the arms are able to overlay one another for example to form a nested arrangement in the compressed configuration as illustrated in FIG. 4C.

As discussed above, the shell or sleeve of arm 1003 may define an opening, void or window 1007 therein via which gastric fluid can penetrate the system so as to erode (e.g. pharmaceutical-containing erodible) the erodible insert disposed within the shell or sleeve. In some embodiments, this opening or window 1007 is relatively small—as will be discussed below, this allows for a controlled and/or directional release of the erodible insert within the sleeve or shell. In the non-limiting illustrated example, a single opening or window is shown—it is appreciated that in other embodiments, a plurality of openings or windows may be provided.

The erodible insert may comprise a pharmaceutical, diagnostic or electronic device or combination thereof. For examples, where the erodible insert is a pharmaceutical-containing erodible insert, erosion thereof releases pharmaceutical into gastric fluid. Thus, in this case erosion of the erodible insert is pharmaceutical-releasing erosion.

Figure 2A:
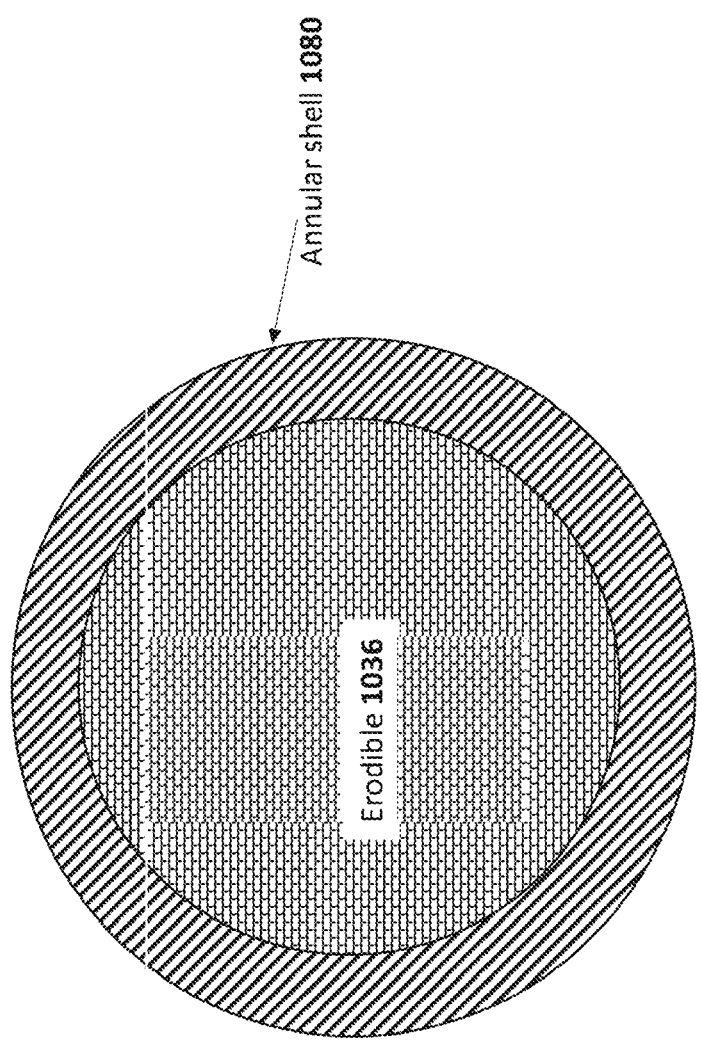
FIG. 2A is a cross sectional view of an erodible insert contained within an arm of the gastric residence system of FIGS. 1A and 1B.
Figure 2B:
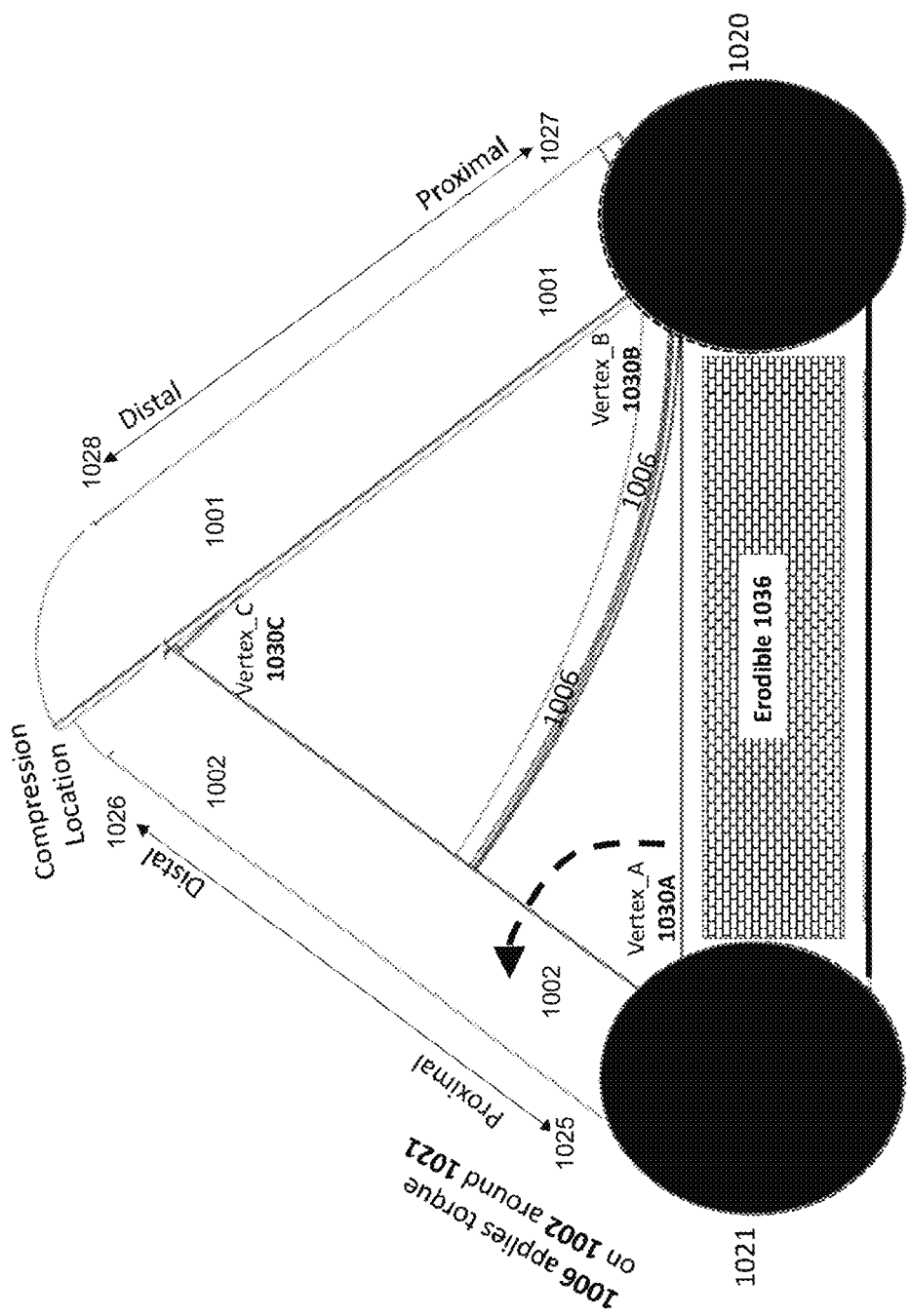
FIG. 2B is a schematic front view of the gastric residence system of FIGS. 1A and 1B illustrating the erodible insert located within the system.

FIG. 2A-2B illustrate the erodible insert 1036 (e.g. a tablet) within arm 1003. FIG. 2A is a cross section of arm 1003 and shows an annular shell 1080 or sleeve that is constructed of gastric-fluid-insoluble, pharmaceutically acceptable material and/or has an outer surface that is gastric-fluid-insoluble. Put another way, annular shell 1080 or sleeve is a protective shell or sleeve so that only gastric fluid which enters via opening(s) 1007 (see FIG. 1B) contacts the erodible therein—this allows for greater control of the erosion process such that for example the erosion is directional for example eroding from the center outwards. In some example, it may also be appreciated that the surface area and rate of erosion remains substantially consistent throughout the erosion process.

In the example of FIGS. 1A-1B, a proximal end of side/arm 1002 is labelled as 1025; a distal end hereof is labelled as 1026; a proximal end of side/arm 1001 is labelled as 1027; a distal end hereof is labelled as 1028.

In the example of FIGS. 1A-1B, pressure applied by leaf spring 1006 applied upon arm/side 1002 provides a torque around hinge assembly 1021. The leaf spring 1006 is an elastic leaf spring and biases the device into the expanded configuration, thus the leaf spring 1006 acts as a biasing member. In the illustrated example the leaf spring extends between hinge assembly 1020 and arm 1002 in the expanded configuration. However the leaf spring may extend between arm 1003 and arm 1002 in the expanded configuration. The biasing member may form a part of another component. For example, the biasing members may be a portion of the hinge assembly mediating arm. In another example, the biasing member is a separate component.

In order to bias both arms 1001 and 1002 into the expanded configuration, the leaf spring is arranged between arm 1003 and arm 1002 when the arms overlay one another in the compressed configuration. In this manner the leaf spring acts on the arm 1002 which itself acts on the uppermost arm 1001 thereby biasing both arms into the expanded configuration.

As will be discussed below, in some embodiments at least one vertex 1030C may be hinge less. In the example of FIGS. 1A-1B (schematically illustrated in FIGS. 3A-3B), pressure applied by leaf spring 1006 upon arm 1002 (which provides a torque around hinge assembly 1021) urges a surface of arm 1002 at distal end 1026 thereof against a portion of side 1001 at distal end 1028 thereof to provide compression or a compressive force there between (see FIG. 3C). This compressive force causes the arms 1001 and 1002 to mechanically engage, thereby locking arms 1001 and 1002 together. As illustrated in examples, sustaining of this compressive force is required to maintain (e.g. stably maintain) vertex 1030C. As will be discussed below (e.g. in the context of disassembly—see FIG. 7), in some embodiments, ceasing of this compressive force (e.g. due to the ceasing of the torque around hinge 1021) dismantles vertex 1030C.

Figure 3A:
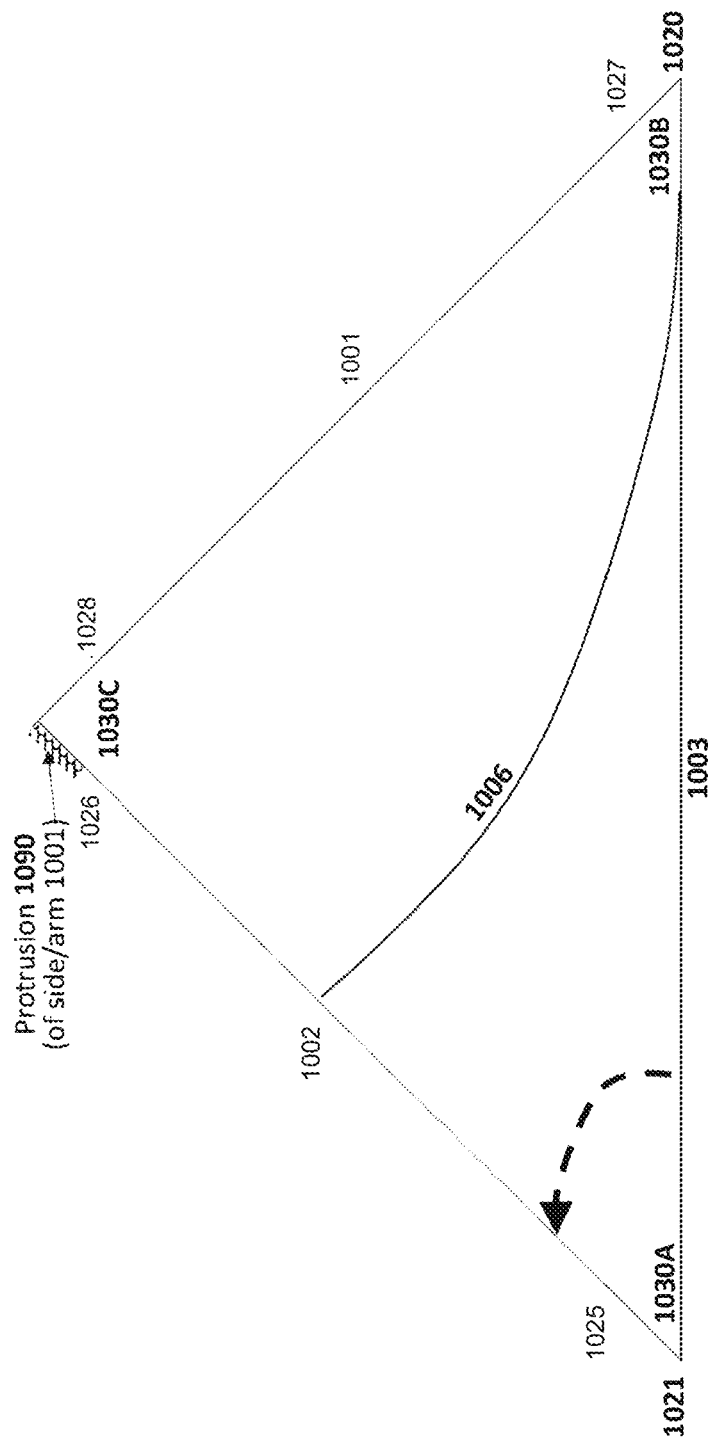
FIGS. 3A and 3B are simplified drawings of the gastric residence system of FIGS. 1A and 1B.

FIG. 3A corresponds to FIG. 1B and is a schematic drawing of the triangle. In FIG. 3A, a protrusion 1090 of arm 1001 is additionally illustrated. Arm 1002 acts against the protrusion 1090 when the device is biased into the expanded configuration. This facilitates retention of the device in the expanded configuration. This will be discussed in further detail below.

Transition of the device of FIGS. 1-3 from the compressed to the expanded state is now discussed with reference to FIGS. 4-5. FIG. 4A schematically illustrates the device of FIG. 1-3 in a compressed state.

Figure 3B:
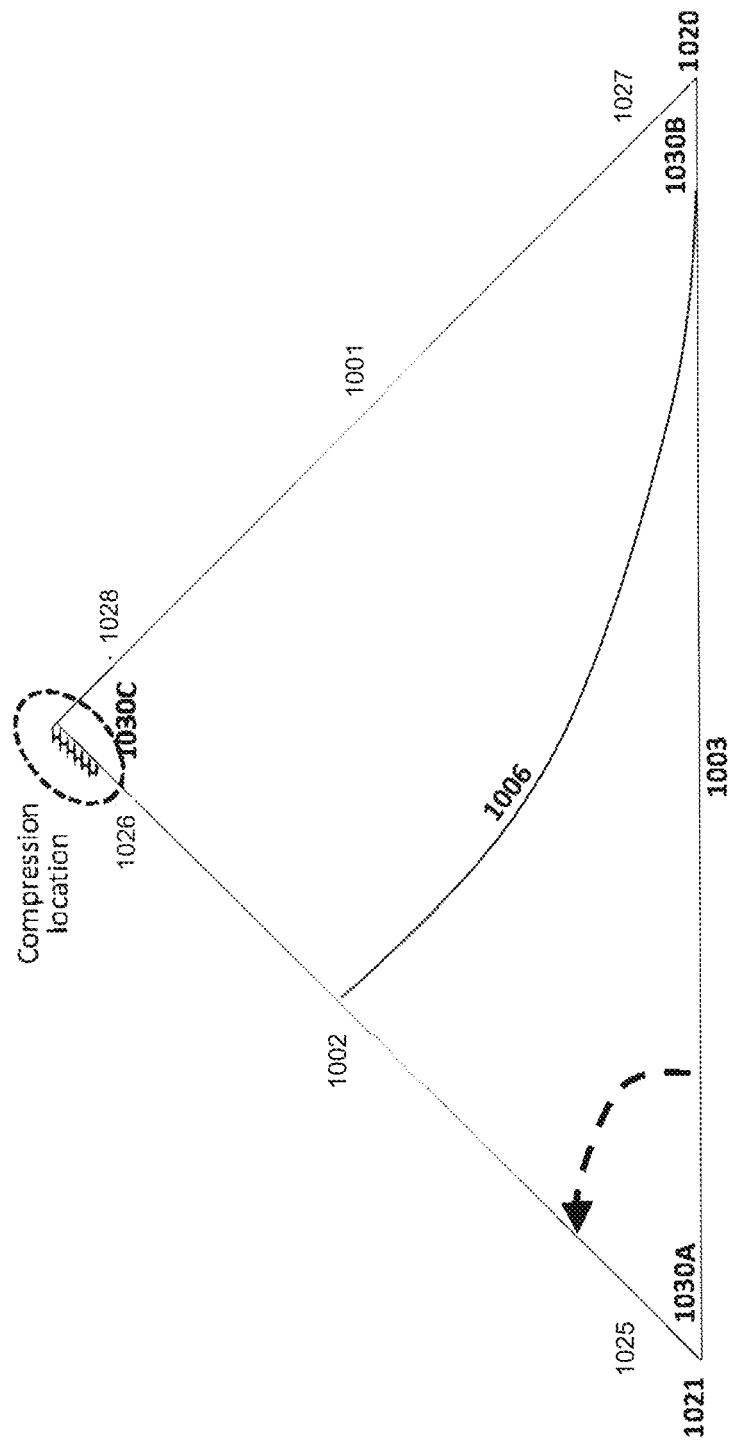
Figure 3C:
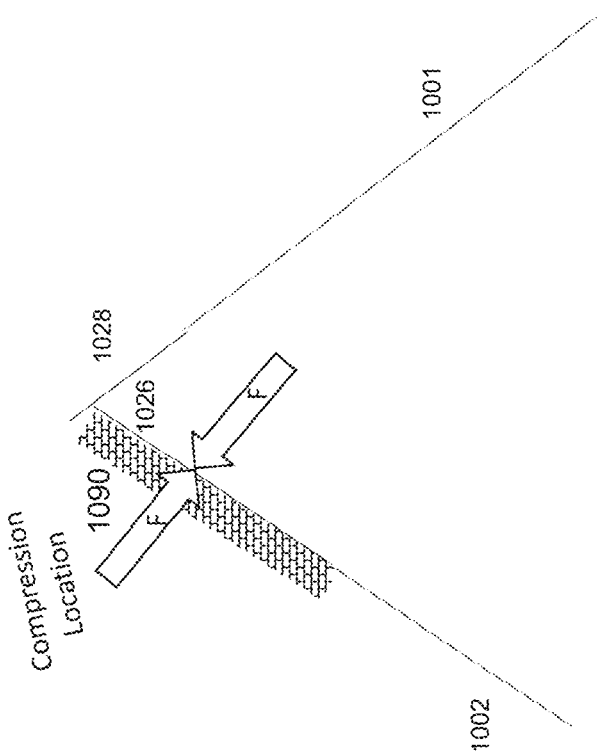
FIG. 3C is a simplified drawing of the hyphenated area in FIG. 3B.
Figure 4B:
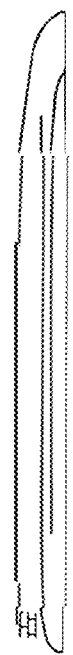
FIG. 4B is a simplified drawing of FIG. 4A.
Figure 4C:
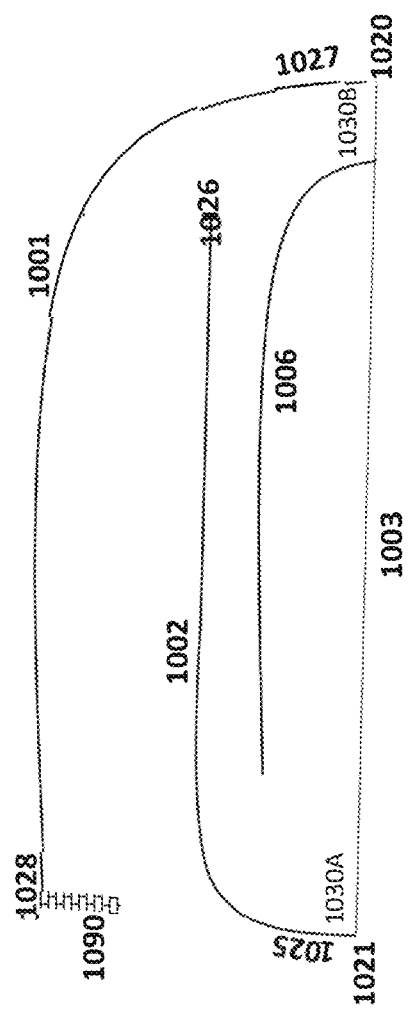
FIG. 4C is a vertically distorted version of FIG. 4B.
Figure 5:
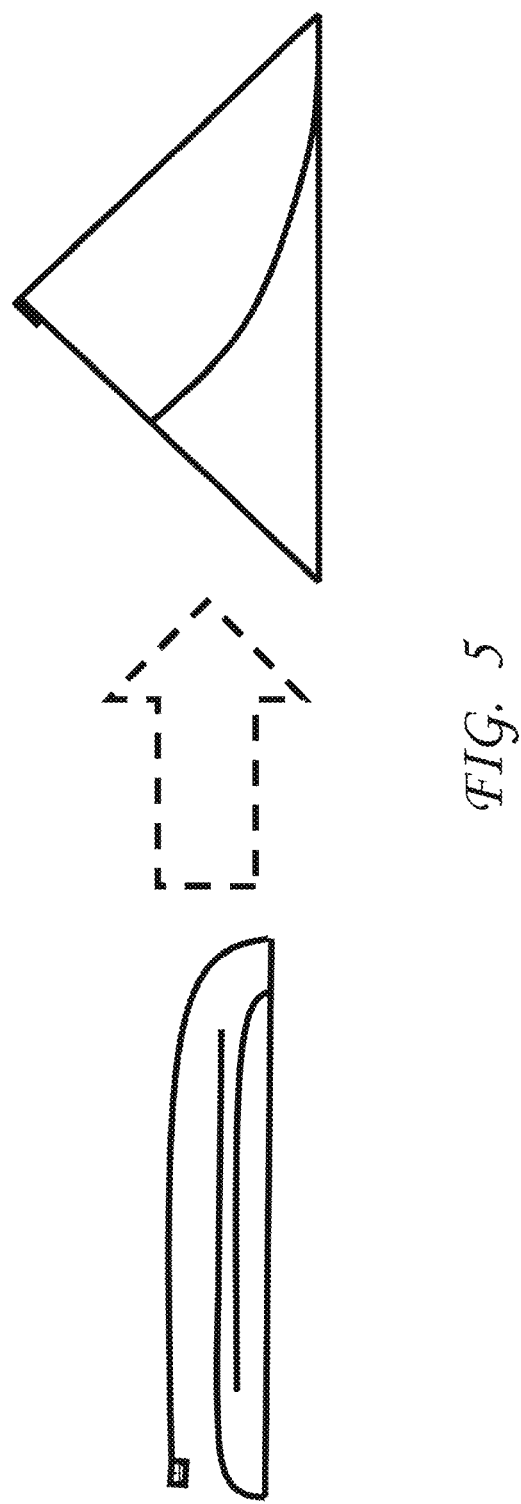
FIG. 5 is a simplified drawing of the transition of a gastric residence system from a compressed state to an expanded state.

FIG. 4B illustrates the collapsed or compressed-state schematically, in a manner similar to that of FIGS. 3A-3B which illustrates the expanded state schematically.

To better illustrate the various elements of FIG. 4B, FIG. 4C illustrates the same compressed state of FIGS. 4A-4B in a vertically distorted view where vertical space is 'stretched.'

Thus, as shown in FIG. 4B, when in the compressed state, vertex 1030C does not exist. As will be discussed below, vertex 1030C may be formed in situ (e.g. within the stomach) by pressure applied by leaf spring 1006 upon side 1002 (i.e. this pressure provides the torque around hinge assembly 1021).

For example, due to the presence of leaf spring 1006, the device is mechanically biased towards an expanded state. Before ingestion, this pressure may be counteracted by an erodible wrapper (e.g. retainer; around the device (e.g. of FIG. 4A). This wrapper or retainer can sustain the device in the compressed configuration of FIG. 4A-4C. However, upon ingestion and/or in the stomach, erosion of this wrapper or retainer reduces or eliminates this counteracting force, causing the device to transition from the compressed configuration to the expanded configuration as shown in FIG. 5.

The transition from the compressed configuration to the expanded configuration may be driven by elastic restoring forces—in the example of FIGS. 1-5 the restoring forces of leaf spring 1006. The transition may close a circuit (e.g. a polygon) and/or form a vertex (e.g. hinge less vertex) 1030C.

FIGS. 1-5 illustrate various elements of the system that may, in different embodiments, be useful for forming and/or sustaining vertex 1030C.

Figure 6:
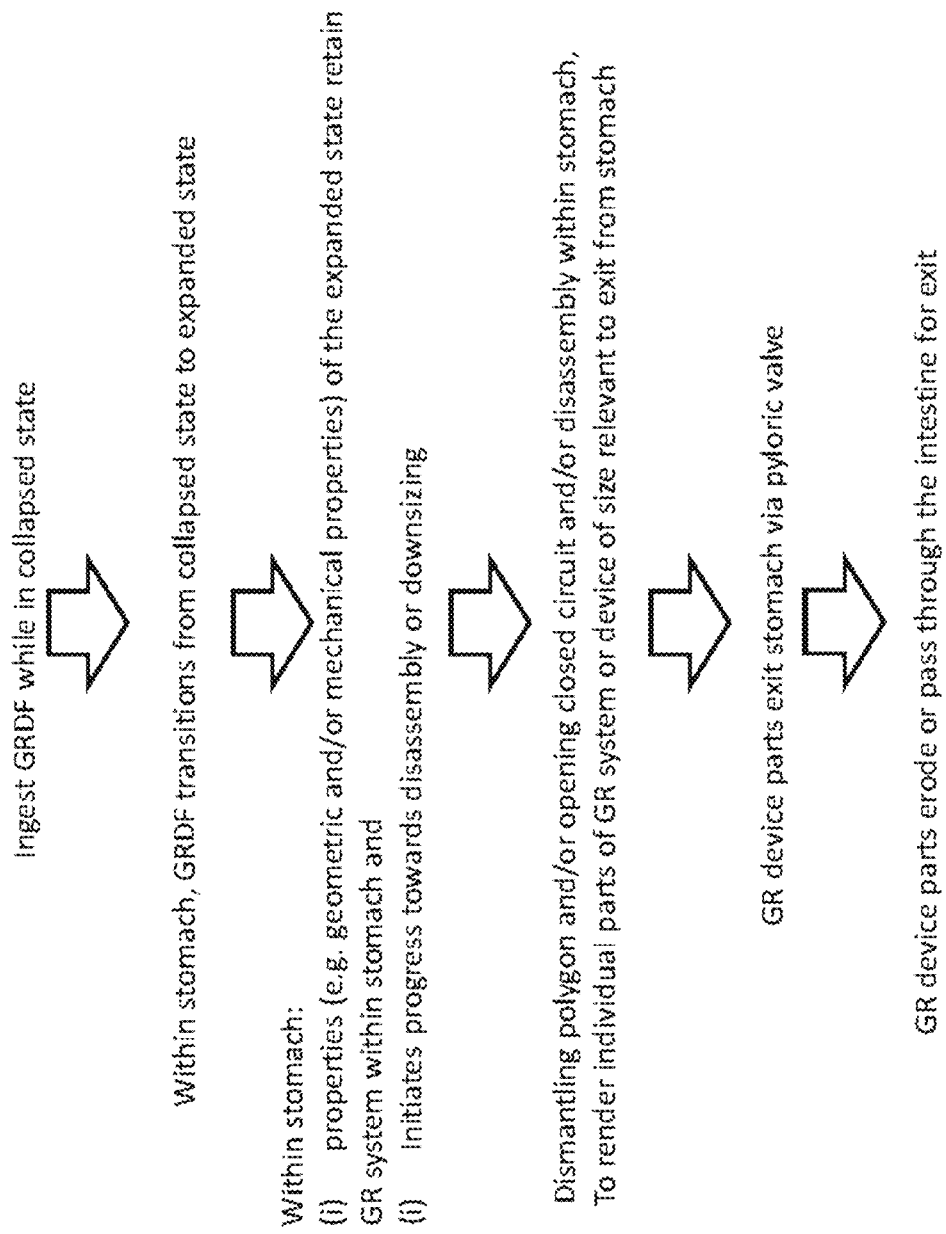
FIG. 6 is a flow chart of the process which a gastric residence system undergoes in use.
Figure 7B:
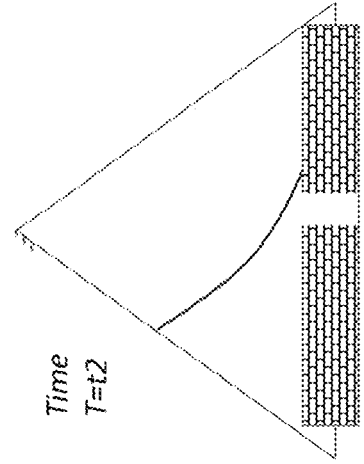
FIGS. 7A-7D illustrates a sequence of simplified drawings showing the change in the erodible insert within the gastric residence system of FIGS. 1A-1B over time.
Figure 7D:
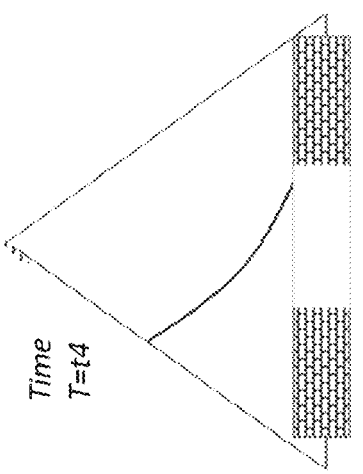
Figure 7A:
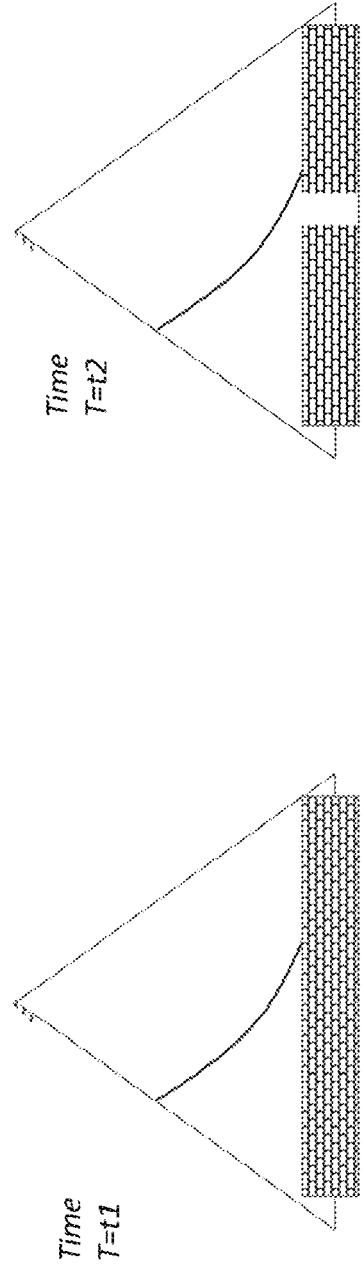
Figure 7C:
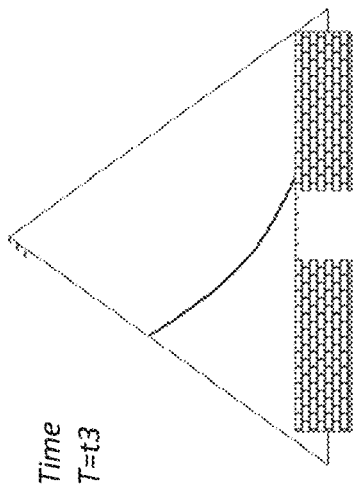

FIG. 6 is a flowchart of an extended-release method using any presently-described gastric retention system.

FIG. 7 illustrates the expanded state of the device and progressive erosion of the erodible in accordance with some embodiments. In particular, in some embodiments an erodible insert (e.g. tablet 1036) is present in mediating arm 1003—e.g. within a shell or sleeve having a window or opening 1007 via which gastric fluid may penetrate. In accordance with some embodiments, the erodible insert is in direct contact with an inner surface of mediating arm 1003.

The inner surface area of mediating arm 1003 can comprise at least 50% or at least 75% or at least 90% or at least 95% pH sensitive polymer. When an erodible insert is present in mediating arm 1003 the combination of the device and erodible insert is referred to as a gastric residence system.

Figure 8:
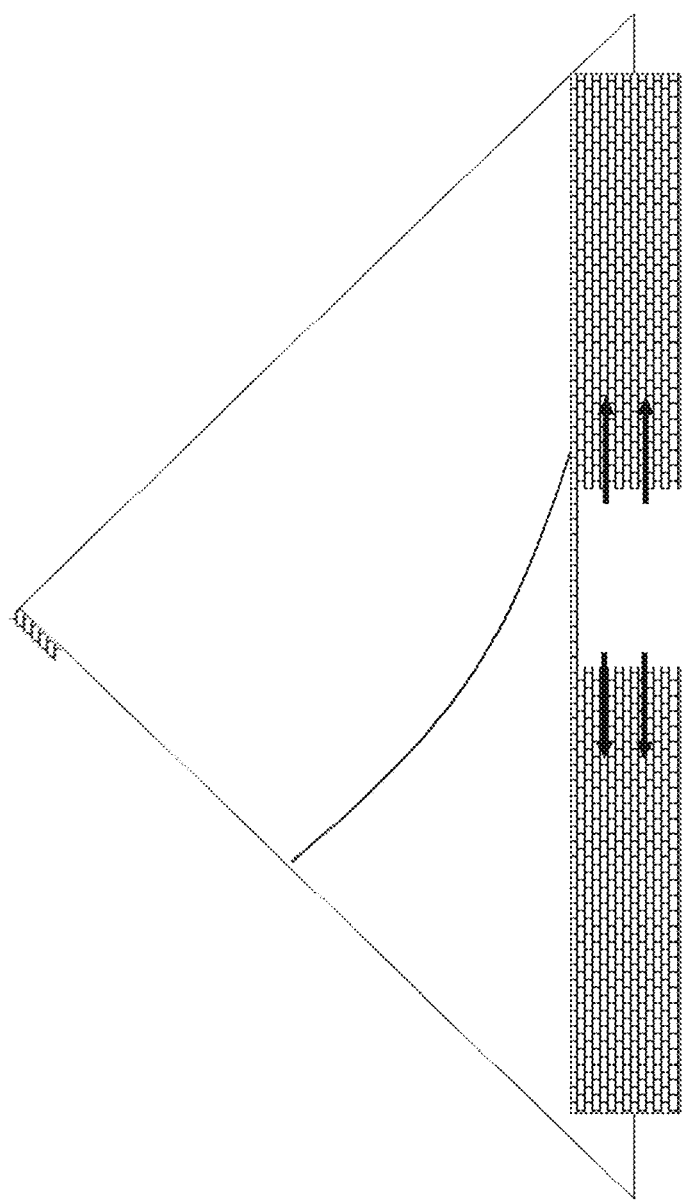
FIG. 8 is a simplified drawing of the gastric residence system of FIGS. 1A-1B in use.

At time t1 gastric fluid has yet to penetrate into an interior of arm 1003 where erodible insert 1036 is disposed. As noted above, in the example of FIGS. 1-5, an interior of arm 1003 is mostly sealed from the external environment (e.g. gastric fluids). Thus gastric fluid may only enter into the interior of arm 1003 via one or more window(s) or opening(s) 1007. In some examples, the window or opening 1007 is in a central portion of side/arm 1003. As such, and as illustrated in FIGS. 7 and 8, over time (e.g. at times t2, t3, t4) erosion of the erodible insert 1036 within arm 1003 is 'outward' erosion, e.g. from a central point in the arm in both directions towards arms 1002 and 1001 and hinge assemblies.

In some embodiments, erodible insert 1036 comprises a pharmaceutical—thus, the erosion illustrated in FIG. 7 is pharmaceutical-releasing erosion. Although erodible insert 1036 may comprise a pharmaceutical, any constitution may be envisioned whether uniform or in layers.

A presence of an erodible insert 1036 whether a unit (e.g. tablet) or series of inter-fitting units may maintain an attachment between hinge assembly 1020 or portion thereof and/or hinge assembly 1021 or portion thereof and arm 1003 (i.e. shell or gastric-juice-insoluble portions of the arms 1001, 1002, 1003). In this example, erosion of the erodible insert sufficiently modifies geometric and/or mechanical properties of insert 1036 (e.g. which is erodible) to detach a hinge assembly 1020 and/or hinge assembly 1021 from arm 1003. The modified geometric and/or mechanical properties of the erodible insert which result in detachment of a hinge assembly occur within an inner cavity of arm 1003. In this manner, the properties of the device remain substantially unaltered until disassembly.

As illustrated in FIG. 9, this detaching drives opening of the closed circuit or closed polygon and/or disassembly of the GRDF into units that are sized for exiting the stomach via the pyloric valve.

Further details of a specific example of a gastroretentive device, a gastric residence system incorporating a gastroretentive device as well as a gastroretentive dosage form of the present disclosure are described in detail below with respect to FIGS. 10-15.

FIG. 10 illustrates a front view of a gastroretentive device in an expanded configuration. The arrangement of this device is similar to that illustrated in FIG. 1.

The device illustrated in FIG. 10 includes three arms 2001, 2002 and 2003 in a similar manner to that illustrated in FIG. 1. The three arms 2001, 2002 and 2003 together form a body. The body is in the form of a generally triangular shape with arm 2003 as the base of the triangular shape and arms 2001 and 2002 as the sides of the triangular shape. Arms 2001 and 2002 are pivotally connected to the ends of arm 2003 thereby forming two apexes or vertices of the triangular shape. Arms 2001 and 2002 are mechanically engaged with one another to form the third apex or vertex of the triangular shape. The triangular shape may be any form of triangle, for example an isosceles triangle or an equilateral triangle. Due to the triangular arrangement of arms 2001, 2002 and 2003, the angle α or angle β between arms 2001 and 2003, and 2002 and 2003 can each be between about 30 degrees and 90 degrees and in some examples is around 60 degrees. For example, angle α and angle β may be about 60 degrees.

Although in the illustrated example a triangular shaped expanded configuration is illustrated, other shaped expanded configurations are also envisaged for example, circular (i.e. where arms have curvature), rectangular, rhombus or other quadrilateral shape, hexagonal, octagonal etc. Any suitable polygonal or circular shape may be used.

A biasing member in the form of a leaf spring mechanically biases arm 2002 thereby biasing the three arms 2001, 2002 and 2003 into the expanded configuration. This will be discussed in further detail below. Although in the illustrated example an elongate leaf spring 2006 is used as a biasing member, other suitable biasing arrangements may also be used. For example, a biasing member in the form of a helical spring and an elongate member may be used. Additional support for the biasing member may also be included such as an additional biasing member in the form of an elongate leaf spring 2006a to bias the elongate leaf spring 2006 and the 2001 arm. Alternatively the 2006r ramp which is configured to bias the elongate leaf spring 2006 from the first arm 2003 may provide additional support in transition.

Figure 19B:
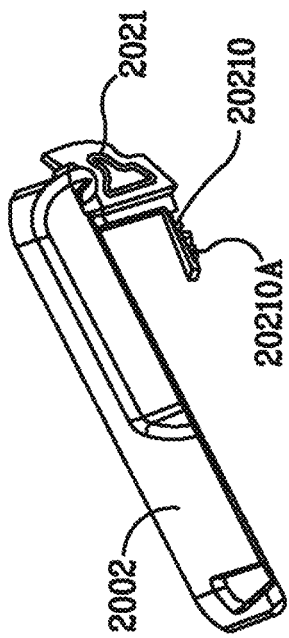
FIGS. 19A and 19B illustrate arms and hinge of the gastric residence system shown in FIG. 10.
Figure 19A:
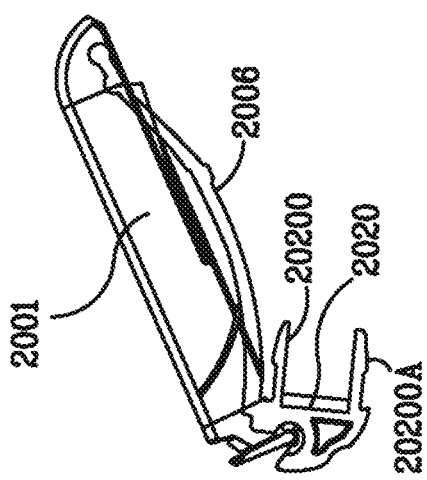
Figure 19D:
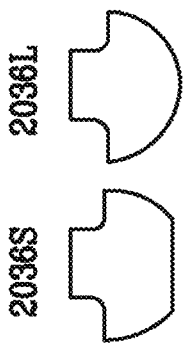
FIGS. 19C and 19D illustrate views of a sleeve of the gastric residence system shown in FIG. 10.
Figure 19C:
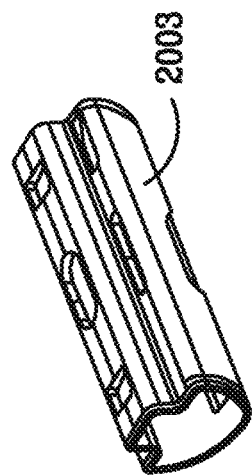

In the illustrated example, arm 2003 is in the form of a tube (See FIG. 19C). In this manner the interior of arm 2003 forms a cavity in which an erodible insert (See FIG. 19D) may be located. Plugs or sealing elements 2020 and 2021 are provided at the open ends of arm, sleeve or tube 2003 thereby sealing the ends of the tube. In the illustrated example, plugs 2020 and 2021 include hinge assemblies by which arm 2003 is pivotally connected to arms 2001 and 2002 respectively. One end of biasing member 2006 is attached to plug 2020. In the illustrated example the biasing member 2006 is integrally formed with plug 2020. In other examples, the biasing member 2006 may be separately formed and connected to plug 2020. In yet further examples, the biasing member 2006 may be attached to arm 2003 instead of plug 2020.

Since arm 2003 contains an erodible insert it may be considered a containing or loaded arm. In the illustrated example only one side or arm of the system is loaded with an erodible insert.

In the illustrated example, arms 2001 and 2002 are in the form of hollow half cylinders (See FIGS. 19A and 19B). Put another way arms 2001 and 2002 are in the form of cylinders that have been cut in half along their length. Arms 2001 and 2002 have a similar cross section to arm 2003 so as to correspond to arm 2003. In this manner, the three arms 2001, 2002 and 2003 can overlay one another when the system is compressed as will be discussed in further detail below. Arms 2001 and 2002 are hollow and therefore do not contain any erodible insert. The arms 2001 and 2002 provide structural support in order to provide the body with the required shape and structure in the expanded configuration. They may therefore be considered to be structural arms.

FIG. 11 is a cross-sectional view of the device of FIG. 10 and illustrates further details of the system. In the cross sectional view of FIG. 11 a cavity 2010 formed within arm 2003 can be seen more clearly. Opening 2007 is provided centrally at the base of arm 2003 in the illustrated example to provide access to cavity 2010 from the exterior of arm 2003. However the opening 2007 may be provided at any suitable location and can therefore be provided on an upper or side surface of arm 2003 and may be arranged at any point along the length or arm 2003. In the illustrated example only one opening is provided. However in other examples a plurality of openings may be provided to facilitate ingress of gastric fluid to the device. This will be discussed in more detail below.

Plugs 2020 and 2021 include retaining elements 20200 and 20210, respectively that extend into the interior or cavity 2010 of arm 2003. In the illustrated example each plug 2020 and 2021 includes two retaining elements 20200 and 20210, respectively. One retaining element extends from the top of each plug 2020 and 2021 and one retaining element extends from the bottom of each plug 2020 and 2021 such that when the plugs 2020 and 2021 are located in arm 2003, the retaining elements 20200 and 20210 act on upper and lower surfaces of the interior of arm 2003. However the present disclosure is not limited to this arrangement and the retaining elements can be arranged to extend into arm 2003 at the sides or at any suitable location around the interior of arm 2003. Additionally in the illustrated example two retaining elements are shown, however in other examples only one or alternatively more than two retaining elements can be provided. Any suitable number of retaining elements can be provided. The greater the number of retaining elements the more securely plugs 2020 and 2021 are held inside arm 2003 for extended periods of time under gastric conditions.

Retaining elements 20210 and 20200 include protrusions 20210a and 20200a, respectively, extending radially outward therefrom. The protrusions 20210a and 20200a are arranged to cooperate with corresponding recesses in the inner surface of arm 2003. Protrusions 20210a and 20200a include a shoulder against which an inner surface of the arm 2003 abuts. In this manner the retaining elements 20210 and 20200 prevent the plugs from falling out or being easily removed from arm 2003 and assist in retaining the plugs 2020 and 2021 in arm 2003.

With reference to FIG. 11, biasing member 2006 extends from a first end at, or proximal to, plug 2020, to a distal end at arm 2002. The distal end of biasing member 2006 engages with a protrusion on an inner surface of arm 2002. In the illustrated example three protrusions are provided adjacent to each other to provide three different locations for the biasing member to engage. In alternative examples arm 2002 is provided with only a single protrusion. In other alternative examples one or more recesses may be provided in which the biasing member can be located. By providing either a protrusion or recess against which the biasing member can locate, the biasing member 2006 can assist in retaining the device in the expanded configuration. However this may not provide the only means by which the device is retained in the expanded state. As such, in some examples, the biasing member 2006 does not engage with arm 2002 but simply abuts against it.

FIG. 11 further illustrates the engagement of arms 2001 and 2002 to form the third apex or vertex of the triangular shape of the system. As can be seen, an outer surface of arm 2002 engages with an inner or retaining surface of arm 2001. The force of the biasing member outwards, causes arm 2002 to be pushed against the interior of arm 2001. The outer end of arm 2001 encloses the outer end of arm 2002 thereby forming an apex or vertex. In this manner arms 2001 and 2002 are locked together thereby retaining the device in the expanded state. The mechanical engagement of the ends of arms 2001 and 2002 provides the main force for retaining the device in the expanded state and can therefore be seen as a locking or retention mechanism. Put another way, the free ends of arms 2001 and 2003 in the compressed configuration come into contact to provide a closed circuit in the expanded-state articulated body via a locking mechanism.

Further details of the locking or retention mechanism is illustrated in FIGS. 12A-12C. FIG. 12A illustrates the engagement of arms 2001 and 2002 when locked together. As illustrated, arm 2001 includes a tooth 2001a that protrudes therefrom. The tooth 2001a is tapered or in the form of a ramp although other shapes and configurations are also contemplated. Arm 2002 has a cut away portion or indentation 2002a formed on an outer surface thereof at the end of arm 2002 distal to arm 2003. The cut away portion 2002a and tooth 2001a cooperate with one another and provide a further means of mechanical engagement of arms 2001 and 2002 in addition to the mechanical engagement of the outer surface of arm 2002 with the inner surface of arm 2001 thereby providing additional retaining means, for example against a tangential force that may otherwise result in detachment. In some examples the tooth 2001a is not present and an edge or outer surface of arm 2001 cooperates with indentation 2002a. In other examples neither the indentation 2002a nor tooth 2001a are provided and the mechanical engagement of the ends of arms 2001 and 2002 provides sufficient force to retain the arms in the expanded state triangular shape.

As shown in FIG. 12C, plane 2001c contacts plane 2002c when a radial force F1 is applied externally. As shown in FIG. 12B, both planes 2001c and 2002c are angled such that the contact between the plane 2001c and the plane 2002c keeps arm 2001 locked with arm 2002.

In providing a means by which arms 2001 and 2002 are locked together in the expanded state, the device is provided with sufficient strength to enable it to be retained in the stomach and resist the forces applied by the stomach under both fed and fasted conditions. The mechanical strength afforded by the shape, interaction and engagement of arms 2001, 2002 and 2003 in the expanded configuration is sufficient to enable the preservation of the expanded configuration under gastric conditions. This assists in the provision of gastric retention since the expanded state of the device is sized so as to be too large to pass through the pyloric valve as will be discussed in further detail below.

FIG. 13 illustrates further features of arms 2001 and 2002. In the illustrated example, the indentation 2002a in arm 2002 engages with a rail or slider 2001b provided on arm 2001 as the device transitions into the expanded configuration. Rail 2001b is in the form of an elongate protrusion extending from arm 2001. Rail 2001b extends along the length of arm 2001 and is arranged to guide arm 2002 along arm 2001 into the locked configuration. This rail 2001b can be considered a guiding member. The provision of a guiding member keeps arm 2002 in the same plane as arm 2001 thereby facilitating the compression of the device into a compressed configuration or the expansion of the device into the expanded configuration.

FIGS. 14A and 14B illustrate the device in the compressed configuration. FIG. 14A is a front view of the device in the compressed configuration and FIG. 14B is a cross-sectional view of the device in the compressed configuration. As illustrated, arms 2001 and 2002 have been pivoted around to overlay arm 2003. The interior of arm 2002 has a corresponding shape to the exterior of arm 2003 and the interior of arm 2001 has a corresponding shape to the exterior of arm 2002. In the compressed position, arm 2002 overlays arm 2003 and arm 2001 overlays arm 2002. In this manner in the compressed state the arms 2001, 2002 and 2003 are provided one inside the other or nested together. This provides a compact arrangement that is easy for a patient to ingest for example when contained in a capsule or container.

As discussed above the gastroretentive device of the present disclosure is designed to be swallowed in a compressed configuration, expanded in the stomach, perform its intended function for a predetermined time period, and at the end of the time period or upon occurrence of a mechanical event, disassemble and/or disintegrate or preferably disassemble for eventual passage through the pyloric valve of the stomach. Thus it is important that the device can withstand the forces applied by the stomach and retain its shape and configuration in the expanded configuration so as to prevent unintentional disassembly into smaller components that would fit through the pyloric valve before expiry of the predetermined time period and/or before the device has finished performing its intended function. The device of the present disclosure is advantageously able to endure the significant forces applied to it under gastric conditions due to the particular size, shape and strength of the expanded state thereby enabling the device to perform its intended function for the required period of time. The device is further designed to disassemble into components small enough to pass through the pyloric valve once it has performed its function as will be discussed in further detail below.

In use, the device is typically provided in the expanded state due to the inherent bias of the biasing member although it may be administered in the compressed state. Before the device is administered to a patient, one or more active pharmaceuticals and/or diagnostics for delayed release are inserted into the device. The active pharmaceutical(s) or diagnostic(s) is typically in the form of an erodible insert that erodes or dissolves upon exposure to gastric fluid and is inserted into arm 2003. Thus the erodible insert is received in cavity 2010 of arm 2003. Put another way cavity 2010 houses or contains the erodible insert. In this manner arm 2003 protects the erodible insert from conditions external to the device. Once the erodible insert is located in the device, the erodible insert containing device is considered to be a gastric residence system.

The erodible insert degrades, erodes or changes its physical characteristics in a first set of physiological conditions of the gastric environment. In an aspect, the erodible insert is the only component that degrades, erodes or changes its physical characteristics in a first set of physiological conditions of the gastric environment. Thus erosion of the erodible insert does not cause degradation or erosion of arm 2003. Thus the mechanical strength of arm 2003 is maintained throughout erosion of the erodible insert. In some examples, the erodible insert can be configured to provide directional erosion for example from the center of the first arm towards the second and/or third arm(s). In this example, the erodible is housed or mechanically engaged with the sleeve or tube as well as the second and/or third arm or a pivotal connection or portion thereof. Thus, the erodible insert can provide a timed disconnection of the second and/or third arm which commences at greater than 60% erosion, at greater than 70% erosion, at greater than 80% erosion, at greater than 90% erosion or at greater than 95% erosion.

In the example illustrated in FIG. 15A the erodible insert fills the entirety of the cavity 2010 in arm 2003. In particular the erodible insert is sized such that plugs 2021 and 2020 have an interference fit between the erodible insert and the interior surface of arm 2003. The close fit of these components is such that the erodible insert provides an outward or compressive force which pushes resilient protrusions 20210a and 20200a into the recesses on the interior surface of arm 2003. This ensures that the plugs 2020 and 2021 remain located in the ends of arm 2003. In the illustrated example the erodible insert is in the form of one or more tablets.

Once the erodible insert has been inserted into the device thereby forming a gastric residence system, the system is compressed into the compressed state before ingestion. The system may be compressed by hand or using a machine or device similar to that described in WO2017/093976. After compression the system is retained in the compressed state by locating the system inside a capsule or container. The capsule has the additional function of preventing gastric fluid from entering opening 2007. The capsule is formed of material that is strong enough to withstand the inherent biasing force of the biasing member and thus retains the system in the compressed state. The capsule material also erodes or dissolves upon exposure to gastric fluid. Thus once the capsule is ingested by a patient, the capsule erodes in the presence of gastric fluid in the stomach. This removes the force retaining the system i.e. the device containing the erodible insert in the compressed configuration. The inherent bias of the biasing member then biases the device, and thus the overall system, into the expanded state where it is retained by means of the mechanical engagement of arms 2001 and 2002. Thus automatic transformation into the expanded configuration is achieved. The transformation of the system into the expanded configuration is independent of the erodible insert and therefore is solely dependent on the mechanical arrangement of the device. The device is designed such that the transformation from the compressed configuration to the expanded configuration occurs rapidly. In some examples the device is configured to transform between the compressed configuration for ingestion and the expanded configuration for gastric retention within less than 10 minutes, less than 5 minutes, less than 4 minutes, less than 3 minutes or preferably less than 2 minutes.

Once the GRDF has been ingested and travels to the stomach, the capsule has eroded and the system i.e. the device containing the erodible insert or alternative timed disassembly mechanism has transformed into the expanded state, the system remains in the stomach for a predetermined period of time. The system or more particularly the device from which the system is formed is thus sized so that in the expanded state, it cannot exit the stomach through the pyloric valve. In order to prevent passage through the pyloric valve, the device in the expanded state must have a minimum turning radius capable of resisting passage through the pyloric valve. "Turning radius" is understood to mean a critical dimension via which the system could be rotated and/or turned to fit through an opening, for example the pyloric valve, ring or a tube having a defined diameter and height. This is not necessarily the smallest dimension or diameter of the device but rather is a function of the 3D geometry of the device (depth, width, length of the device), the dimensions (for example radius r and height 30 mm) of the valve or simulated model thereof, and amount of space on either size of the valve. By providing a device of appropriate geometry, a gastric residence system that can remain in the stomach for a desired period of time is provided. For example, the minimum turning radius may be measured through rotation in any orientation in attempt to fit through a simulated model of pyloric valve (for e.g. a ring having a defined diameter).

In one example of the gastric retentive systems disclosed, there is provided an expanded state device having a smallest turning radius greater than about 20 mm or greater than about 22 mm or greater than about 24 mm or greater than about 25 mm or greater than about 26 mm. In another embodiment, gastric retention may be achieved with a device having smallest turning radius less than 35 mm or less than 32 mm or less than 30 mm or less than 28 mm. In other embodiments, gastric retention may be achieved with a device in expanded state, having smallest turning radius between 20 and 35 mm or about 20 mm to about 32 mm or between 20 and 30 mm or about 20 to about 28 mm or about 22 and 35 mm or about 22 mm to about 32 mm or between 22 and 30 mm or about 22 to about 28 mm or about 24 and 35 mm or about 24 mm to about 32 mm or between 24 and 30 mm or about 24 to about 28 mm or about 24 and 35 mm or about 24 mm to about 32 mm or between 24 and 30 mm or about 24 to about 28 mm or about 26 and 35 mm or about 26 mm to about 32 mm or between 26 and 30 mm or about 26 to about 28 mm or about 28 and 35 mm or about 28 mm to about 32 mm or between 28 and 30 mm. Combinations of the above-referenced ranges are also possible. The turning radius may be measured prior to exposure to gastric environment.

Another way of considering an appropriate size of the device is to consider the ratio between: (i) a minimum enclosing ring of the GRDF in the expanded state and (ii) a minimum enclosing ring of the GRDF in the compressed state. In examples of the device disclosed, the ratio is at least 1.5 or at least 2 or at least 2.5 and/or at most 10 or at most 7.5 or at most 5 or at most 4 or at most 3.5 or at most 3.0. Combinations of the above-referenced ranges are also possible.

Another way of considering an appropriate size of the devices disclosed herein is to consider a ratio between (i) the post-cleavage length of the mediating sleeve or tube and a (ii) a pre-cleavage and expanded-state diameter of a minimum-enclosing sphere of the device, is at least 0.05 or at least 0.1 or at least 0.2 or at least 0.3 or at least 0.5. Combinations of the above-referenced ranges are also possible.

Another way of considering an appropriate size of the device is to consider the convex hull volume. This term is known to those skilled in the art to refer to a set of surfaces defined by the periphery of a three-dimensional object such that the surfaces define a volume. In the present disclosure, appropriate size refers to a gastroretentive device large enough in the expanded configuration to prevent passage through the pyloric valve yet small enough in the compressed configuration to enable it to be swallowed. In order to meet these requirements it has been established that a convex hull volume of the compressed configuration is about 20 to about 40% or about 25 to about 35% or about 30% to about 40% of the convex hull volume of the expanded configuration. In order to meet these requirements it has been established that a convex hull volume of the expanded configuration is about 200 to about 400% or about 250 to about 350% or about 300% to about 400% of the convex hull volume of the compressed configuration. By providing a device with a smallest turning radius of about 20 to about 35 mm or about 22 mm to about 28 in an expanded configuration and/or a convex hull volume in a compressed configuration of about 30% of the expanded configuration convex hull volume, it is ensured that the device can be safely swallowed in its compressed configuration yet resistant to passage through the pyloric valve in the expanded configuration.

After a predetermined time in the stomach during which the pharmaceutical or diagnostic is released, the system disassembles into a number of smaller parts which are small enough to fit through the pyloric valve and pass out into the intestine and thence out of the body. The mechanism by which the device disassembles will now be discussed with reference to FIGS. 15A-15D.

FIG. 15A illustrates the system (i.e. the device containing the erodible insert) in the expanded state once the capsule retaining it in the compressed state has been eroded or dissolved. The dissolution of the capsule removes a cover over opening 2007 and thus allows gastric fluid to enter arm 2003 via opening 2007. The gastric fluid gradually dissolves or erodes the erodible insert 2036 thereby releasing the pharmaceutical or diagnostic. Once the erodible insert has eroded, the components of the device are each individually sized to exit the stomach.

FIG. 15B illustrates the system when the erodible insert 2036 is partially eroded. As can be seen in FIG. 15B since opening 2007 is centrally located in arm 2003, the erosion of the erodible insert 2036 is directional erosion from the center of the erodible insert 2036 outwards to the ends of the erodible insert 2036.

Referring to FIG. 15C, once the erodible insert 2036 has eroded or dissolved substantially, the outward force on the retaining elements 20210 and 20200 decreases. After a certain amount of erosion of the erodible insert 2036, the resilience of the retaining elements 20210 and 20200 which are biased inwards overcomes the compressive force of the erodible insert 2036 such that the resilient retaining elements 20200 and 20210 may retract out of the recesses in the arm 2003 by application of an external force. The protrusions are dimensioned such that once they are removed from the recesses in the arm 2003; the plugs 2020, 2021 are no longer retained in the arm 2003. Plugs 2020 and 2021 thereby disassemble from arm 2003.

Typically, the erodible insert is substantially eroded when at least about 60% of the erodible insert is eroded, or about at least about 70%, or about at least about 80% or about at least about 90% eroded before the compressive force of the erodible insert is reduced sufficiently to enable the retaining elements to retract out of the recesses in arm 2003. In other examples at least about 70%, at least about 80% or at least about 90% of the erodible insert must be eroded to enable disassembly of the system. The degree of erosion may correspond to the amount of pharmaceutical or diagnostic released.

Upon disassembly of plugs 2020 and 2021 from arm 2003, arms 2001 and 2002 also disassemble from another. FIG. 15D illustrates the components of the device after disassembly of the device. Each of the individual disassembled components may be small enough to pass through the pyloric valve into the intestines and thence out of the body. In alternative examples, the components may be further downsized for example by further disassembly or erosion so as to provide individual components small enough to pass through the pyloric valve.

Figure 16A:
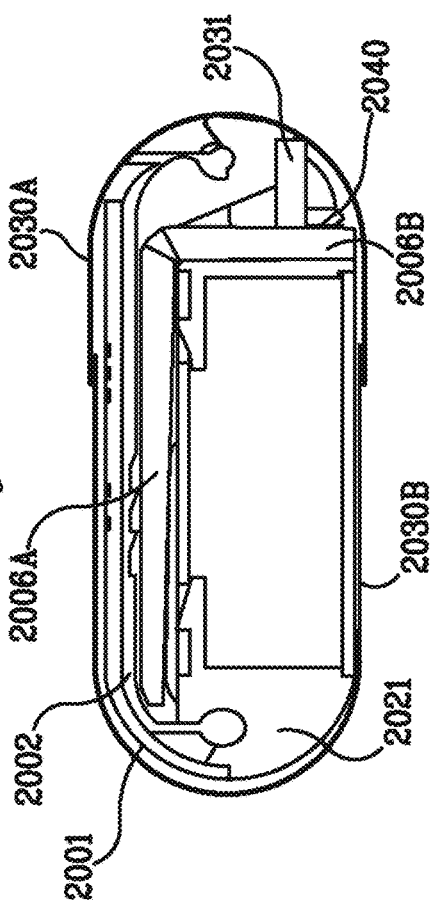
FIGS. 16A-16C are cross-section views of an alternative arrangement of a biasing element of the gastric residence system of FIG. 10.
Figure 16B:
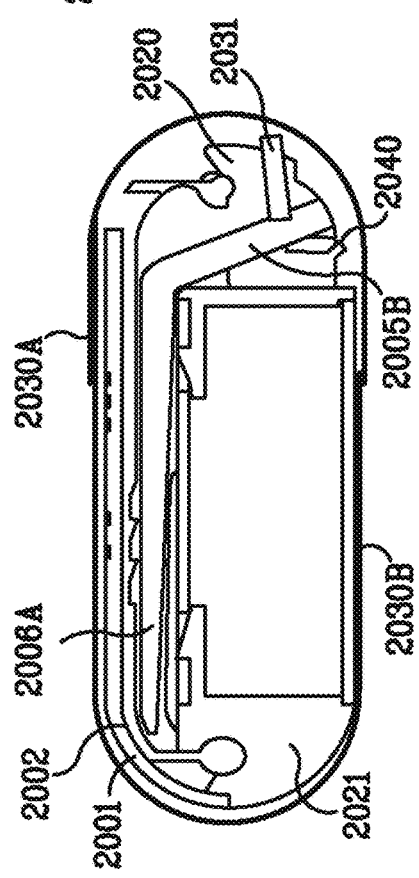
Figure 16C:
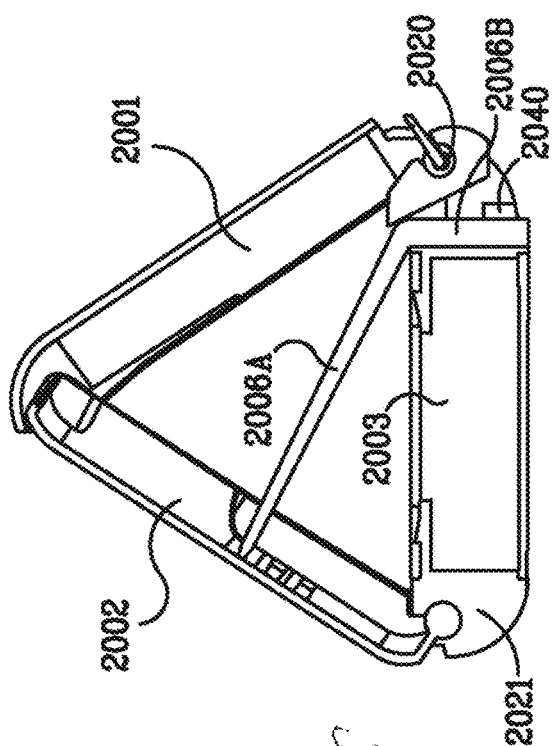

FIGS. 16A-16C illustrates an alternative configuration the device illustrated in FIGS. 10 and 14 in which the biasing member is an angled elongate member. This configuration is similar to the configuration illustrated in FIGS. 10-14 and therefore only the points of difference will be described.

In the compressed configuration a first portion 2006a of the biasing member extends over arm 2003 in a similar manner to the embodiment described with respect to FIGS. 1-15 above. A second portion 2006b of the biasing member is angled with respect to the first portion 2006a of the biasing member and extends into plug 2020.

When the device is compressed into the compressed state, the majority of the device is located in a main body 2030b of a capsule thereby retaining the device in the compressed configuration. As a closing portion 2030a of the capsule is inserted over the plug 2020 into which the second portion 2006b of the biasing member extends to close the capsule, a priming member 2031 extending from an interior of the closing portion 2030 pushes the second portion 2006b of the biasing member to a position perpendicular to the first portion 2006a of the biasing member as shown in FIG. 16B. The second portion 2006b of the biasing member is retained in position by a tooth 2040.

Upon erosion of the capsule in gastric conditions, the first portion of the biasing member 2006a acts on arm 2002 in a similar manner to the example described with respect to FIGS. 10 and 11 to force the system into the expanded configuration. FIG. 16C illustrates this alternative arrangement in the expanded configuration. Thus an alternative arrangement of the biasing member has been described which facilitates compression of the device and insertion into a capsule for ingestion.

Figure 17:
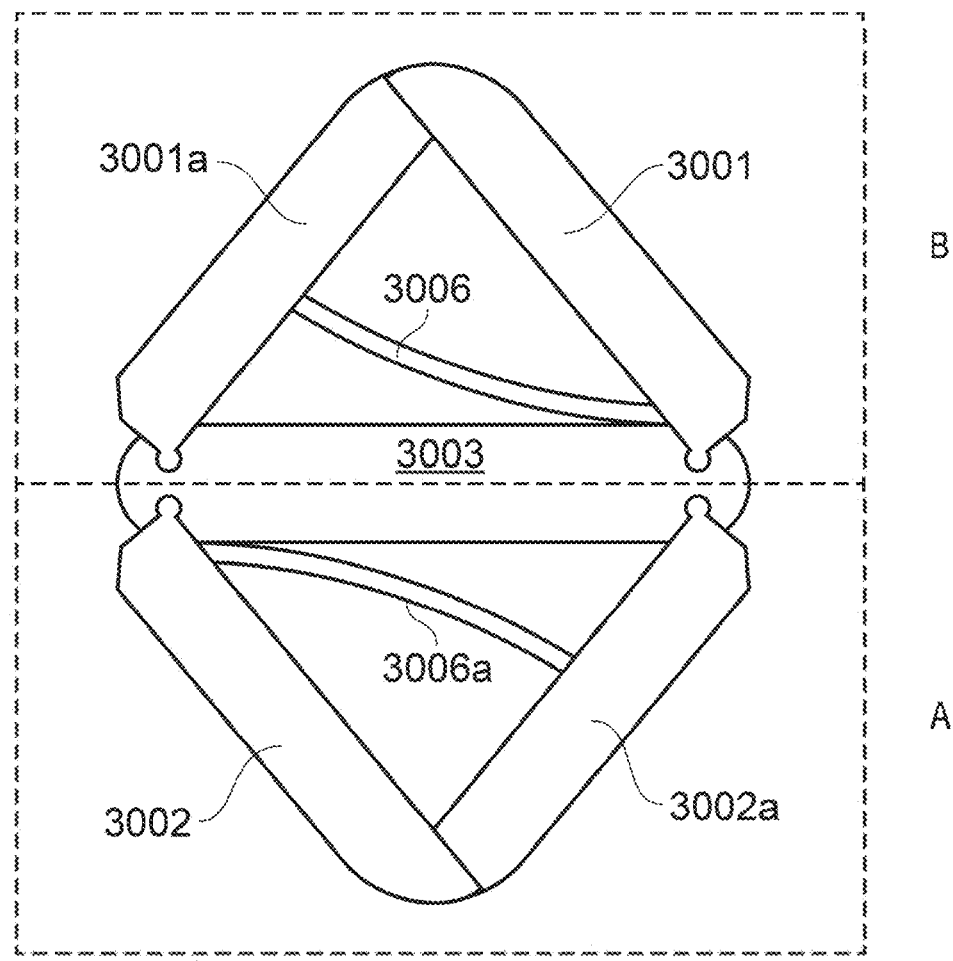
FIG. 17 is a front view of an alternative gastric residence system in an expanded configuration.

FIG. 17 illustrates a front view of alternative example of a gastroretentive device according to the present disclosure in an expanded configuration. This example is substantially similar to the examples described with respect to FIGS. 1-16 above and therefore only the points of difference will be described. In this example instead of two structural arms, four structural arms are provided. Arms 3001 and 3002 are provided on one side of containing arm 3003 and arms 3001a and 3002a are provided on the other side of containing arm 3003. A second biasing member 3006a is provided to bias arms 3001a and 3002a into an expanded configuration.

Arms 3001 and 3001a operate in the same manner and have the same features as arm 2001 in the example described with reference to FIGS. 10-16 above. Arms 3002 and 3002a operate in the same manner and have the same features as arm 2002 in the example described with reference to FIGS. 10-16 above. Thus arms 3001 and 3002 mechanically engage thereby locking arms 3001, 3002 and 3003 into a first triangular configuration. Similarly arms 3001a and 3002a mechanically engage thereby locking arms 3001a, 3002a and 3003 into a second triangular configuration. Thus the expanded configuration of this example includes two substantially triangular configurations, one either side of arm 3003.

Biasing members 3006 and 3006a operate in the same manner and have the same features as biasing member 2006 in the example described with reference to FIGS. 10-16 above. Biasing member 3006 biases arms 3001 and 3002 into the expanded configuration, while biasing member 3006a biases arms 3001a and 3002a into the expanded configuration. Thus in the expanded configuration the body has an overall quadrilateral shape that includes two generally triangular shaped sections A and B as illustrated.

When the device is compressed to a compressed configuration, arm 3001 overlays arm 3002 which itself overlays arm 3003 in a similar manner to arms 2001, 2002 and 2003 of the example described with respect to FIGS. 10-16 above. Similarly arm 3002a overlays arm 3001a which itself overlays arm 3003. Thus a compact compressed arrangement may be provided which facilitates oral administration.

This example thus provides an alternative arrangement of a gastroretentive device having the ability to transform between a compact compressed configuration and a strong expanded configuration that has the ability to withstand the harsh environment and gastric forces of the stomach.

In the example illustrated with respect to FIG. 17, each of arms 3001, 3002, 3001a and 3002a is straight. However as discussed above with respect to the examples illustrated in FIGS. 1-16, the present disclosure is not limited to this. Arms 3001, 3002, 3001a and 3002a could alternatively be curved. In another alternative example, arms 3001, 3002, 3001a and 3002a may be less rigid than those illustrated such that arms 3001, 3002, 3001a and 3002a may straight in the compressed configuration but slightly curved in the expanded configuration. In such an example the overall shape in the expanded configuration may be elliptical or substantially circular. It will be appreciated that a certain amount of rigidity must be maintained in order to provide a device of sufficient strength to be maintained in gastric conditions. However a device in which the mechanical engagement of arms 3001 and 3002; and 3001a and 3002a applies sufficient force to the arms to result in curvature of the arms is envisaged. Thus in the expanded configuration the device may have any overall shape provided it has the size and strength to withstand gastric conditions for a required period of time.

Thus examples of a gastric residence system that includes a gastroretentive device that can be retained in the stomach and disassemble after a predetermined time have been described with respect to FIGS. 1-17. In the above described examples, the length of time taken for the erodible insert to erode or dissolve acts as a timer for the disassembly of the system. In this manner the length of time the system can be retained in the stomach can be controlled by control of the erodible insert. For example, the erodible insert may be extremely resistant to erosion or dissolution so as to allow the system to be retained in the stomach for a long period of time. Alternatively the erodible insert may be less resistant to erosion or dissolution and thus the system may only be retained in the stomach for a short period of time. In some examples the erodible insert is a solid tablet. In such examples the erodible insert may be in the form of a plurality of tablets. In some examples each tablet may have the same rate of erosion/dissolution. In other examples the tablets nearest the opening may have a lower rate of erosion/ dissolution and the tablets adjacent the retaining elements may have a higher rate of erosion/dissolution.

Referring to FIGS. 10, 11, 15 the location of opening 2007 is a factor in determining the rate of erosion. For example, locating opening 2007 in the center of arm 2003 provides the maximum amount of erodible insert 2036 between the opening and retaining elements. Thus maximum erosion must be carried out before the retaining elements retract enabling disassembly of the device, thereby providing a maximum time delay before disassembly. Alternatively a plurality of openings may be provided at various locations on arm 2003 to increase the amount of gastric fluid entering the device and thereby increase the rate of erosion. Thus the length of time which the system is retained in the stomach may be controlled by the arrangements and size of openings in arm 2003 as well as the shape and rate of erosion under gastric conditions of the erodible insert 2036. These features are associated with the examples provided in FIGS. 1-9 and 17, as well.

In the illustrated examples, the erodible insert acts as a timer to delay the disassembly of the system until a predetermined time. However the invention is not limited to this example. Other means for delaying the disassembly of the system are also contemplated. For example a mechanical timer may be utilized and on expiry of a predetermined time period, retaining elements may be mechanically moved away from their corresponding recesses for example by an actuator in order to facilitate disassembly. In another example, heat sensitive or other externally triggered polymers may be employed and coupled with application of an external signal to the patient. It will be appreciated that other mechanisms which provide a timed disassembly are also contemplated. Thus the erodible insert can provide a disassembly function and/or dosage form providing function.

Referring generally to FIGS. 1-17, it should be understood that any method or mechanism that is configured to maintain the collapsed configuration of the gastric-retentive system prior to swallowing is envisioned. The examples described above include a capsule that erodes or dissolves upon contact with gastric fluid. In another envisioned example, in a case where the natural state of the gastroretentive system is the expanded state, there may be a material holding the gastroretentive system closed which dissolves or erodes in the presence of gastric fluid thereby releasing the gastroretentive system to an expanded configuration. In another example, the material may be in the shape of an erodible band which encompasses the arms to maintain the gastroretentive system in a collapsed configuration until the band erodes allowing expansion of the gastroretentive system. Still another envisioned example includes a glue-like material that keeps the two arms together until the glue-like material erodes allowing expansion of the gastroretentive system.

In the illustrated examples above, the capsule provides both a retention function for retaining the system in a compressed configuration and a barrier function by providing a cover over the opening to the cavity thereby preventing gastric fluid entering the cavity. In alternative examples however the barrier function and retention functions may be provided by separate components. For example the opening to the cavity could be sealed by a cover and the compressed configuration could be maintained by an erodible band. Alternatively an erodible cover could be provided over the opening to the cavity and a capsule provided to retain the system in the compressed configuration. In these examples the erosion rate of the cover may be different to the erosion rate of the capsule or band. In such examples the system may transform into the expanded configuration and gastric fluid would enter the cavity after a further time delay. In an alternative example, a further delay may be provided by a portion of the erodible insert or, where the erodible insert is formed from a number of erodible units, some of the erodible units may be positioned to erode first such that there is a delay in delivery of the API or diagnostic. Thus the provision of an additional cover for preventing gastric fluid entering the cavity can provide an additional delay in the delivery of the API or diagnostic and the disassembly of the system.

It should be understood that any method or mechanism that is configured to transition or open the gastroretentive device to the expanded configuration is encompassed by the present disclosure. In the examples described above a leaf spring springs outwards and extends from the inner area of one or both of the arms once the expanding configuration is initiated or once the mechanical integrity of the collapsed condition has been compromised, e.g., capsule 20 is dissolved. Alternatively a rigid member in combination with a helical spring could be used instead of the leaf spring. In an alternative envisioned example, a superporous hydrogel system may be incorporated into the inner part of the arm 2002 which expands upon exposure to the gastric environment thereby forcing arm 2002 upward against arm 2001 into the expanded configuration. In a further alternative example, the pivotal connection between arms 2003 and 2002 may be formed of an elastic material such that the pivotal connection itself biases the device into the expanded configuration.

As described in the examples, the mechanical engagement of arms 2001 and 2002 (or equally 1001 and 1002 or 3001 and 3002) by arm 2003 (or similarly 1003, 3003) locks the arms together into a triangular-shaped structure with the strength to withstand the forces that will act on it in the stomach and a size to prevent it passing through the pyloric valve and out of the stomach. In alternative embodiments, additional locking means may be employed to assist in locking the arms in an expanded configuration. For example, as described above, an inner facing surface of arm 2002 may include a locking mechanism to lock the leaf spring in place in the expanded configuration. Alternatively the hinge assemblies of the sealing elements or plugs may include one or more mechanical interfaces or mechanisms, gear, spring, cam, etc. that are configured to maintain or lock the gastroretentive device in the expanded configuration until disassembly. In some examples the leaf spring may simply be configured to bias the gastroretentive device from the collapsed configuration and not necessarily to maintain the gastroretentive device in the expanded configuration but may be configured to simply prevent the gastroretentive device from transitioning back to the collapsed configuration.

In the general area of unfolding gastric retentive systems, the force of opening or measure of mechanical bias towards an expanded state can be associated with a degree of safety risk in cases where unfolding or expansion occurs in an undesired location. Undesired locations include for example, the esophagus midway to stomach; in a crevice in the stomach wall or gastric rugae; or in intestine in cases where the capsule passes the pyloric valve prior to dissolving. Thus, it is of particular interest that in relation to the devices disclosed herein, in one embodiment, the force of opening from the compressed configuration is significantly less than the force to compressing the device from the expanded configuration. Put another way, the force of the biasing member acting to transition the device from the compressed configuration into the expanded configuration is significantly less than the force required to compress the device by about 10% in any dimension from the expanded configuration towards the compressed configuration. For example, the ratio of the opening force, applied by the biasing member, to the compression force, required to compress the device by about 10%, is less than about 0.2 or less than about 0.1 or less than about 0.05 or less than about 0.03 or less than about 0.02. In examples, the ratio is about 0.005 to about 0.2 or 0.005 to about 0.1 or about 0.005 to about 0.05 or about 0.005 to about 0.03 or about 0.005 to about 0.02. Combinations of the above-referenced ranges are also possible. In relation to the devices disclosed herein, the force to open from the compressed configuration towards the expanded configuration may be less than about 100 gF, or less than about 50 gF or between about 20 to about 30 gF.

In the examples discussed herein, a cylindrically shaped containment or mediating arm 1003, 2003 or 3003 is described however the containment arm may have any suitable shape that includes a cavity in which an erodible insert can be located. In a similar manner whilst particular shapes of structural arms 1001, 2001, 1002 and 2002 have been described, any suitable shape may be used provided the three arms can form a compressed configuration which is small enough to be swallowed. For example the structural arms may have a solid shape provided the depth of the arms is small enough to enable the device to compress to a suitable size and shape for swallowing. In alternative examples, the structural arms may have a hollow shape in the form of an open (i.e. not enclosed) shell in a similar manner to the specific examples described above. The structural and containment arms are not limited to any particular cross sectional shape however in examples where the structural arms are in the form of a shell, the arms are shaped so that an inner surface of structural arms 1001/2001 has a corresponding shape to an outer surface of structural arm 1002/2002; and an inner surface of structural arm 1002/2002 has a corresponding shape to an outer surface of containment arm 1003/2003. By forming structural arms 1001/2001 and 1002/2002 to have internal surfaces with corresponding shapes to structural arm 1002/2002 and containment arm 1003/2003 respectively, a compact device is provided that facilitates oral administration of the device.

As noted above, after a pre-determined period of time, the gastroretentive devices described herein will eventually lose their mechanical integrity as a single unit, disassemble and pass from the stomach for subsequent evacuation. There are many possible mechanisms to achieve this result, all of which are encompassed by the present disclosure. In the illustrated examples above an erodible insert is located in arm 2003 which disintegrates or erodes once exposed to gastric fluid thereby causing mechanical disengagement of the plugs 2020 and 2021 from arm 2003 and resulting in a dismantling of at least a first vertex. However the present disclosure is not limited to this example and further non-limiting examples include:

connection mechanisms between arms 2001, 2002 and 2003 composed of one or more time sensitive polymers which begin to disintegrate at a certain point in time.

connection mechanisms connected to arms 2001, 2002 and 2003 in a certain mechanical fashion, with a certain mechanical shape or by one or more mechanical features such that once the arms or insert erode via the introduction of gastric fluids, the mechanical integrity of the expanded state device (or parts thereof) is compromised due to a change of shape of one or more mechanical elements and, as a result, the mechanical engagement is lost combinations of a) and b).

The gastroretentive devices described herein include an arm having a cavity defined therein. The volume of the cavity may range from about 100 mm$^3$ to about 800 mm$^3$, about 300 mm$^3$ to about 600 mm$^3$ or about 350 mm$^3$ to about 550 mm$^3$. In embodiments, the volume of the cavity is about 0.8 ml to about 0.1 ml, or about 0.6 to about 0.3 ml.

In any of the gastroretentive systems described herein, the erodible insert can include excipients typically used for immediate release or controlled release. It should be understood that the functional effect of the controlled release or erosion of the insert tablet is obtained by the choice of excipients and surface area exposure to the gastric environment.

In some examples, one or more APIs or diagnostics for immediate or controlled release are associated with the gastroretentive system in a variety of ways, depending on the physical and chemical properties of the API or diagnostic and the desired release profile. In one example, the API/diagnostic is at least partially coated on the external wall of the cavity. In another example, the API or diagnostic may be at least partially enclosed within an external polymeric layer which forms the perimeter of the arm 2003 and which at least partially defines the interior cavity configured to hold an API/diagnostic and excipients. The API/diagnostic and excipients may be contained within the polymeric layer forming the cavity. The excipients may be any pharmaceutical excipients including, but not limited to, an erodible or non-erodible polymer matrix or may make up a constant-flow pump, which is for example mechanically or osmotically driven. As described above, the cavity may also have openings which contribute to a controlled release effect. In another example, the controlled release effect may be achieved by another method known in the art other than a polymeric layer forming a shell. In embodiments, the API may not be contained within an insert but rather may for example, be formulated to simply form part of the arm itself. Similar to the various embodiments described herein, the insert can be disengaged from the arms in any a number of different ways.

The materials are selected and processed in a way that will enable each of the components of the system to operate according to its defined functionality (e.g., rigidity for the arms and hinge, elasticity of spring, and stability in dissolution, as defined above) or desired manufacturing method (e.g. hot melt extrusion, injection molding). Different materials may be used in order to better balance between durability and safety or eventual disintegration; pH independence and dependence, etc. For example, the ratio of cellulose acetate (CA) to triacetin may contribute to the durability, elasticity, reduced brittleness, independence from pH changes and decreased erodibility. In another example, injection molded pH dependent polymer such as HPMC acetate succinate is at least partially coated with a pH dependent polymer (e.g., polymethacrylates such as HPMC acetate succinate, Eudragit S®). In another example, molded parts are a combination of pH independent and pH dependent polymer. Other materials may be selected from PCT/US2015/033850 or PCT/US2016/064439.

In some embodiment, the individual components excluding the wrapper and erodible such as the arms, hinge, tube or sleeve do not undergo any significant swelling in the presence of biological fluids such as blood, water, bile, gastric fluids, combinations of these, or the like. For example, in certain embodiments, the individual components swells by less than about 10 vol %, less than about 5 vol %, less than about 2 vol %, or less than about 1 vol % in a non-stirred, gastric fluid or simulated gastric fluid at physiological temperature as compared to the volume of the component in the dry state (e.g., RT). For example, the molded hinge assembly or arm component may comprise enteric polymers (i.e. for example included during injection molding) and/or a coat of enteric polymers (i.e. added post molding). In another embodiment, digestive track insoluble materials, for example cellulose acetate may be used.

The gastroretentive devices of the present disclosure may be manufactured by a number of processes including injection molding, 3D printing and the like, as will be clear to one skilled in the art, such as the manufacturing techniques described in WO 2003057197 or in Zema et. al., Journal of Controlled Release, Volume 159 (2012) 324-331. For example, a mold can be constructed in the desired shape of the components of the gastroretentive device and filled with appropriate material(s) in liquid state and then allowed to cure by chemical processes or cooled if thermosetting material(s) are used.

The ability to be minimally affected by a repetitive force contributes to the ability of a GR system to maintain a size relevant for gastric retention. In examples of the present disclosure, the gastroretentive devices described in detail above, may include a mechanical durability to remain intact, i.e., assembled with minimum deformation/downsizing when exposed to gastric conditions or when a repetitive compressive force is applied, over a period of time of at least about 2 hours, or about 3 hours, or about 6 hours, or about 9 hours, or about 12 hours or about 24 hours, or about 168 hours, or about one month, and under gastric conditions or when a repetitive force of at least 500 grF or at least 800 gF or at least 1000 gF or at least 2000 gF is applied. In the examples described above, the gastric retentive system is capable of substantially maintaining its size under application of at least about 500 gF, or at least about 600 gF, or at least about 700 gF or at least about 800 gF or at least about 1000 gF or about 2000 gF applied every two hours. In the examples disclosed herein, the gastroretentive device may include a mechanical durability to maintain a size relevant for gastric retention over a period of time of at least about 2, or at least about 3, or at least about 6, or at least about 9, or at least about 12 or about 24 hours and under the application of a repetitive force ranging from about 400 gF to about 3000 grF, in embodiments from about 400 gF to about 1000 gF. In the examples described above, the expanded state gastroretentive device is capable of resisting about 200 to about 600 gF over the full gastric retentive period. In another example, the gastric retentive devices or systems described in detail provide a mechanical durability to maintain a size relevant for gastric retention, i.e., assembled with minimal deformation/downsizing under the application of a repetitive force in any direction or position of at least about 500 gF or at least about 800 gF or at least about 1000 gF or at least about 2000 gF over a period of time of at least 2, 3, 6, 9, 12, 24, 48, 72 hours or up to a week, a month or up to a couple of months. In this context, minimal deformation/downsizing is considered about 20% or preferably about 10% change in largest dimension.

In the illustrated examples, the gastroretentive delivery system provides a gastric retentive endpoint and/or opening of the closed circuit and/or disassembly of the device and/or cleaving the connection between the erodible-insert containing arm and at least one of other arms. Changes in geometric and/or mechanical properties of the erodible opens the closed circuit and/or disassembles the body, rendering the body suitable for exiting the stomach via the gastric valve thereof. These each may be caused by release of active pharmaceutical ingredient of greater than 30%, greater than 40%, greater than 50%, greater than 60%, greater than 70%, greater than 80%, greater than 90% or greater than 95%.

In the examples described above, the expanded state gastroretentive delivery system is capable of maintaining dimensional strength and strength under repeated forces over a period of time in the gastric environment and/or until about more than 50%, 60%, 70%, 80% or 90% erosion of the erodible insert and/or until about 10%, 20%, 30%, 40%, 50%, 60%, 70%, 80%, 90% release of active ingredient. In some embodiments, the erosion of the erodible insert is at a rate similar to zero order preferably over 12 hours. Put another way the rate of erosion of the erodible insert is substantially constant.

In the examples described above, the expanded state gastroretentive delivery system is capable of being retained internal to a subject for extended periods of time beyond standard oral extended release dosage forms. In some embodiments, gastroretentive delivery system is capable of gastric retention under light meal conditions for at least 5 hours in 50% of subjects. In the examples described above, the expanded state gastroretentive delivery system is capable of gastric retention under light meal conditions for 5 hours in more than 50% of subjects. Assuming one can neutralize the effect of retention caused by the light meal, the gastroretentive delivery system is capable of retention through at least one or preferably two cycles of gastric housekeeping forces.

In the examples described above, the expanded state gastroretentive delivery system is capable of retention in a beagle dog stomach of at least 4.5 hours in about 50% of dogs under fasted conditions. In the examples described above, the expanded state gastroretentive delivery system is capable of retention in a beagle dog stomach of about 4 hours in at least about 50% of dogs.

In the examples described above, the expanded state gastroretentive delivery system is capable of gastric retention in a pig for about 1-2 days.

Optionally, in an additional example, any of the gastroretentive devices or gastric residence systems containing a gastroretentive device described or envisioned herein may include an emergency release feature that allows the gastroretentive device or system to pass through the pyloric valve for immediate removal from the stomach and gastrointestinal tract, if needed. An antidote or other triggering mechanism may be employed to initiate the emergency release of the gastroretentive device or gastric residence system. In one envisioned example, a gastroretentive device of the present disclosure includes plugs (or any other portion thereof) that are pH sensitive (for example sensitive to a pH 5-5.5) such that under normal gastric conditions the system (or any portion thereof) remains intact and the gastroretentive device functions as intended as part of a gastric residence system. However, if needed, the environmental pH can be slightly increased (to within the above pH sensitive range or any other specified range) causing the mechanical integrity of the plug (or any portion thereof) to erode causing the plug to disassemble from one or both arms and pass through the pyloric valve for subsequent evacuation.

EXPERIMENTAL EXAMPLES

Example 1

Manufacture of a Gastric Retentive System

Manufacture of a system as disclosed herein is described below, according to an aspect of this disclosure. The manufacture of device is described in FIGS. 1A-1C, erodible insert tablet in FIG. 1D, labeling in FIG. 1E for the purposes of the preclinical and human studies described and assembly in FIG. 1F Example 1A Manufacture of Extruded Beads The extruded beads were prepared using hot melt extrusion technology.

"Formulation N": cellulose acetate (400 g) and triacetine (100 grams)

"Formulation B": HPMC AS HG (1600 grams), HPMC AS MG (400 grams), PEG 3350 (44 grams) and dibutyl sebacate (176 grams)

Each of Formulation N and Formulation B were blended in a high shear mixer (DIOSNA P-25). The granules are then fed in twin-screw extruder (screw diameter 16 mm) at the rate of 1 kg/hr, screw speed of 150 RPM, melt temperature of 190° C. for Formulation N and 140° C. for Formulation B. The extrudate was cooled using air cooled conveyors and chopped into beads using a Varicut Pelletiser.

Example 1B

Mold Manufacture

Molds of each of the gastroretentive device parts were designed for use in injection molding technology. Extruded beads were fed into a Wittman EcoPower 55 Ton Injection Molding Machine using injection parameters listed in Table 1. The obtained parts are illustrated in FIGS. 10 through 15 and FIGS. 19A-19C.

TABLE 1

Injection molding parameters

| Part Injected [shown in FIGS. 10-15 and FIG. 19A-19 C] | Barrel Temperature [° C.] | Mold Temperature [° C.] | Injection pressure [Bar] | Hold pressure [Bar] | Cycle time [sec] |
|---|---|---|---|---|---|
| Hinge assembly 2021 (Formulation N) | 170-215 | 65 | 1600 | 550 | 16-13 |
| Hinge assembly 2020 (Formulation N) | 170-220 | 65 | 1600 | 550 | 16-13 |
| Ramp 2006r (Formulation N) | 170-220 | 65 | 1600 | 700 | 16-13 |
| Arms 2001, 2002 (Formulation B) | 150-190 | 55-40 | 1400 | 750-700 | 23-18 |
| Arm sleeve, tube 2003 (Formulation B) | 150-190 | 60-40 | 2000 | 780-700 | 23-18 |

Example 1C

Mold Coating

The arms 2001, 2002 and 2003 were coated using an O'Hara LabCoat 15" machine. The dispersion formulation is presented in Table 2. The parts were coated using the following parameters: inlet temperature of 30° C., exhaust temperature of 25° C., atomizing air pressure of 1.5 bars, spray rate of 7-10 g/min and pan speed of 14-18 RPM. A coating weight gain of 5.0% was applied to the parts. Curing step was done for half an hour at inlet temperature of 40° C.

TABLE 2

Enteric coating formulation.

| Component | Quantity [g] |
|---|---|
| Dibutyl Sebacate | 27 |
| Ferric oxid red | 8 |
| Talc extra fine | 52 |
| Eudragit ® S-100 (Methacrylic Acid copolymer, Type B) | 312 |
| Isopropyl Alcohol | 3480 |
| Acetone | 870 |

Example 1D

Erodible Insert Tablet Manufacturing

Erodible 2036 is made up of two types of tablets for a total of four unit: two side tablets (2036S, FIG. 19D) for inclusion at either end of the sleeve or tube 2003 and two central tablets (2036L, FIG. 19D) placed in the center between the side tablets. Each punch was designed to fill the cavity of the device. The tablets were produced using wet granulation.

The formulation of the central tablets and side tablets are presented in Table 3. The intra-granular excipients were mixed in high shear mixer (Diosna P-10). The granulation solution (purified water) was added to the high shear mixer during mixing. The obtained granulate was then dried using a fluid bed drier (FBD), milled using milling machine (Quadro 0.032") and blended together with the extra-granular excipients using blender (Y-cone 5L). The final blend was compressed into tablets using Fette 102 (each central tab weighed 220 mg and each side tablet weighed 160 mg).

TABLE 3

Tablet formulation

| | Quantity [g] | |
|---|---|---|
| Component | Side tablet (2036S) | Central tablet (2036L) |
| Intra-granular materials | | |
| Povidone (PVP K-90) | 156.8 | 276.0 |
| Mannitol USP (PEARLITOL ® 200SD) | 9.5 | 412.8 |
| Barium Sulfate USP | 1237.5 | 1237.2 |
| Ethocel ™ Premium 7 CPS | 668.3 | 408.0 |
| Granulation solution (purified water)* | 210 | 210 |
| Extra-granular materials | | |
| Mannitol USP (PEARLITOL ® 200SD) | 255.1 | 277.2 |
| Magnesium Stearate | 25.8 | 28.8 |

*evaporated during drying

Example 1E

Mold Labelling

The 2001, 2003, 2020, 2021 were manually labelled with Barium sulphate for detection in X-ray. Barium sulphate were manually placed on the 2001, 2020, 2021 and 2003 (about 20-25 mg for each part) and then sealed using a cellulose acetate solution 6.5% W/V in acetone.

All labeled parts were then dried at room temperature.

Example 1F

Assembly of GRS, FIG. 10

The ramp 2006r was added to the 2003 sleeve using the cellulose acetate solution described in Example 1G. Arms 2001 and 2002 were lubricated using Magnesium stearate powder. The insert erodible tablets 2036 were placed in the 2003 sleeve in the following order: one 2036S on each end and two 2036L in the centre. Hinges 2020 and 2021 were then manually connected to respective arms 2001 and 2002. The final gastric retentive system was stored in HDPE bottles with silica until dosing. Before in vivo dosing or in vitro testing, assembled GRDF were folded and placed in a capsule 000, elongated to 29 mm.

Example 2

In Vitro Characteristics, FIG. 20

For the purposes of this example, in order to disassociate the effects of the erodible, the hinges 2020 and 2021 were glued to opposing ends of the 2003 arm [FIG. 10].

For the purposes of this example, the opening force is the minimum force applied by the device to open from the compressed configuration, as illustrated as F1 in FIGS. 20A and 20B. In order to measure the minimum opening force, F1, the minimum weight applied at W on the compressed structure (which was placed on a rigid surface), which resulted in slight opening was measured for both a comparative example and the test article described above, see FIGS. 20A, 20B Results are presented in Table 4.

For the purposes of this example, the rigidity of a device is a measure of a device's ability to resist change despite application of a force of compression, F2 in FIGS. 20C and 20D. F2 is calculated by measuring the minimum force which is applied for 30 seconds and which is required to cause a 10% decrease in the height of the expanded state gastric retentive at room temperature. Four systems were tested and results are presented in Table 4.

Comparative device B: GRS in FIG. 20A and FIG. 20C* (addition details of device design in PCT/US2015/033850, example 6—FIG. 18, 34B), using material from Formulation B Comparative device N: GRS in FIG. 20A and FIG. 20C* (addition details of device design in PCT/US2015/033850, example 6—FIG. 18, 34B), using material from, using material from Formulation N GRS B: GRS of Example 1—Formulation B
GRS N: GRS of Example 1—Formulation N

TABLE 4

Results:

| Force | Gastroretentive System tested | | | |
|---|---|---|---|---|
| | Comparative device B | Comparative device N | RS B | RS N |
| Opening force F1 (grF) as measured by sensor | 180 | 285 | 0 | 0 |
| Rigidity as measured by minimum Force F2 required to cause > 10% in height against (grF) as measured by sensor | 700 | 850 | 500 | 000 |
| Ratio of F1/F2: | 0.257 | 0.335 | .012 | .013 |

*= Additional details can be found in PCT/US2015/033850, example 6 (FIGS. 18, 34B)

Example 3

Beagle Dog Study

Protocol

Five Beagle dogs [12-15 kg] were enrolled in the study. All animals were evaluated over 3 days of repeat, sedated dosing after overnight fasting. The test article as described in Example 1 was endoscopically dosed directly to the stomach cavity. Immediately following dosing, ~80 ml of water (room temp) was administered via the endoscope directly to the stomach cavity. Approximately 5 minutes later, dosing fluoroscopy was performed to evaluate GRDF location and condition (open or closed). If the GRDF had not opened, an additional fluoroscopy evaluation was performed at ~15 minutes post-dosing. The following fluoroscopy follow up schedule was employed after the first and final dosing: 4 h, 8 h, 12 h, 24 h, 36 h and 48 h for a total of 5 days±2 days following the final dosing or until the test sample left the stomach cavity. Approximately 5 hours following a dose, the animals were fed a ~150 kcal meal. Prior to fasting, for a minimum of 12 hours, the animals were provided a meal of at least ~300 kcal or normal PM rations if exceeding 300 kcal.

On ~Day 7 the animals underwent final fluoroscopy imaging.

Safety Results:

All animals were generally healthy throughout the duration of the study without gastrointestinal irritation and/or injury observed in the GI. There was no premature emptying of encapsulated test product from the stomach. Fecal Occult Blood Test (FOBT) was negative prior to and at end of the study. Feces was collected at least once a day, and the collected feces was examined for remnants of the test article; which were assessed for the physical state and then photographed, collected, and returned to the Sponsor after the end of the study. No abnormal feces were noted. The biodegradable components of the test article were noted to be very soft or almost completely eroded.

Results:

TABLE 5

Results of Dog Study

| Parameter | Dogs |
|---|---|
| Meal condition | Fasted |
| % Gastric retentive system expanded and assembled in stomach | 50% (5/10) at 4 hr** <br> 0% (0/10) at 8-36 hr |
| Premature emptying from stomach into the intestine of expanded form | None |
| % Gastric retentive system disassembled in GI (prior to exiting animal) | 50% (5/10) at 4 hr** <br> 60% (6/10) at 8 hr <br> 33% (5/15) at 12 hr <br> 13% (2/15) at 24 hr <br> 10% (1/10) at 36 hr |

*based on 2 or 3 doses

Example 4

Pig Study

Protocol

Twelve Yorkshire pigs were divided into two treatment groups, test and control, with a total of 6 animals (3 male, 3 female) evaluated over 5 days of repeat, sedated dosing after overnight fasting. The test article as described in Example 1 was dosed via gastric tube directly to the stomach cavity. Immediately following dosing, ~200-250 ml water (room temperature) was administered via the gastric tube directly to the stomach cavity. Approximately 5 minutes later, the dosing fluoroscopy was performed to evaluate device location and condition (open or closed). The fluoroscopy follow up schedule was employed after the first and final dosing: 4 h, 8 h, 12 h, 24 h (immediately following 2nd dose), 36 h, and 48 h (immediately following 3rd dose). Approximately 5 hours after a dose, the animals were fed normal AM feed rations. Prior to fasting, for a minimum of 12 hours, the animals were provided with normal PM feed rations.

Feces monitoring and collection occurred at least twice daily during the in-life duration. Collected feces were examined for test article remnants, and continued until either all remnants were recovered or the animal was terminated.

On ~Day 7 the animals underwent final fluoroscopy imaging and euthanized for a complete necropsy. Tissues were collected for further histological analysis.

TABLE 6

Results of Pig Study

| Parameter | Pigs |
|---|---|
| Meal condition | Fasted |
| % Gastric retentive system expanded and assembled in stomach | 100% (6/6) at 4-36 hr* <br> 83% (5/6) at 48 hr |
| Premature emptying from stomach into intestine of expanded form | None |
| % Gastric retentive system disassembled in GI (prior to exiting animal) | 0% (0/6) at 4-36 hr* <br> 17% (1/6) at 48 hr |

*based on first dose

Example 5

Human Study

A single center, single dose, two-cohort, open-label study was approved by the IRB and conducted according to GCP with informed healthy subjects (males and females, aged 50-70 years, total n=12). Cohort 1 (n=4) went through a single period under light meal condition, Cohort 2 (n=8) had a randomized 2-period, 2-way-cross-over design with 2 different meal conditions (i.e. light and moderate meal).

After an overnight fast of >10 hrs, subjects had to complete either a light caloric breakfast (130 kcal, 21% fat) within 20 min or a moderate caloric breakfast (552 kcal, 48% fat) within 45 min, depending on the respective Cohort/Period. Immediately after breakfast (at 20 or 45 min after start of light or moderate fat breakfast, respectively), a single dose of the test product described in Example 1 was administered orally to each subject with a glass of water.

In light meal test arm, a lunch (500 kcal) and a dinner were served at 5 hrs and 10 hrs post dose (herein "pd"), respectively. In periods under moderate meal conditions, a lunch (862 kcal) and a dinner were served at 4 hrs and 10 hrs pd, respectively.

Serial X-Ray Imaging and/or Fluoroscopy Scans were performed pd to confirm and document anatomical location and state of test product X-ray images were conducted with a fluoroscopy device at 0.167, 5, 8, and 10 hrs pd. Fluoroscopy only was performed at 4, 7 and additionally at 15 hrs pd if gastric retention (GR) was demonstrated at 10 hrs pd.

Results

Capabilities of expanded and assembled test product:

The number of subjects with test product in expanded and assembled state in stomach and intestine are shown in TABLE 7.

Figure 18B:
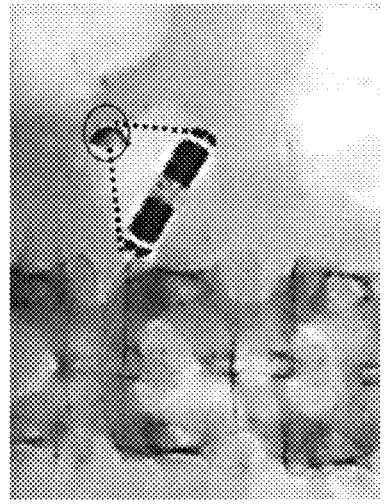
FIGS. 18A-18C are x-ray imaging photographs of an exemplary residence structure according to one example in the GI of a human subject.
Figure 18C:
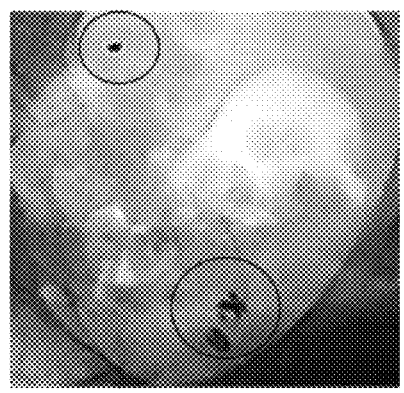
Figure 18A:
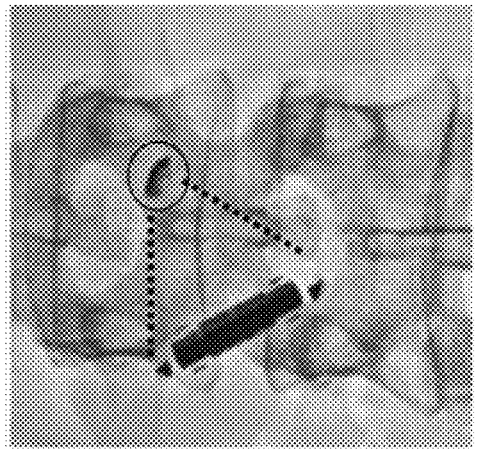

The test products, in expanded and assembled state, were capable of enduring the conditions of healthy subjects' stomach under different meal conditions after a single dose. FIG. 18 is a series of x-ray imaging photographs taken after 10 minutes (FIG. 18A), 4 hours (FIG. 18B), and 24 hours (FIG. 18C) post swallow.

TABLE 7

Results of Human Study

| | Number of subjects with assembled or downsized test product over time | | | |
|---|---|---|---|---|
| | Light meal condition [n = 12] | | Moderate meal condition [n = 8] | |
| Time point | Expanded state test product in stomach | Expanded state test product in intestine | Expanded state test product in stomach | Expanded state test product in intestine |
| 10 min | 12 | 0 | 8 | 0 |
| 4 hrs | 6 | 1 | 3 | 1 |
| 5 hrs | 6 | 1 | 3 | 1 |
| 7 hrs | 4 | 1 | 1 | 1 |
| 8 hrs | 3 | 0 | 1 | 1 |
| 10 hrs | 2 | 0 | 1 | 1 |
| 15 hrs | 1 | 0 | 1 | 1 |

Safety and tolerability after a single dose to healthy subjects were acceptable and no serious adverse events occurred. All GR systems eventually downsized for safe passage through the downstream intestinal tract.

Thus a device for extended retention in a human stomach having improved gastric retention over previously known devices has been described. In some examples the device includes a first arm comprising a first end and a second opposing end, a second arm and a third arm, the second and third arms being pivotally connected to respective ends of the first arm, wherein the device is configured to transform between a compressed configuration and an expanded configuration, the device further comprising a biasing member configured to bias the device into the expanded configuration; wherein in the expanded configuration the second and third arms are configured to mechanically engage each other to retain the device in the expanded configuration.

Put another way a device for extended retention in a human stomach has been described that can transform between a compressed configuration and an expanded configuration wherein in the expanded configuration the device has a smallest turning radius of greater than 20 mm or between 20-28 mm and is able to withstand forces in every orientation of greater than 250 gF or greater than 400 gF or greater than 600 gF at whether immediately upon expansion of a period of greater than 4 hours or 6 hours or 12 hours or 24 hours up to a couple of months in a human stomach or simulated model. Thus, a device with improved size and strength and therefore gastric retention capabilities in the expanded configuration has been described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The following numbered clauses define various further aspects and features of the present technique:

1. A GRDF comprising:
an articulated body having a collapsed state for ingestion and an expanded state for retention in the stomach, the expanded-state body defining a closed polygon, first and second hinges being respectively disposed at first and second vertices of the polygon and attached to each other via a mediating arm or side of the polygon, the polygon further comprising a third vertex, wherein the body includes, houses, holds or is mechanically engaged to a erodible so that erosion of the erodible disconnects the mediating side from at least the one hinge or such that upon disconnection, the polygon is dismantled so as to separate units of the body from each other, each of the units sized for exit from the stomach via the pyloric valve.

2. The GRDF of clause 1 wherein the erodible is a pharmaceutical-containing erodible and the erosion which disconnects the mediating side from the at least one hinge is pharmaceutical-releasing erosion.

3. The GRDF of any preceding clause wherein the body is mechanically biased towards the expanded state by an elastic restoring force.

4. The GRDF of any preceding clause, wherein the articulated body is mechanically biased towards the expanded state by a biasing element.

5. The GRDF of any preceding clause, wherein the biasing element is external to all hinges and/or external to all vertices of the body.

6. The GRDF of any preceding clause, further comprising a gastric-fluid-erodible wrapper/covering for maintaining the articulated body in a collapsed state against the outward bias of the body.

7. The GRDF of clause 6, wherein upon exposure to gastric fluid, the GRDF transitions from the collapsed state to the expanded state, the transition from the collapsed to the expanded state commencing with erosion of the gastric-fluid-erodible wrapper.

8. The GRDF of any preceding clause wherein the additional vertex is hinge less.

9. The GRDF of any preceding clause, wherein maintenance of the third vertex is dependent upon sustained application of a torque around at least one of the hinges and/or upon a sustained compressive force between constitutive sides of the third vertex.

10. The GRDF of any preceding clause, wherein the articulated body is mechanically biased towards the expanded state, and the mechanical bias maintains the additional vertex.

11. The GRDF of any preceding clause, wherein the transition from the collapsed to the expanded state connects two free and/or distal ends of arms or sides of the articulated body to form the closed polygon.

12. The GRDF of any preceding clause, wherein at least 50% or at least 75% or at least 90% or at least 95% of an area of an outer surface of the articulated body is gastric-fluid-insoluble.

13. The GRDF of any preceding clause wherein gastric-fluid-insoluble comprises a pH-insensitive polymer.

14. The GRDF of the preceding clause wherein the pH insensitive polymer is a non-ionic cellulose ester.

15. The GRDF of the preceding clause wherein the non-ionic cellulose ester is cellulose acetate.

16. The GRDF of any proceeding clause, wherein the mediating side comprises an inner surface in direct contact with the erodible.

17. The GRDF of the preceding clause wherein the inner surface comprises a pH sensitive polymer.

18. The GRDF of the preceding clause wherein at least 50% or at least 75% or at least 90% or at least 95% of an area of the inner surface of the mediating side is a pH sensitive polymer 19. The GRDF of the preceding clause wherein the pH insensitive polymer is HPMS-AS HG, MG or LG.

20. The GRDF of any preceding clause, wherein the closed polygon is a triangle.

21. The GRDF of any preceding clause, wherein the closed polygon is an N-gon where N is a positive integer greater than 3.

22. The GRDF of any preceding clause, wherein the first and second vertices are adjacent vertices.

23. The GRDF of any preceding clause, wherein the expanded state the GRDF structure provides gastric retention of at least 6 hours or at least 12 hours or at least 18 hours or at least 24 hours or at least 2 days or at least 3 days or at last 1 week or at least 2 weeks or at least 1 month.

24. The GRDF of clause of any preceding clause wherein disconnection of the mediating side from the first and/or second hinge dismantles the third vertex.

25. The GRDF of any preceding clause wherein the body is mechanically biased towards the
expanded state by an elastic restoring force and the third vertex is maintained by the elastic restoring force.

26. The GRDF of any preceding clause wherein the third vertex is maintained by a compressive force between constitutive sides of the third vertex, and disconnection of the mediating side from the first and/or second hinge causes the compressive force to cease and the third vertex to be dismantled.

27. The GRDF of clause 26 wherein the body is elastically biased towards the expanded state by an elastic restoring force, and the compressive force between the constitutive sides is provided by the elastic restoring force.

28. The GRDF of any preceding clause wherein the erodible contains an active pharmaceutical in the form of a tablet.

29. The GRDF of any preceding clause wherein changes in geometric and/or mechanical properties of the erodible disconnects the mediating side from at least the first hinge.

30. The GRDF of any of the preceding clauses, wherein disconnection of the mediating side from at least the one hinge is dependent on erosion of the tablet.

31. The GRDF of any preceding clause where the disconnection commences at greater than 60% erosion, at greater than 70% erosion at greater than 80% erosion at greater than 90% erosion at greater than 95% erosion at 99% or 100% erosion 32. The GRDF of any preceding clause wherein the tablet is loaded in an interior of a shell or sleeve having a gastric-fluid-insoluble outer surface.

33. A method for extended release comprising:
orally administering a collapsed state GRDF comprising a mediating side and at least a first hinge (such as of any one of clauses 1-32);
transitioning of the GRDF from the collapsed state to the expanded state for gastric retention;
erosion of the erodible to disconnect the mediating side from at least the first hinge;
dismantling the expanded state GRDF (for example polygon) to partially or fully separate units; and
exiting partially or fully separate units of the GRDF from the stomach via the pyloric valve.

34. The method of clause 33 wherein the erodible is pharmaceutical-containing erodible and the erosion which disconnects is pharmaceutical-releasing erosion.

35. A GRDF comprising:
an articulated body having a collapsed state for ingestion and an expanded state for retention in the stomach, the expanded-state body defining a closed polygon defining a plurality of vertices, wherein the body includes, holds, houses or is mechanically engaged to a erodible so that when the erodible is exposed to gastric fluid, erosion of the erodible dismantles at least a first of the vertices.

36. The GRDF of clause 35 wherein the erodible is a pharmaceutical-containing erodible and the erosion which dismantles at least a first of the vertices is pharmaceutical-releasing erosion.

37. The GRDF of any preceding clause wherein changes in geometric and/or mechanical properties of the erodible dismantles at least a first of the vertices 38. The GRDF of any of the preceding clauses, wherein dismantles at least a first of the vertices is dependent on erosion of the tablet.

39. The GRDF of any preceding clause where the dismantling of at least a first of the vertices commences at greater than 60% erosion, at greater than 70% erosion at greater than 80% erosion at greater than 90% erosion at greater than 95% erosion at 99% or 100% erosion.

40. The GRDF of any preceding clause wherein the dismantling of the first vertex triggers a dismantling of a second of the vertices, thereby disassembling the closed polygon into a plurality of units, each unit being sized for exit from the stomach via the pyloric valve.

41. The GRDF of any preceding clause wherein the second vertex is maintained by a compression between constitutive sides thereof, the dismantling of the first vertex eliminates the compression, thereby dismantling the second vertex.

42. The GRDF of clause 41 wherein the body is mechanically biased to the expanded state by a biasing force which drives the compression.

43. An extended release method comprising:
a. orally administering the collapsed state GRDF of any one of clauses 35-42;
wherein upon entering the stomach, the GRDF transitions from the collapsed state to the expanded state for gastric retention;
subsequently and within the stomach, pharmaceutical-releasing erosion of the erodible dismantles a first of the vertices to drive opening of the closed polygon and/or disassembly of the body into units, thereby rendering the body suitable for exiting the stomach via the pyloric valve; and
subsequently, the GDRF exits the stomach via the pyloric valve.

44. The method of any extended release method disclosed herein, wherein the gastric release of the pharmaceutical dosage proceeds for at least 6 hours or at least 12 hours or at least 18 hours or at least 24 hours or at least 2 days or at least 3 days or at last 1 week or at least 2 weeks or at least 1 month.

45. The method of clause 44, wherein an elapsed time from disconnection of the mediating side from the first hinge and the exit of the units or whatever is at most 3 hours or at most 2 hours or at most 1 hour or at most 30 minutes 46. A GRDF comprising:
an articulated body having a collapsed state for ingestion and an expanded state for retention in the stomach, the body biased towards the expanded state, the collapsed-state articulated body having first and second ends, optionally free ends, the expanded-state-articulated body defining a closed circuit which does not exist when the articulated body is in the collapsed state, the body including, housing, holding, protecting or being mechanically engaged to a erodible; and
a gastric-fluid-erodible wrapper for maintaining the body in a compressed state against the mechanical bias of the body,
wherein exposure of the GRDF to gastric fluid:
i. sufficiently erodes the wrapper so as to transition the body from the collapsed state to the expanded state so that upon transition, the first and second free ends are brought into contact with each other to form the closed circuit,
ii. subsequently, erosion of the erodible opens the closed circuit, optionally located at a vertex for exit from the stomach via the pyloric valve and/or dissembles the articulated body for exit from the stomach via the pyloric valve.

47. The GRDF of clause 46 wherein the erodible is a pharmaceutical-containing erodible and the erosion which, opens the closed circuit for exit from the stomach via the pyloric valve and/or dissembles the articulated body for exit from the stomach via the pyloric valve, is pharmaceutical-releasing erosion.

48. The GRDF of any preceding clause wherein changes in geometric and/or mechanical properties of the erodible opens the closed circuit for exit from the stomach via the pyloric valve and/or dissembles the articulated body for exit from the stomach via the pyloric valve.

49. The GRDF of any of the preceding clauses, wherein the opening of the closed circuit for exit from the stomach via the pyloric valve and/or disassembly of the articulated body for exit from the stomach via the pyloric valve is dependent on erosion of the tablet.

50. The GRDF of any preceding clause where the disconnection of the opening of the closed circuit for exit from the stomach via the pyloric valve and/or disassembly of the articulated body for exit from the stomach via the pyloric valve commences at greater than 60% erosion, at greater than 70% erosion at greater than 80% erosion at greater than 90% erosion at greater than 95% erosion at 99% or 100% erosion.

51. The GRDF of any of preceding clause, wherein the closed circuit is a closed polygon.

52. An extended-release method comprising:
orally administering the collapsed state GRDF of any of clauses 46-51;
upon entering the stomach, fluids therein sufficiently erodes the wrapper so as to transition the body from the collapsed state to the expanded state so that upon transition, the first and second ends are brought into contact with each other to form the closed circuit;
subsequently, erosion of the erodible by gastric conditions within the stomach opens the closed circuit and/or disassembles the articulated body for exit from the stomach;
subsequently, the body exits the stomach via the pyloric valve.

53. An extended-release method comprising:
orally administering the collapsed state GRDF of any of clauses 46-51;
upon entering the stomach, fluids therein sufficiently erodes the wrapper so as to transition the body from the collapsed state to the expanded state so that upon transition, the first and second ends are brought into contact with each other to form the closed circuit;
subsequently, pharmaceutical-releasing erosion of the erodible by gastric conditions within the stomach opens the closed circuit and/or disassembles the articulated body for exit from the stomach;
subsequently, the body exits the stomach via the pyloric valve.

54. The method of any of clauses 52-53 wherein before opening or disassembly, the GRDF is retained in the stomach for at least 6 hours or at least 12 hours or at least 18 hours or at least 24 hours or at least 2 days or at least 3 days or at last 1 week or at least 2 weeks or at least 1 month.

55. The method of clause 54 wherein an elapsed time between
(i) the opening and/or disassembly and
(ii) the exit of the body via the pyloric valve, is at most 3 hours or at most 2 hours or at most 1 hour or at most 30 minutes.

56. A GRDF comprising:
an articulated body having a collapsed state for ingestion and an expanded state for retention in the stomach, the expanded-state-articulated body defining a closed circuit,
the body including, housing, holding, protecting or being mechanically engaged to a erodible;
wherein when the body is exposed to the erodible, erosion of the erodible opens the closed circuit and/or disassembles the body, rendering the body suitable for exiting the stomach via the gastric valve thereof.

57. The GRDF of clause 56, wherein the erodible is a pharmaceutical-containing erodible and the erosion which, opens the closed circuit and/or disassembles the body, rendering the body suitable for exiting the stomach via the gastric valve thereof, is pharmaceutical-releasing erosion.

58. The GRDF of any preceding clause wherein changes in geometric and/or mechanical properties of the erodible opens the closed circuit and/or disassembles the body, rendering the body suitable for exiting the stomach via the gastric valve thereof 59. The GRDF of any of the preceding clauses, wherein the opening the closed circuit and/or disassembles the body, rendering the body suitable for exiting the stomach via the gastric valve thereof is dependent on erosion of the tablet.

60. The GRDF of any preceding clause where the opening the closed circuit and/or disassembles the body commences at greater than 60% erosion, at greater than 70% erosion at greater than 80% erosion at greater than 90% erosion at greater than 95% erosion at 99% or 100% erosion.

61. The GRDF of any preceding clause wherein the closed circuit is a closed polygon.

62. An extended-release method comprising:
orally administering the collapsed state GRDF of any of clauses 56-61;
upon entering the stomach, the body transitions into the expanded state and is retained within the stomach;
subsequently, erosion of the erodible by gastric conditions within the stomach cleaves the closed circuit and/or disassembles the body, rendering the body suitable for exiting the stomach via the gastric valve thereof;
subsequently, the post-cleaving body exits the stomach, whole or in pieces, via the pyloric valve.

63. An extended-release method comprising:
orally administering the collapsed state GRDF of any of clauses 56-61;
upon entering the stomach, the body transitions into the expanded state and is retained within the stomach;
subsequently, pharmaceutical-releasing erosion of the erodible by gastric conditions within the stomach cleaves the closed circuit and/or disassembles the body, rendering the body suitable for exiting the stomach via the gastric valve thereof;
subsequently, the post-cleaving body exits the stomach, whole or in pieces, via the pyloric valve.

64. The method of any one of clauses 62-63 wherein before cleaving, the GRDF is retained in the stomach for at least 6 hours or at least 12 hours or at least 18 hours or at least 24 hours or at least 2 days or at least 3 days or at last 1 week or at least 2 weeks or at least 1 month.

65. The method of clause 64 wherein an elapsed time between (i) the cleaving and (ii) the exit of the body via the pyloric valve, is at most 3 hours or at most 2 hours or at most 1 hour or at most 30 minutes.

66. A GRDF comprising:
an articulated body having a collapsed state for ingestion and an expanded state for retention in the stomach, the expanded-state-articulated body defining a closed polygon, the polygon having a plurality of vertices including at least one hinged vertex and at least one hingeless vertex formed by transitioning the body from the collapsed to the expanded state, the body including, holding, housing, protecting or being mechanically engaged to an erodible;
wherein when the body is exposed to gastric fluids, erosion of the erodible opens the closed circuit and/or disassembles the articulated body for exit from the stomach via the pyloric valve.

67. A GRDF comprising:
an articulated body having a collapsed state for ingestion and an expanded state for retention in the stomach, the expanded-state-articulated body defining a closed polygon, the polygon optionally having a plurality of vertices including at least one hinged vertex and at least one hingeless vertex formed by transitioning the body from the collapsed to the expanded state, the body including, holding, housing, protecting or being mechanically engaged to a pharmaceutical-containing erodible;
wherein when the body is exposed to gastric fluids, pharmaceutical-releasing erosion of the erodible opens the closed circuit and/or disassembles the articulated body for exit from the stomach via the pyloric valve.

68. The GRDF of any preceding clause wherein changes in geometric and/or mechanical properties of the erodible opens the closed circuit and/or disassembles the articulated body 69. The GRDF of any of the preceding clause, wherein opens the closed circuit and/or disassembles the articulated body is dependent on erosion of the tablet.

70. The GRDF of any preceding clause, where the opens the closed circuit and/or disassembles the articulated body commences at greater than 60% erosion, at greater than 70% erosion at greater than 80% erosion at greater than 90% erosion at greater than 95% erosion at 99% or 100% erosion 71. An extended-release method comprising:
providing the GRDF of any clause above;
upon entering the stomach, the body transitions into the expanded state and is retained within the stomach;
subsequently, gastric conditions within the stomach erode the erodible so as to open the closed circuit and/or disassemble the articulated body;
subsequently, the post-cleaving or disassembled body exits the stomach, whole or in pieces, via the pyloric valve.

72. The method of clause 71 wherein before cleaving or disassembly, the GRDF is retained in the stomach for at least 6 hours or at least 12 hours or at least 18 hours or at least 24 hours or at least 2 days or at least 3 days or at last 1 week or at least 2 weeks or at least 1 month.

73. The method of clause 71 wherein an elapsed time between (i) the cleaving and/or disassembly and (ii) the exit of the body via the pyloric valve, is at most 3 hours or at most 2 hours or at most 1 hour or at most 30 minutes.

74. A GRDF comprising:
an articulated body having a collapsed state for ingestion and an expanded state for retention in the stomach, the articulated body comprising first and second hinges connected to each other via a mediating sleeve having an gastric-fluid-insoluble outer surface, a erodible being disposed within the mediating sleeve, each of the hinges being connected to the mediating sleeve such that the connection is maintained by a presence of the erodible is(are) within the mediating sleeves, the mediating sleeve defining void(s) therein, wherein when the erodible is exposed to gastric fluid, erosion of the erodible eliminates a connection between the mediating sleeve and at least one of the first and second hinges to render the body suitable for exit from the stomach via the pyloric valve.

75. A GRDF comprising:
an articulated body having a collapsed state for ingestion and an expanded state for retention in the stomach, the articulated body comprising first and second hinges connected to each other via a mediating sleeve having an gastric-fluid-insoluble outer surface, a pharmaceutical-containing erodible being disposed within the mediating sleeve, each of the hinges being connected to the mediating sleeve such that the connection is maintained by a presence of the erodible is(are) within the mediating sleeves, the mediating sleeve defining void(s) therein, wherein when the erodible is exposed to gastric fluid, pharmaceutical-releasing erosion of the erodible eliminates a connection between the mediating sleeve and at least one of the first and second hinges to render the body suitable for exit from the stomach via the pyloric valve.

76. The GRDF of any preceding clause wherein changes in geometric and/or mechanical properties of the erodible eliminates the connection.

77. The GRDF of any of the preceding clauses, wherein the elimination of the connection is dependent on erosion of the tablet.

78. The GRDF of any preceding clause where the elimination of the connection commences at greater than 60% erosion, at greater than 70% erosion at greater than 80% erosion at greater than 90% erosion at greater than 95% erosion at 99% or 100% erosion.

79. The GRDF of any preceding clause wherein the erodible is a pharmaceutical tablet(s).

80. The GRDF of any preceding clause wherein the first and/or second hinges is unloaded and the mechanical bias is towards the hinge-external.

81. The GRDF of any preceding clause, further comprising an elastic leaf which provides at least some of the mechanical bias.

82. The GRDF of any preceding clause wherein for any given hinge of the GRDF, (i) when in the compressed state, a hinge angle of the given hinge is at most $\theta_1$, (ii) when in the expanded state, a hinge angle of the given hinge is at least $\theta_2$; and (iii) an angular difference $\theta_2-\theta_1$ is at least 10 degrees or at least 20 degrees or at least 30 degrees or at least 40 degrees.

83. The GRDF of any preceding clause wherein at least a majority by length of the first sleeve maintains its structure integrity after cleavage of the connection between the first sleeve and the mediating hinge.

84. The GRDF of any of preceding clause wherein a post-cleavage length of the mediating sleeve is at least 5 mm or at least 10 mm.

85. The GRDF of any preceding clause a ratio between (i) a minimum enclosing ring of the GRDF in the expanded state and (ii) a minimum enclosing ring of the GRDF in the compressed state is at least 1.5 or at least 2 or at least 3 or at least 5 or at least 10 and/or at most 20 or at most 15 or at most 10 or at most 7.5 or at most 5 or at most 4 or at most 3.5

86. The GRDF of any preceding clause a ratio between (i) a minimum enclosing ring of the GRDF in the expanded state and (ii) a minimum enclosing ring of the GRDF in the compressed state is at least 1.5 or at least 2 or at least 2.5 and/or at most 10 or at most 7.5 or at most 5 or at most 4 or at most 3.5.

87. The GRDF of any of preceding clause wherein a ratio between (i) the post-cleavage length of the mediating sleeve and a (ii) a pre-cleavage and expanded-state diameter of a minimum-enclosing sphere of the GRDF, is at least 0.05 or at least 0.1 or at least 0.2 or at least 0.3 or at least 0.5.

88. The GRDF of any preceding clause wherein when the body is in the expanded state and the GRDF is soaked in gastric fluids at 37 degrees Celsius, the mediating hinge remains connected to both the first and second sleeves for at least 12 hours or at least 24 hours or at least 18 hours or at least 2 days or at least 3 days or at least one week or at least two weeks or at least one month.

89. The GRDF of any preceding clause wherein when the body is in the expanded state, static friction between an inner surface of the mediating sleeve and a surface of the sleeve-interior-disposed pharmaceutical tablet(s) disposed within the mediating sleeve maintains the respective connection with the mediating hinge.

90. The GRDF of any preceding clause wherein when the body is in the expanded state, the first hinge is respectively connected to the mediating sleeves in a manner that is static-frictionally-maintained by the erodible within the mediating sleeve.

91. The GRDF of any preceding clause wherein at least 50% or at least 60% or at least 70% or at least 80% or at least 90% or at least 95% or at least 97% or at least 99% of a surface area of the GDRF when in the expanded state, is insoluble in gastric fluid.

92. The GRDF of any preceding clause, wherein at least 50% or at least 75% or at least 90% or at least 95% of an area of an outer surface of the articulated body is gastric-fluid-insoluble.

93. The GRDF of any preceding clause wherein the gastric-fluid-insoluble outer surface of at least a portion of the GRDF or of an arm or sleeve or mediating arm thereof comprises a pH-insensitive polymer 94. The GRDF of the preceding clause wherein the pH insensitive polymer is a non-ionic cellulose ester.

95. The GRDF of the preceding clause wherein the non-ionic cellulose ester is cellulose acetate.

96. The GRDF of any proceeding clause, wherein the mediating side comprises an inner surface in direct contact with the erodible.

97. The GRDF of the preceding clause wherein the inner surface comprises a pH sensitive polymer.

98. The GRDF of the preceding clause wherein at least 50% or at least 75% or at least 90% or at least 95% of an area of the inner surface of the mediating side is a pH sensitive polymer 99. The GRDF of the preceding clause wherein the pH insensitive polymer is HPMS-AS HG, MG or LG.

100. An extended-release method comprising:
providing the GRDF of any of clauses 74-99;
upon entering the stomach, the body transitions into the expanded state and is retained within the stomach;
subsequently, gastric conditions within the stomach erode the tablet(s) so as to cleave the connection between the mediating sleeve and at least one of the hinges;
subsequently, the post-cleaved body exits the stomach, whole or in pieces, via the pyloric valve.

101. An extended-release method comprising:
providing the GRDF of any of clauses 74-99;
upon entering the stomach, the body transitions into the expanded state and is retained within the stomach;
subsequently, gastric conditions within the stomach induce pharmaceutical-releasing erosion of the tablet(s) so as to cleave the connection between the mediating sleeve and at least one of the hinges;
subsequently, the post-cleaved body exits the stomach, whole or in pieces, via the pyloric valve.

102. The method of any one of clauses 99-100 wherein at least 50% or at least 60% or at least 70% or at least 80% or at least 90% or at least 95% or at least 97% or at least 99% of a surface area of the GDRF when in the expanded state, is insoluble in gastric fluid.

103. An extended release method comprising:
providing a gastroretentive dosage form (GRDF) having a collapsed state for ingestion and an expanded state for retention within the stomach, the GDRF further comprising an active pharmaceutical ingredient (API);
upon entering the stomach, the GDRF transitions from the collapsed state to the expanded state;
after transitioning into the expanded state,-the GDRF is retained within the stomach;

while in the stomach, conditions within the stomach cause at least partial release of the API;

while in the stomach, conditions within the stomach induce cleavage and/or disassembly of the GDRF; and subsequently, the post-disassembled or post-cleaved GDRF, whole or in pieces, exits the stomach.

104. An extended release method comprising:

providing a gastroretentive dosage form (GRDF) having a collapsed state for ingestion and an expanded state for retention within the stomach, the GDRF further comprising an active pharmaceutical ingredient (API);

upon entering the stomach, the GDRF transitions from the collapsed state to the expanded state;

after transitioning into the expanded state,-the shape and mechanical properties of the GDRF cause the GDRF to be retained within the stomach;

while in the stomach, conditions within the stomach cause at least partial release of the API;

while in the stomach, conditions within the stomach induce sufficient cleavage and/or disassembly to sufficiently modify the GDRF so that it exits whole or in pieces, from the stomach.

105. The method of any clauses 103-104 wherein stomach-exiting-disassembly of the GDRF occurs only after retention in the stomach of at least 1 day or at least 36 hours or at least 2 days or at least 3 days or about one week or about two weeks or about a month.

106. An extended release method comprising:

providing a gastroretentive dosage form (GRDF) having a collapsed state for ingestion and an expanded state for retention within the stomach, the GDRF further comprising an active pharmaceutical ingredient (API);

upon entering the stomach, the GDRF transitions from the collapsed state to the expanded state;

after transitioning into the expanded state,-the GDRF is retained within the stomach;

while in the stomach, an API releasing event occurs where a quantity of the API is released from then GDRF, the API-releasing event causing cleavage and/or disassembly of the GDRF; and subsequently, the post-disassembled or post-cleaved GDRF, whole or in pieces, exits the stomach.

107. The method of any preceding clause wherein at least 50% or at least 60% or at least 70% or at least 80% or at least 90% or at least 95% or at least 97% or at least 99% of a surface area of the GDRF, in the expanded state, is insoluble in gastric fluids.

108. The method of any preceding clause wherein:

the GDRF comprises gastric-fluid-soluble material disposed within gastric-fluid-insoluble shell defining void(s) therein;

within the stomach, gastric fluids penetrate into an interior of the gastric-fluid-insoluble via the void(s); and the cleavage and/or disassembly is caused by erosion of the gastric-fluid-soluble material by the post-penetration gastric fluids.

109. The method of any preceding clause wherein release of a threshold amount of API is required in order for the conditions within the stomach to induce the cleavage and/or to induce the disassembly of the GDRF.

110. The method of any preceding clause wherein the GDRF comprises one or more hinges, and conditions within the stomach detach the hinge from another portion of the body so as to sufficiently degrade or reduce the GDRF to exit the stomach.

111. The method of any preceding clause wherein the GDRF is retained within the stomach for at least 1 hour or at least 3 hours or at least 4 hours or at least 6 hours or at least 9 hours or at least 12 hours or at least 15 hours or at least 18 hours or a least 24 hours or at least 48 hours or at least 3 days or at least 1 week.

112. The method of any preceding clause, performed using any GDRF disclosed herein.

113. The GRDF of any preceding clause wherein gastric retentive endpoint and/or opening the closed circuit and/or disassembly of the articulated body and/or cleaving the connection between the mediating sleeve and at least one of the hinges occurs when release of active is greater than 30%, greater than 40%, greater than 50%, greater than 60%, greater than 70%, greater than 80%, greater than 90% or greater than 95%.

114. The GRDF of any preceding clause wherein the expanded state is capable of maintaining dimensional strength and strength under repeated forces over a period of time in the gastric environment and/or until about more than 50%, 60%, 70%, 80% or 90% erosion of the erodible and/or until about 10%, 20%, 30%, 40%, 50%, 60%, 70%, 80%, 90% release of active.

115. The GRDF of any preceding clause wherein erosion of erodible is at a rate similar to zero order.

116. A GRDF comprising:

an articulated body having a collapsed state for ingestion and an expanded state for retention in the stomach, the expanded-state body defining a closed polygon, wherein the body includes, houses, holds or is mechanically engaged to a erodible so that erosion of the erodible causes the polygon to dismantle so as to separate units of the body from each other, each of the units sized for exit from the stomach via the pyloric valve.

The GRDF of clause 116 wherein the erodible is a pharmaceutical-containing erodible and the erosion which disconnects the mediating side from the at least one hinge is pharmaceutical-releasing erosion.

What is claimed:

1. A device for extended retention in the stomach of a human subject after being swallowed by the subject, the device comprising:
    a first arm comprising a first end and a second opposing end, a second arm and a third arm, the second and third arms being pivotally connected to the first end and the second end of the first arm, respectively,
    wherein the device is configured to transform between a compressed configuration and an expanded configuration,
    wherein in the compressed configuration, the device has a size suitable for swallowing by the human subject;
    wherein the first, second and third arms swell less than about 10 vol % in gastric fluid; and
    wherein in the expanded configuration, the device comprises a smallest turning radius of greater than 20 mm with reference to a human pyloric valve, which resists passage through a pyloric valve of the subject.

2. The device according to claim 1, wherein in the expanded configuration, the smallest turning radius is greater than about 26 mm.

3. The device according to claim 1, wherein in the expanded configuration, the smallest turning radius is less than about 35 mm.

4. The device according to claim 3, wherein in the expanded configuration, the smallest turning radius is less than about 28 mm.

5. The device according to claim 1, wherein the convex hull volume in the compressed configuration comprises about 30% of the expanded configuration convex hull volume.

6. The device according to claim 1, wherein the device is able to withstand forces in every orientation of greater than 250 gF for a period of greater than 4 hours in a human stomach or simulated model.

7. The device according to claim 6, wherein the force withstood is greater than 400gF.

8. The device according to claim 1, wherein after a predetermined time period in the expanded configuration, the device is configured to disassemble.

9. The device according to claim 8, wherein disassembly of the device comprises disconnection of the second and/or third arms from the first arm.

10. The device according to claim 9, wherein upon disconnection of the second and/or third arms from the first arm, a connection between the second and third arms is disengaged.

11. The device according to claim 1, wherein the first arm is a tube or sleeve.

12. The device according to claim 11, wherein the tube or sleeve comprises a cavity.

13. The device according to claim 12, wherein the cavity is configured to contain an erodible insert, diagnostic, electronic device, or combinations thereof.

14. The device according to claim 13, wherein the erodible insert comprises a pharmaceutical, diagnostic, or electronic device.

15. The device according to claim 12, wherein the first arm comprises an opening through which gastric fluid can enter the cavity.

16. The device according to claim 1, wherein during transformation from the compressed configuration to the expanded configuration, an outer surface of the second arm is configured to slide along the third arm.

17. The device according to claim 1, wherein in the expanded configuration the first, second, and third arms are configured to form a generally triangular shape.

18. A device for extended retention in the stomach of a human subject after being swallowed by the subject, the device comprising:

a. a first arm comprising a first end and a second opposing end;
   b. a second arm pivotally connected to the first end of the first arm;
   c. a third arm pivotally connected to the second end of the first arm; and
   d. a biasing member connected to the second end of the first arm, the biasing member configured to transition the device from a compressed configuration to an expanded configuration, wherein in the compressed configuration, the device has a size suitable for swallowing by the human subject;
   wherein the first, second and third arms swell less than about 10 vol % in gastric fluid, and
   wherein in the expanded configuration, the device has a smallest turning radius of greater than 20 mm with reference to a human pyloric valve, which resists passage through a pyloric valve of the subject.

19. A device for extended retention in the stomach of a human subject after being swallowed by the subject, the device comprising:

an articulated body having a collapsed state for ingestion and an expanded state for retention in the stomach, the collapsed-state articulated body having first and second ends, wherein in the compressed configuration, the device has a size suitable for swallowing by the human subject:
   wherein exposure of the device to gastric fluid transitions the body from the collapsed state to the expanded state,
   wherein the body swells less than about 10 vol % in gastric fluid, and
   wherein in the expanded state, the device has a smallest turning radius of greater than 20 mm with reference to a human pyloric valve, which resists passage through a pyloric valve of the subject.

20. A method of delivering an active pharmaceutical to the stomach for extended periods of time comprising: providing a device according to claim 1, wherein one of the first, second, and third arms comprises an active pharmaceutical.

* * * * *